United States Patent
Yokoyama et al.

(10) Patent No.: US 8,252,431 B2
(45) Date of Patent: Aug. 28, 2012

(54) COMPOUND WHEREIN SUBSTITUTED BIPYRIDYL GROUP IS CONNECTED WITH PYRIDOINDOLE RING STRUCTURE THROUGH PHENYLENE GROUP, AND ORGANIC ELECTROLUMINESCENT DEVICE

(75) Inventors: Norimasa Yokoyama, Ibaraki (JP); Shuichi Hayashi, Ibaraki (JP); Shigeru Kusano, Ibaraki (JP); Makoto Nagaoka, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 353 days.

(21) Appl. No.: 12/531,365

(22) PCT Filed: Mar. 13, 2008

(86) PCT No.: PCT/JP2008/054624
§ 371 (c)(1),
(2), (4) Date: Sep. 15, 2009

(87) PCT Pub. No.: WO2008/114690
PCT Pub. Date: Sep. 25, 2008

(65) Prior Publication Data
US 2010/0123388 A1 May 20, 2010

(30) Foreign Application Priority Data
Mar. 15, 2007 (JP) .................... 2007-066214

(51) Int. Cl.
*H01L 51/54* (2006.01)
(52) U.S. Cl. ........ 428/690; 428/917; 313/504; 313/505; 313/506; 257/40; 257/E51.032
(58) Field of Classification Search .................. 428/690, 428/917; 313/504, 505, 506; 257/40, E51.032
See application file for complete search history.

(56) References Cited

U.S. PATENT DOCUMENTS

| 2005/0249970 A1 | 11/2005 | Suzuri et al. | |
| 2006/0216411 A1* | 9/2006 | Steudel et al. | 427/66 |
| 2006/0251918 A1* | 11/2006 | Iwakuma et al. | 428/690 |

FOREIGN PATENT DOCUMENTS

| EP | 1 571 193 A1 | 9/2005 |
| JP | 2006 32599 | 2/2006 |
| WO | 2004 053019 | 6/2004 |
| WO | 2007 029696 | 3/2007 |

OTHER PUBLICATIONS

U.S. Appl. No. 12/377,908, filed Feb. 18, 2009, Yokoyama, et al.

* cited by examiner

*Primary Examiner* — Jennifer Chriss
*Assistant Examiner* — Gregory Clark
(74) *Attorney, Agent, or Firm* — Oblon, Spivak, McClelland, Maier & Neustadt, L.L.P.

(57) ABSTRACT

An organic compound is provided having excellent electron-injection/transport performance, hole-blocking ability, and high stability in a thin-film state. An organic electroluminescence device having a high efficiency and a high durability is provided, using the compound. The compound has a substituted bipyridyl group and a pyridoindole ring structure connected with each other through a phenylene group, is of formula (1). The organic EL device has a pair of electrodes and at least one organic layer interposed between the electrodes, wherein the compound is a constituent material for an organic layer therein.

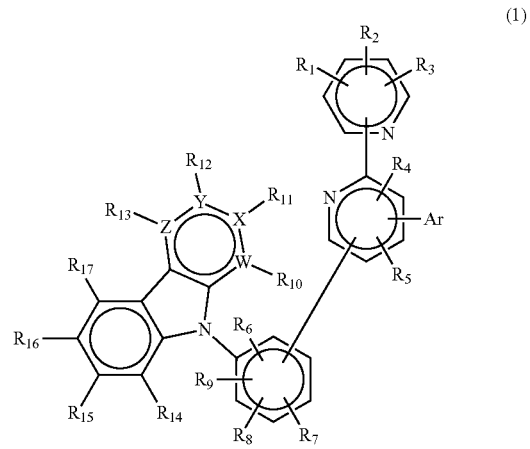

20 Claims, 8 Drawing Sheets

COMPOUND WHEREIN SUBSTITUTED BIPYRIDYL GROUP IS CONNECTED WITH PYRIDOINDOLE RING STRUCTURE THROUGH PHENYLENE GROUP, AND ORGANIC ELECTROLUMINESCENT DEVICE

TECHNICAL FIELD

The present invention relates to a compound suitable for an organic electroluminescence (EL) device which is a self-luminescent device suitable for various displaying devices and a device. More specifically, it relates to a compound having a substituted bipyridyl group and a pyridoindole ring structure connected with each other through a phenylene group and to an organic EL device using the compound.

BACKGROUND ART

Since organic EL devices are self-luminescent devices, they are bright and excellent in visibility as compared with liquid-crystalline devices and capable of giving clear display, so that the organic EL devices have been actively studied.

In 1987, C. W. Tang et al. of Eastman Kodak Company put an organic EL device using organic materials into practical use by developing a device having a multilayered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m$^2$ or more at a voltage of 10 V or lower (see e.g., Patent Documents 1 and 2).
Patent Document 1: JP-A-8-48656
Patent Document 2: Japanese Patent No. 3194657

To date, many improvements have been performed for practical utilization of the organic EL devices, and high efficiency and durability have been achieved by an electroluminescent device wherein an anode, a hole-injecting layer, a hole-transporting layer, an emitting layer, an electron-transporting layer, an electron-injecting layer, and a cathode are sequentially provided on a substrate, to further segmentalize various roles (see e.g., Non-Patent Document 1).
Non-Patent Document 1: Japan Society of Applied Physics Ninth Workshop Preprint, pp. 55-61 (2001)

Moreover, for the purpose of further improvement of luminous efficiency, utilization of triplet exciton has been attempted and utilization of a phosphorescent material has been investigated (see e.g., Non-Patent Document 2).
Non-Patent Document 2: Japan Society of Applied Physics Ninth Workshop Preprint, pp. 23-31 (2001)

The emitting layer can be also prepared by doping a charge-transporting compound, generally called a host material, with a fluorescent material or a phosphorescent material. As described in the above-mentioned Workshop Preprints, the choice of the organic materials in organic EL devices remarkably affects various properties such as efficiency and durability of the devices.

In the organic EL devices, the charges injected from the both electrode are recombined in the emitting layer to attain light emission. However, since the mobility of holes is higher than the mobility of electrons, a problem of reduction in efficiency caused by a part of the holes passing through the emitting layer arises. Therefore, it is required to develop an electron-transporting material in which the mobility of electrons is high.

A representative light-emitting material, tris(8-hydroxyquinoline)aluminum (hereinafter referred to as Alq3) is commonly used also as an electron-transporting material but it cannot be considered that the material has hole-blocking capability.

As a technique to prevent the passing of a part of holes through the emitting layer and to improve probability of charge recombination in the emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (BAlq) (see e.g., Non-Patent Document 2), and the like.

For example, as an electron-transporting material excellent in hole-blocking ability, there is proposed 3-(4-biphenyl)-1)-4-phenyl-5-(4-t-butylphenyl)-1,2,4-triazole (hereinafter referred to as TAZ) (see e.g., Patent Document 3).
Patent Document 3: Japanese Patent No. 2734341

Since TAZ has a work function as large as 6.6 eV and thus exhibits a high hole-blocking ability, it is used as an electron-transporting hole-blocking layer to be laminated onto the cathode side of a fluorescence-emitting layer or phosphorescence-emitting layer prepared by vacuum deposition, coating or the like, and contributes to increase the efficiency of organic EL devices (see e.g., Non-Patent Document 3).
Non-Patent Document 3: Fiftieth Meeting of Japan Society of Applied Physics and Related Societies, 28p-A-6 Lecture Preprint, p. 1413 (2003)

However, TAZ has a great problem of having low electron transport property, and it is necessary to prepare an organic EL device in combination with an electron-transporting material having a higher electron transport property (see e.g., Non-Patent Document 4).
Non-Patent Document 4: Japan Society of Applied Physics, Journal of Organic Molecules/Bioelectronics Section, Vol. 11, No. 1, pp. 13-19 (2000)

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in film stability or are insufficient in the function of blocking holes. In order to improve characteristic properties of the organic EL devices, it is desired to develop an organic compound which is excellent in electron-injection/transport performances and hole-blocking ability and is highly stable in a thin-film state.

DISCLOSURE OF THE INVENTION

Problems to be Solved by the Invention

Objects of the present invention are to provide an organic compound having excellent properties, which is excellent in electron-injection/transport performances, has hole-blocking ability and is highly stable in a thin-film state, as a material for an organic electroluminescence device having a high efficiency and a high durability, and to provide an organic electroluminescence device having a high efficiency and a high durability using the compound.

As physical properties of the organic compound to be provided by the invention, there may be mentioned (1) good electron injection characteristic, (2) high electron mobility, (3) excellent hole-blocking ability, (4) good stability in a thin-film state, and (5) excellent thermal resistance. In addition, as physical properties of the organic EL device to be provided by the invention, there may be mentioned (1) high luminous efficiency, (2) low emission initiation voltage, (3) low practical driving voltage, and (4) high maximum emission luminance.

Means for Solving the Problems

Thus, in order to achieve the above objects, the present inventors have designed and chemically synthesized compounds having a substituted bipyridyl group and a pyridoindole ring structure connected with each other through a phenylene group, with focusing on the fact that the nitrogen atom of the pyridine ring which exhibits affinity to an electron has an ability of coordinating to a metal and is excellent in thermal resistance. The present inventors have experimentally produced various organic EL devices using the compounds, and have extensively performed property evaluation of the devices. As a result, they have accomplished the invention.

Namely, the invention provides a compound having a substituted bipyridyl group and a pyridoindole ring structure connected with each other through a phenylene group, which is represented by the general formula (1). Also, the invention provides an organic EL device comprising a pair of electrodes and at least one organic layer interposed between the electrodes, wherein the compound is used as a constituent material for the at least one organic layer:

[Chem. 1]

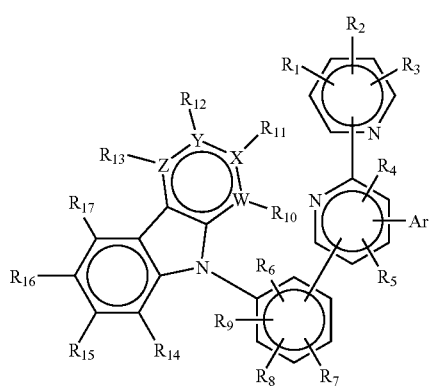

(1)

wherein Ar represents a substituted or unsubstituted aromatic hydrocarbon group, a substituted or unsubstituted aromatic heterocyclic group, or a substituted or unsubstituted condensed polycyclic aromatic group; R1 to R17 may be the same or different and represent a hydrogen atom, a fluorine atom, a chlorine atom, a cyano group, a trifluoromethyl group, a linear or branched alkyl group having 1 to 6 carbon atoms, or a substituted or unsubstituted aromatic hydrocarbon group; and W, X, Y, and Z represent a carbon atom or a nitrogen atom; provided that only one of W, X, Y, and Z is a nitrogen atom and the nitrogen atom does not have a substituent of R10, R11, R12, or R13.

The "aromatic hydrocarbon group", "aromatic heterocyclic group" and "condensed polycyclic aromatic group" in the substituted or unsubstituted aromatic hydrocarbon group, substituted or unsubstituted aromatic heterocyclic group, or substituted or unsubstituted condensed polycyclic aromatic group, which is represented by Ar in the general formula (1) specifically includes a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, and an acridinyl group.

The "substituent" in the substituted aromatic hydrocarbon group, substituted aromatic heterocyclic group, and substituted condensed polycyclic aromatic group represented by Ar in the general formula (1) specifically includes groups such as a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

The "aromatic hydrocarbon group" in the substituted or unsubstituted aromatic hydrocarbon group represented by R1 to R17 in the general formula (1) specifically includes a phenyl group, a biphenyl group, a terphenyl group, a tetrakisphenyl group, a styryl group, a naphthyl group, a fluorenyl group, a phenanthryl group, an indenyl group, and a pyrenyl group.

The "substituent" in the substituted aromatic hydrocarbon group represented by R1 to R17 in the general formula (1) specifically includes a fluorine atom, a chlorine atom, a trifluoromethyl group, and a linear or branched alkyl group having 1 to 6 carbon atoms. These substituents may be further substituted.

The compound having a substituted bipyridyl group and a pyridoindole ring structure connected with each other through a phenylene group, which is represented by the general formula (1) of the invention, provides high electron mobility as compared with conventional electron-transporting materials, has an excellent hole-blocking ability, and is stable in a thin-film state.

The compound having a substituted bipyridyl group and a pyridoindole ring structure connected with each other through a phenylene group, which is represented by the general formula (1) of the invention, can be used as a constituent material for an electron-transporting layer of an organic EL device. The use of the material exhibiting a higher electron injection/mobile rate as compared with conventional materials provides effects of improving electron transport efficiency from the electron-transporting layer to an emitting layer to enhance luminous efficiency and also lowering a driving voltage to enhance durability of the organic EL device.

The compound having a substituted bipyridyl group and a pyridoindole ring structure connected with each other through a phenylene group, which is represented by the general formula (1) of the invention, can be also used as a constituent material for a hole-blocking layer of an organic EL device. The use of the material excellent in hole-blocking ability and also excellent in electron transport property as compared with conventional materials and having high stability in a thin-film state provides effects of lowering a driving voltage, improving current resistance, and enhancing maximum emission luminance of the organic EL device, while exhibiting high luminous efficiency.

The compound having a substituted bipyridyl group and a pyridoindole ring structure connected with each other through a phenylene group, which is represented by the general formula (1) of the invention, can be also used as a constituent material for an emitting layer of an organic EL device.

The use of an emitting layer prepared by using the material of the invention excellent in electron transport property as compared with conventional materials and having a wide bandgap as a host material for the emitting layer and making a fluorescent material or a phosphorescent material, called a dopant, carried thereon provides an effect of realizing an organic EL device exhibiting a lowered driving voltage and having improved luminous efficiency.

Advantageous Effects of the Invention

According to the invention, there is provided a compound having a substituted bipyridyl group and a pyridoindole ring structure connected with each other through a phenylene group, which is useful as a constituent material for an electron-transporting layer, a hole-blocking layer, or an emitting layer of an organic EL device. Further, since the organic EL device prepared by using the compound having a substituted bipyridyl group and a pyridoindole ring structure connected with each other through a phenylene group exhibits high electron mobility as compared with conventional electron-transporting materials, has an excellent hole-blocking ability, and is stable in a thin-film state, it becomes possible to realize a high efficiency and a high durability.

DESCRIPTION OF REFERENCE NUMERALS AND SIGNS

Figure 1:
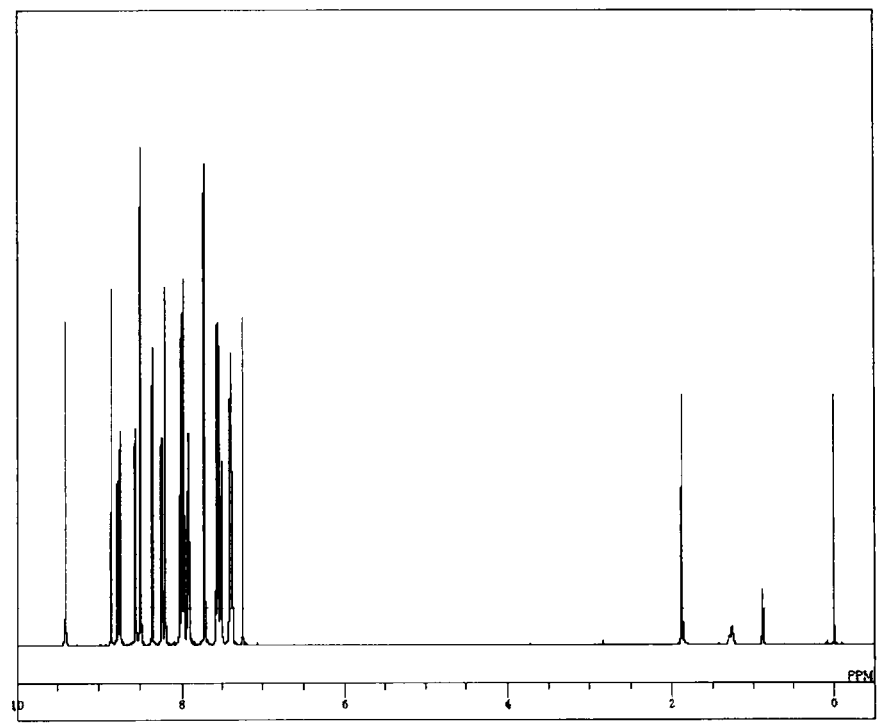
FIG. 1 is a 1H-NMR chart of the compound (Compound 36) of Invention Example 1.

1: Glass substrate
2: Transparent anode
3: Hole-injecting layer
4: Hole-transporting layer
5: Emitting layer
6: Hole-blocking layer
7: Electron-transporting layer
8: Electron-injecting layer
9: Cathode

BEST MODE FOR CARRYING OUT THE INVENTION

The compound having a substituted bipyridyl group and a pyridoindole ring structure connected with each other through a phenylene group according to the invention is a novel compound, and the compound can be synthesized, for example, by subjecting a corresponding halogenoanilinopyridine to a cyclization reaction with a palladium catalyst to synthesize a pyridoindol ring (see e.g., Non-Patent Document 5) and then by condensing it with one of various halogenophenylenes having a substituted bipyridyl group to synthesize a compound having a substituted bipyridyl group and a pyridoindole ring structure connected with each other through a phenylene group. Each of the various halogenophenylenes having a bipyridyl group can be synthesized by condensing a corresponding aldehyde and an acetylpyridine in the presence of a base and further reacting the resulting product with a corresponding pyridinium iodide (see e.g., Non-Patent Document 6).

Non-Patent Document 5: J. Chem. Soc., Perkin Trans. 1, p. 1505 (1999)

Non-Patent Document 6: Synthesis, 1 (1976)

Among the compounds having a substituted bipyridyl group and a pyridoindole ring structure connected with each other through a phenylene group, which is represented by the general formula (1), specific examples of preferred compounds are shown below, but the invention is not limited to these compounds.

[Chem. 2]

(Compound 2)

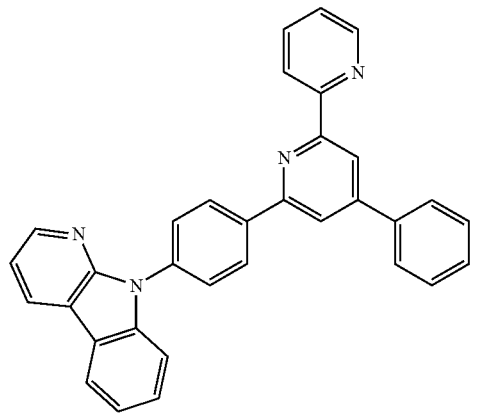

-continued
(Compound 3)
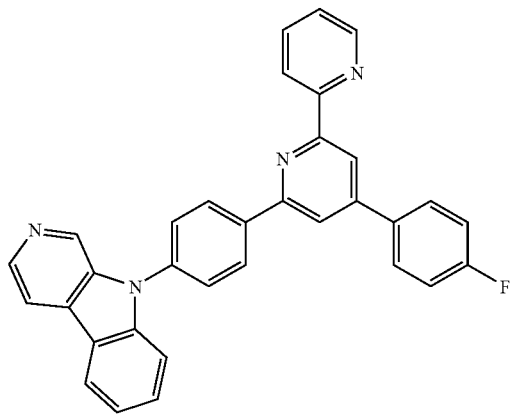
(Compound 6)
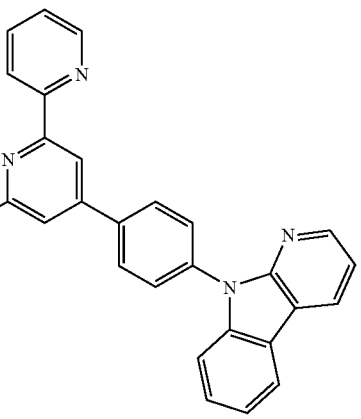
(Compound 4)
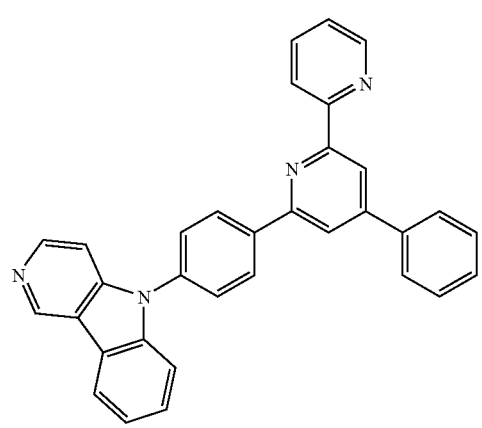
(Compound 7)
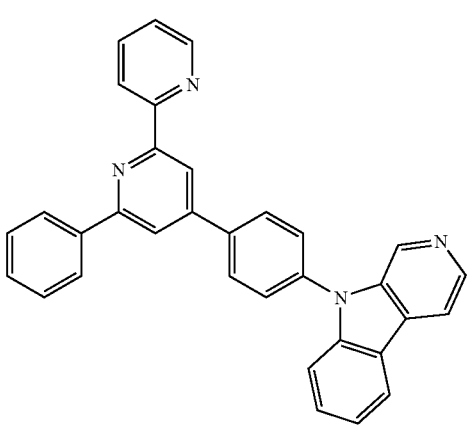
(Compound 5)
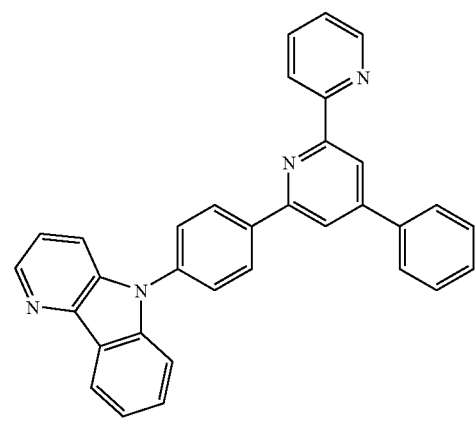
(Compound 8)
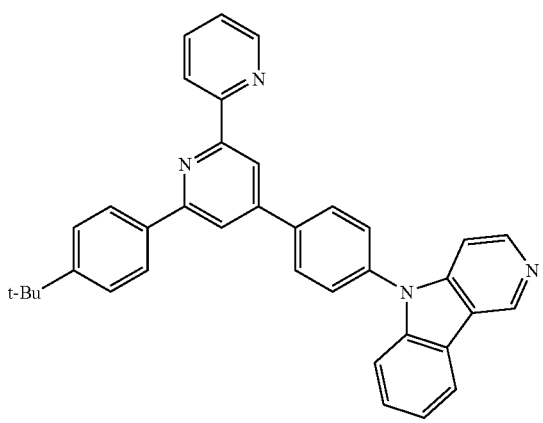

-continued
[Chem. 9]
(Compound 9)
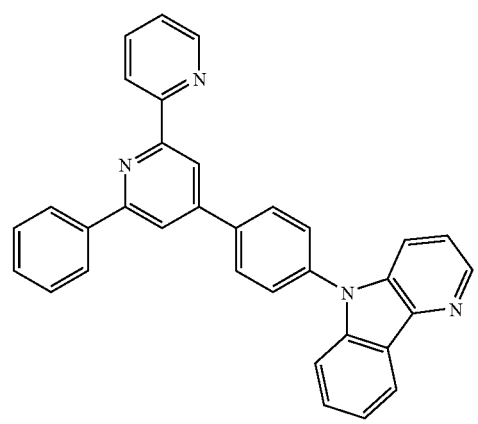
[Chem. 10]
(Compound 10)
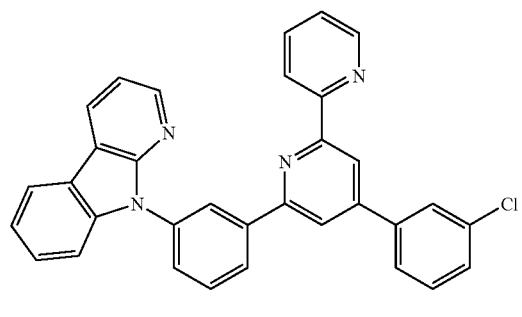
[Chem. 11]
(Compound 11)
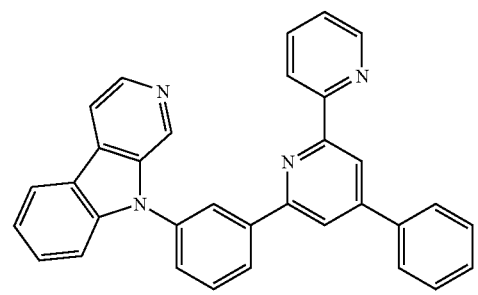
[Chem. 12]
(Compound 12)
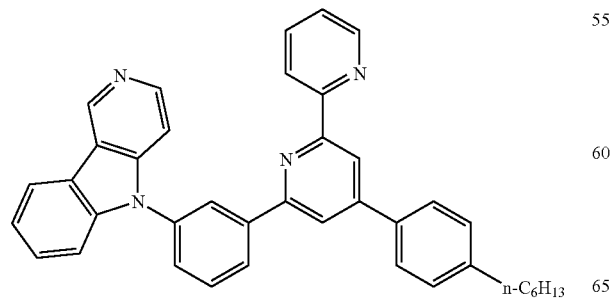
-continued
[Chem. 13]
(Compound 13)
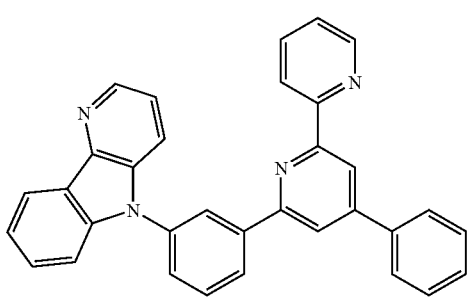
[Chem. 14]
(Compound 14)
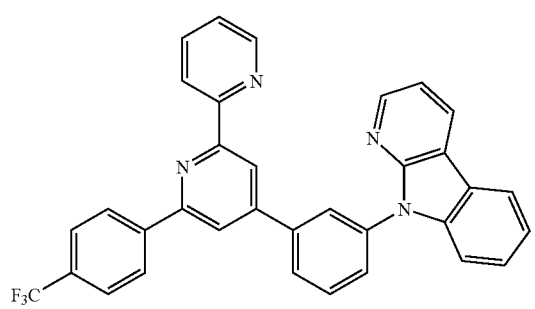
[Chem. 15]
(Compound 15)
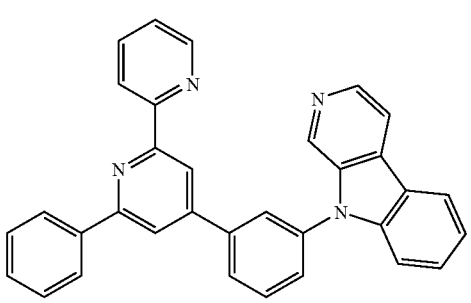
[Chem. 16]
(Compound 16)
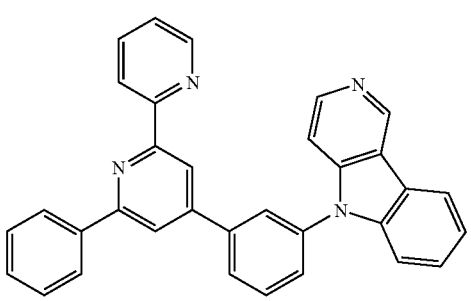

[Chem. 17]
(Compound 17)
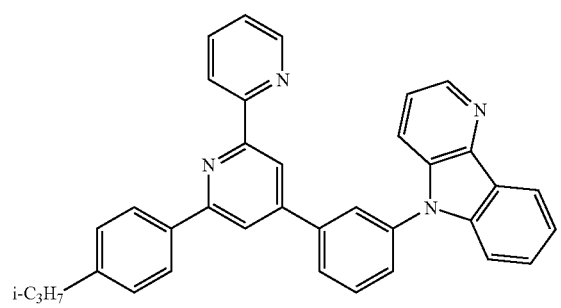
[Chem. 18]
(Compound 18)
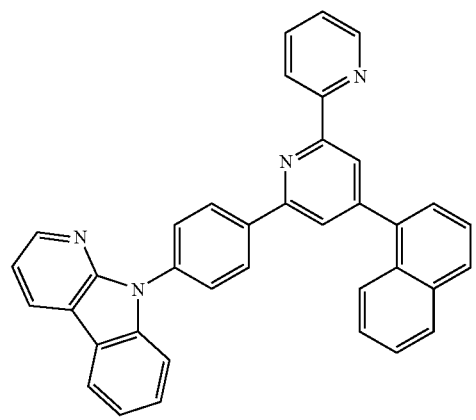
[Chem. 19]
(Compound 19)
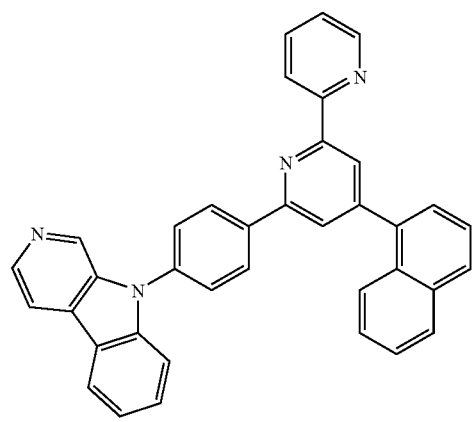
[Chem. 20]
(Compound 20)
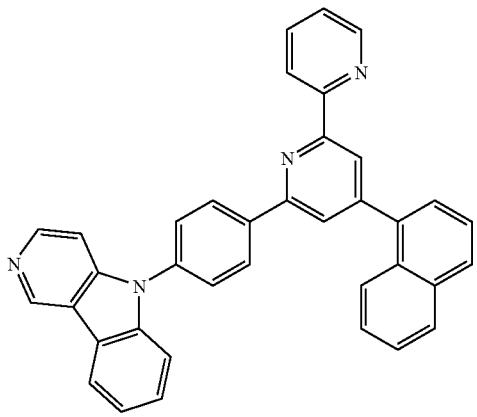
[Chem. 21]
(Compound 21)
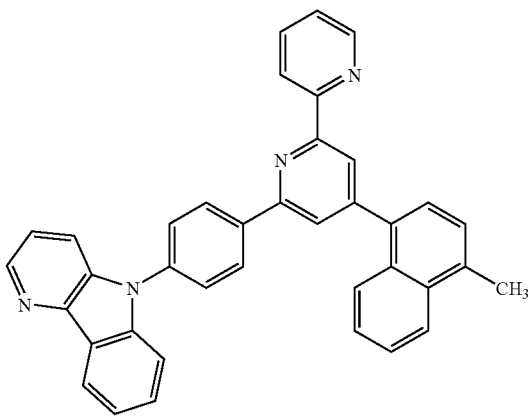
[Chem. 22]
(Compound 22)
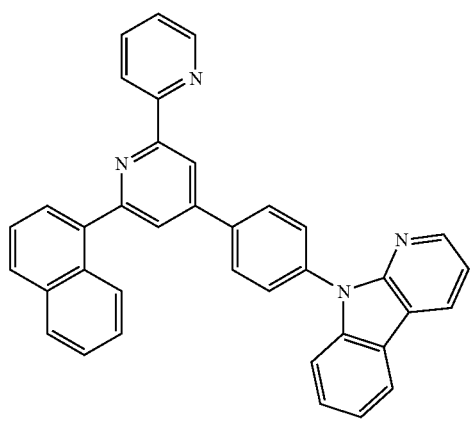

[Chem. 23]
(Compound 23)
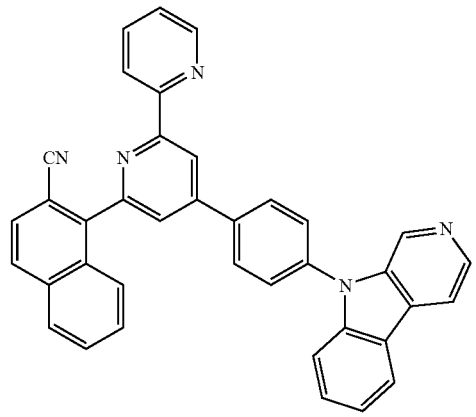
[Chem. 24]
(Compound 24)
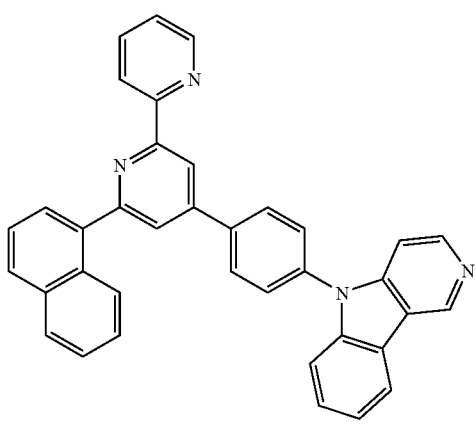
[Chem. 25]
(Compound 25)
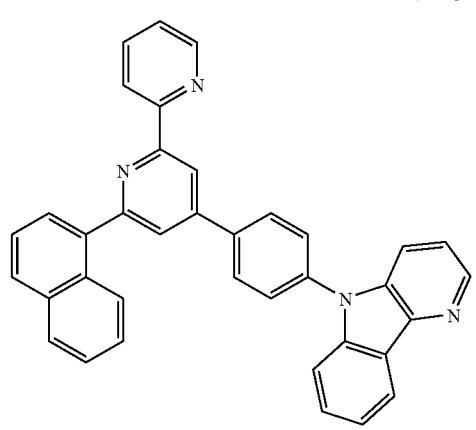
[Chem. 26]
(Compound 26)
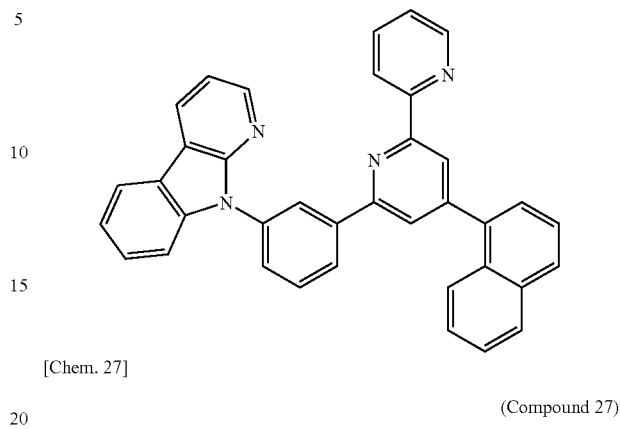
[Chem. 27]
(Compound 27)
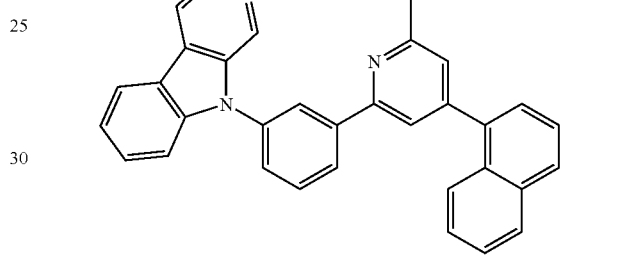
[Chem. 28]
(Compound 28)
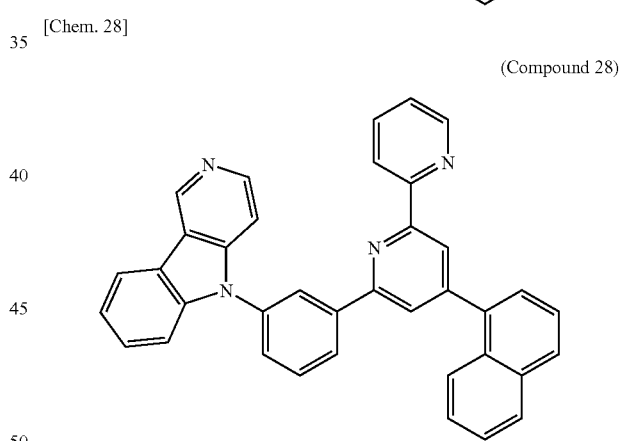
[Chem. 29]
(Compound 29)
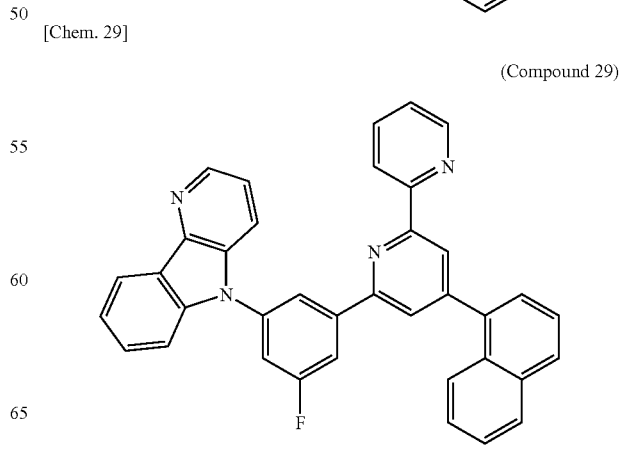

-continued
[Chem. 30]
(Compound 30)
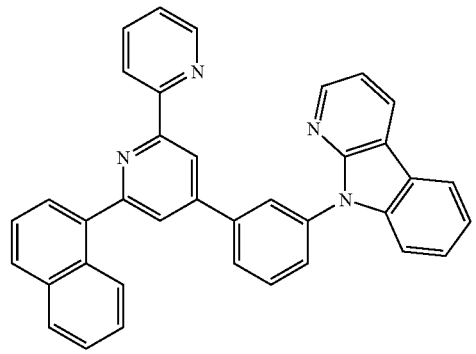
[Chem. 31]
(Compound 31)
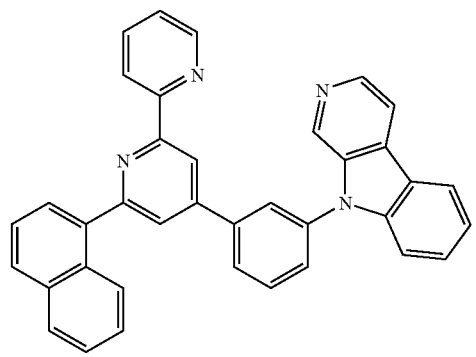
[Chem. 32]
(Compound 32)
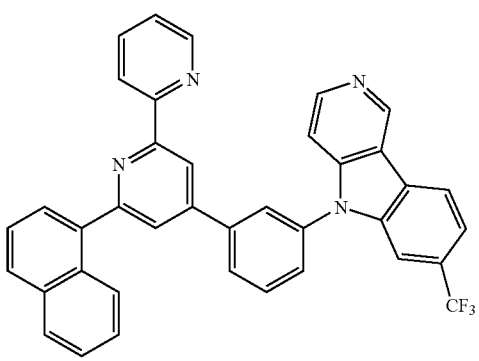
[Chem. 33]
(Compound 33)
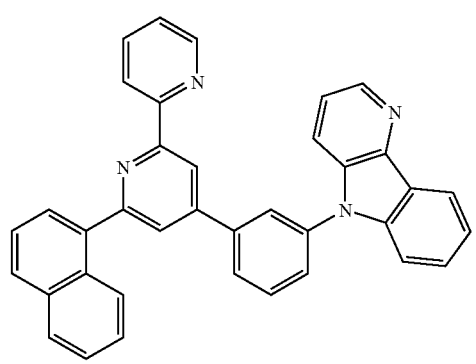
-continued
[Chem. 34]
(Compound 34)
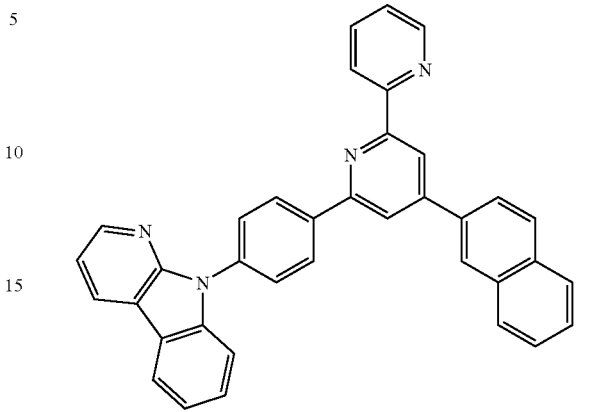
[Chem. 35]
(Compound 35)
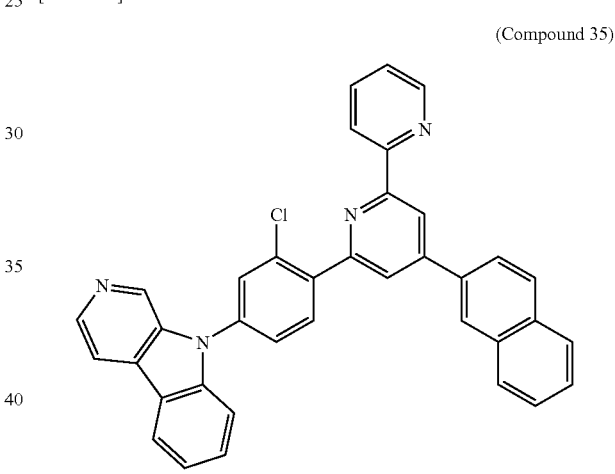
[Chem. 36]
(Compound 36)
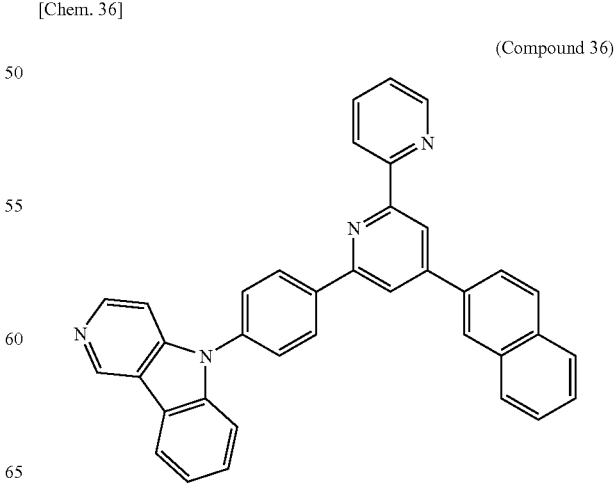

[Chem. 37]
(Compound 37)
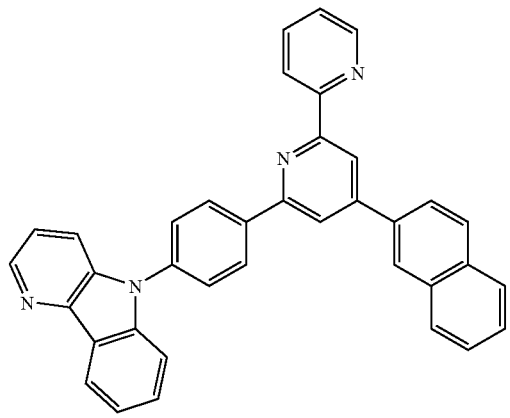
[Chem. 38]
(Compound 38)
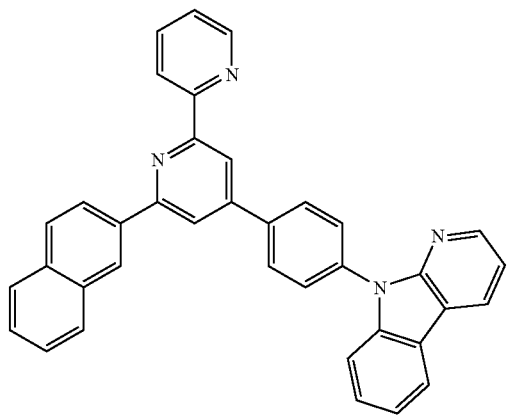
[Chem. 39]
(Compound 39)
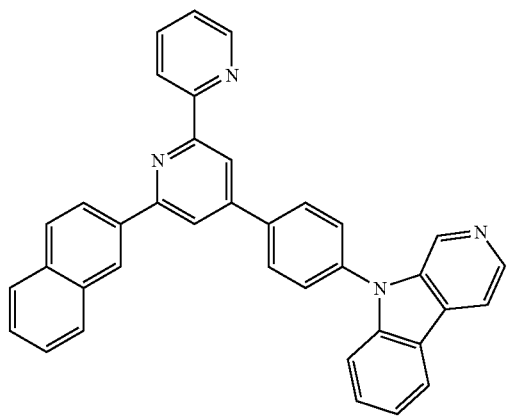
[Chem. 40]
(Compound 40)
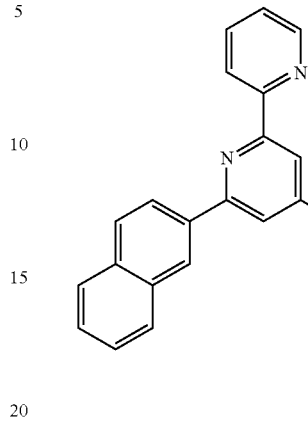
[Chem. 41]
(Compound 41)
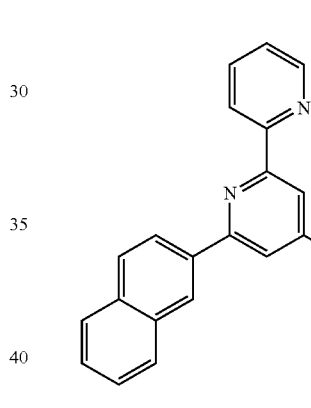
[Chem. 42]
(Compound 42)
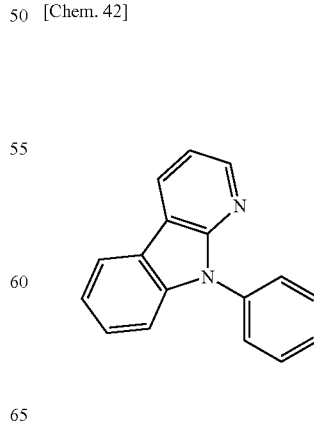

[Chem. 43]
(Compound 43)
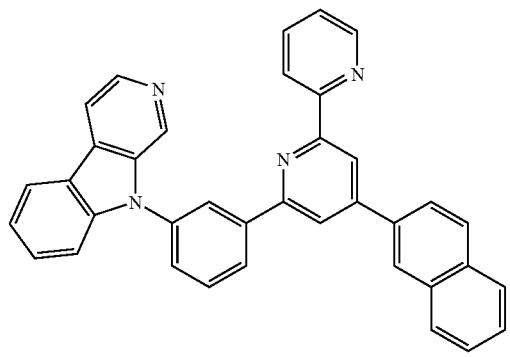
[Chem. 44]
(Compound 44)
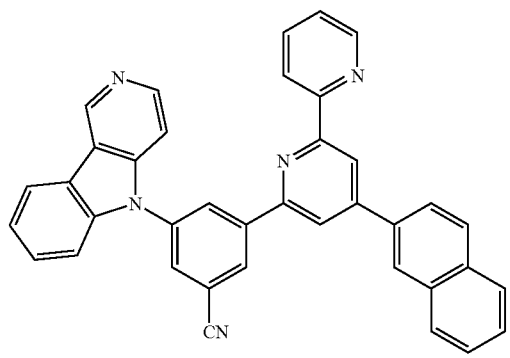
[Chem. 45]
(Compound 45)
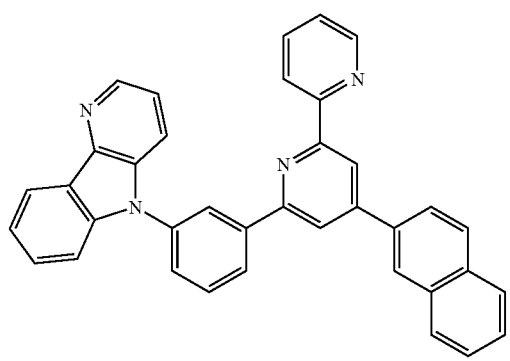
[Chem. 46]
(Compound 46)
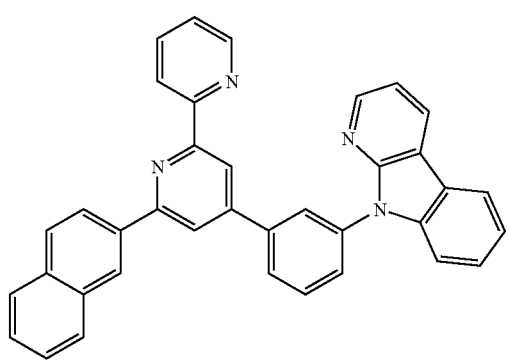
[Chem. 47]
(Compound 47)
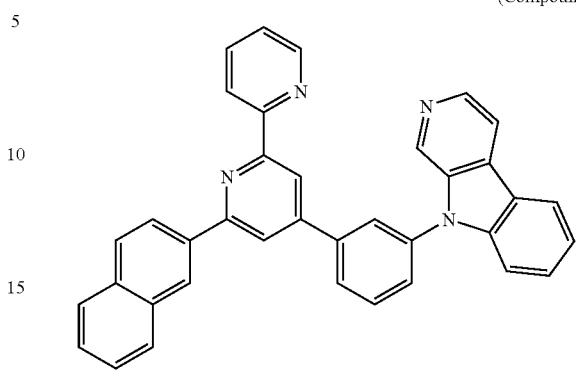
[Chem. 48]
(Compound 48)
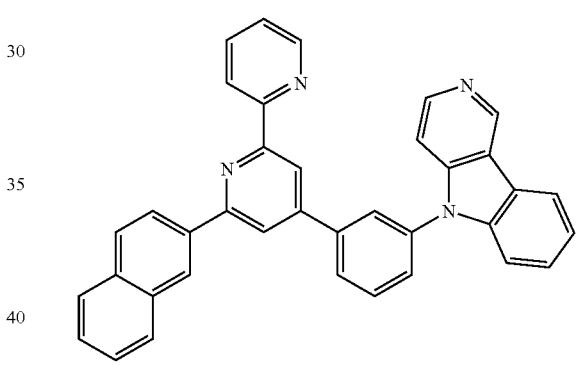
[Chem. 49]
(Compound 49)
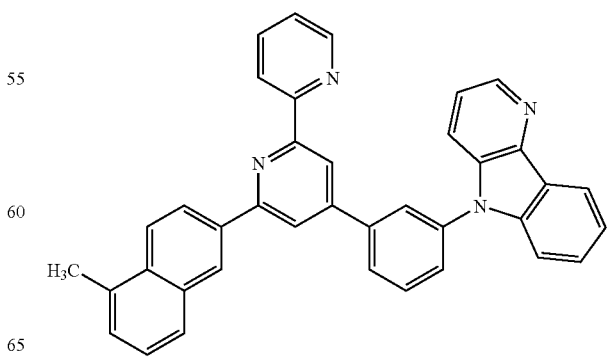

[Chem. 50]
(Compound 50)
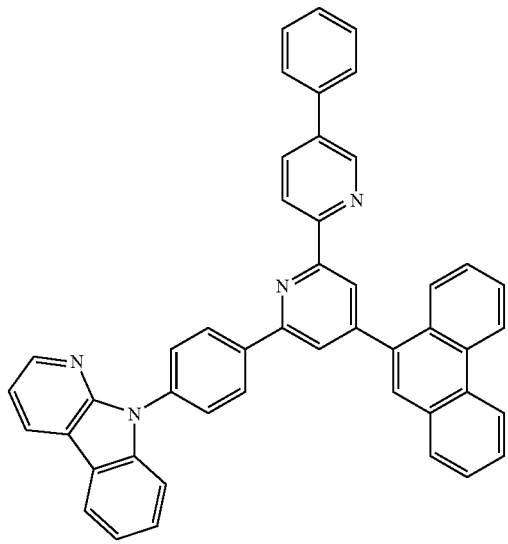
[Chem. 51]
(Compound 51)
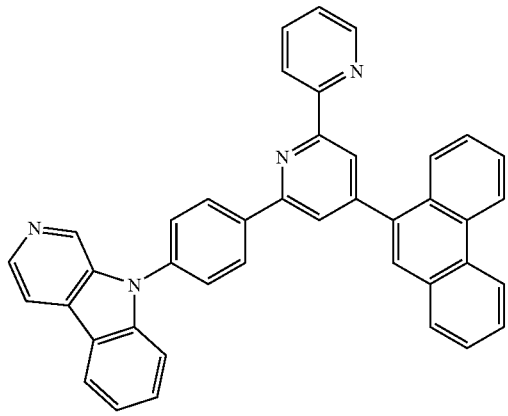
[Chem. 52]
(Compound 52)
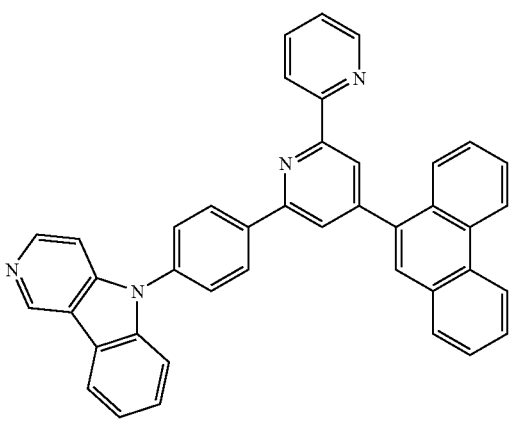
[Chem. 53]
(Compound 53)
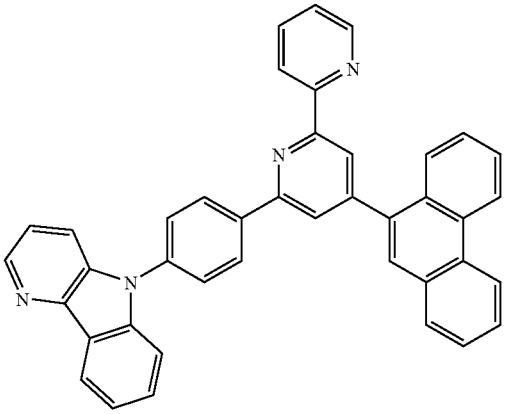
[Chem. 54]
(Compound 54)
[Chem. 55]
(Compound 55)
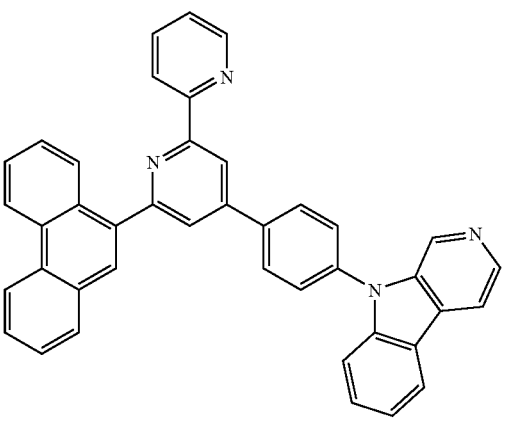

[Chem. 56]
(Compound 56)
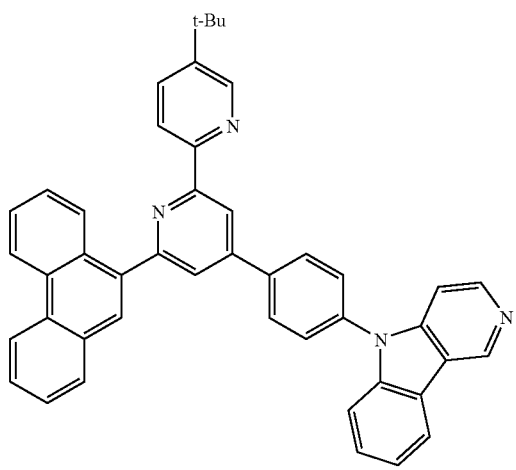
[Chem. 57]
(Compound 57)
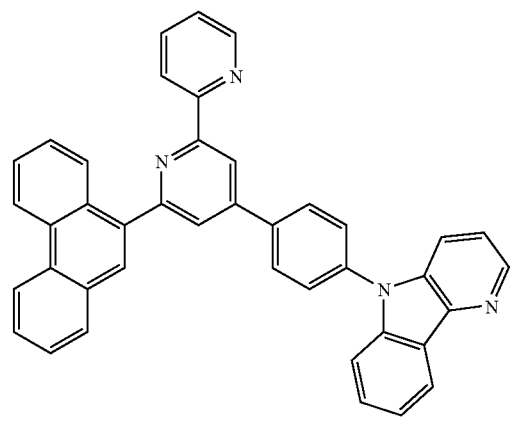
[Chem. 58]
(Compound 58)
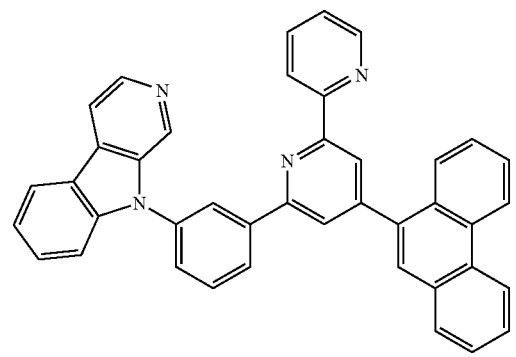
[Chem. 59]
(Compound 59)
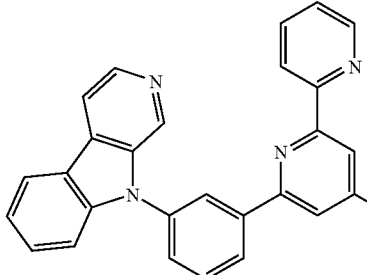
[Chem. 60]
(Compound 60)
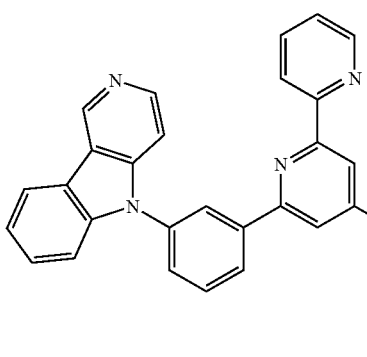
[Chem. 61]
(Compound 61)
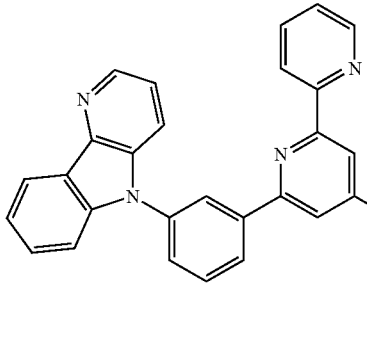
[Chem. 62]
(Compound 62)
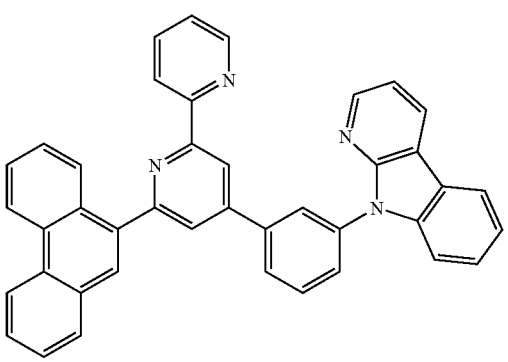

[Chem. 63]
(Compound 63)
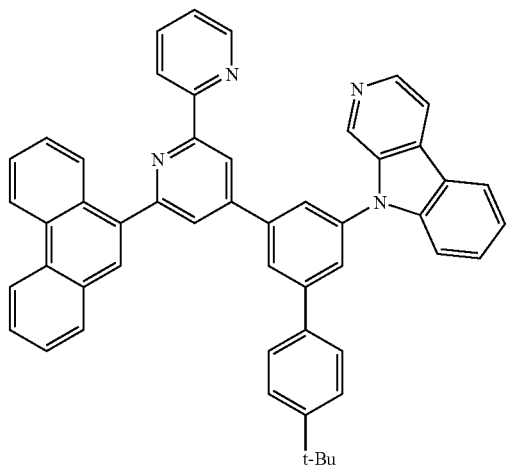
[Chem. 64]
(Compound 64)
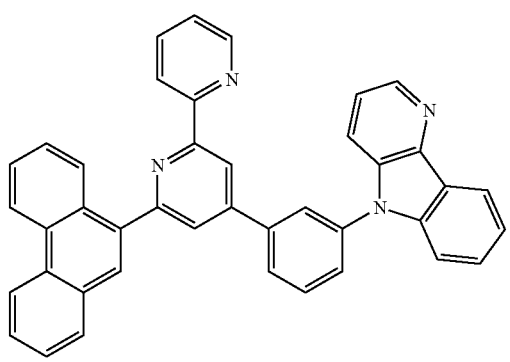
[Chem. 65]
(Compound 65)
[Chem. 66]
(Compound 66)
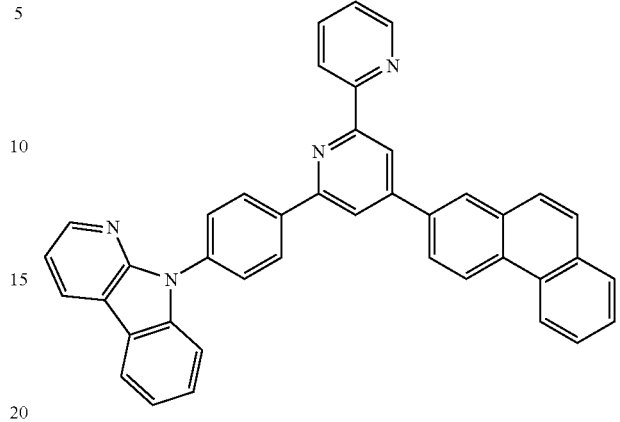
[Chem. 67]
(Compound 67)
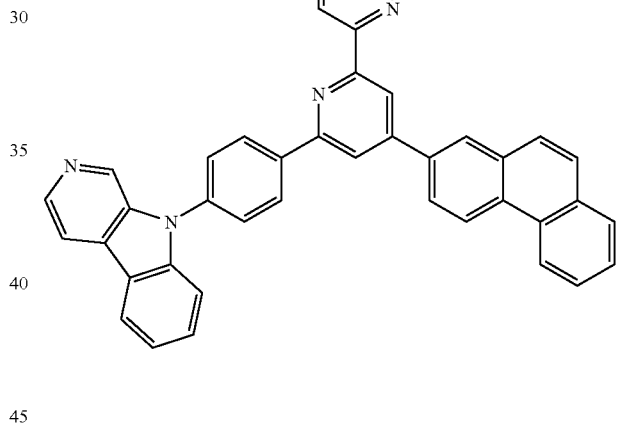
[Chem. 68]
(Compound 68)
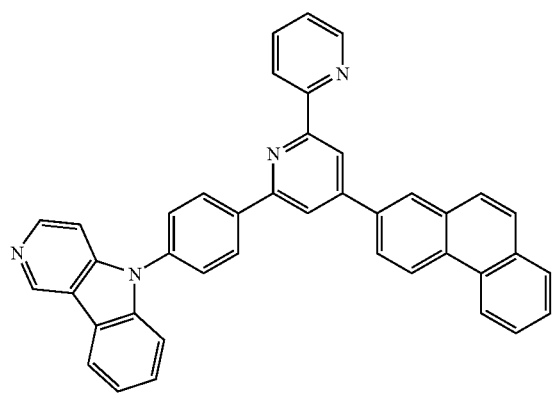

[Chem. 69]
(Compound 69)
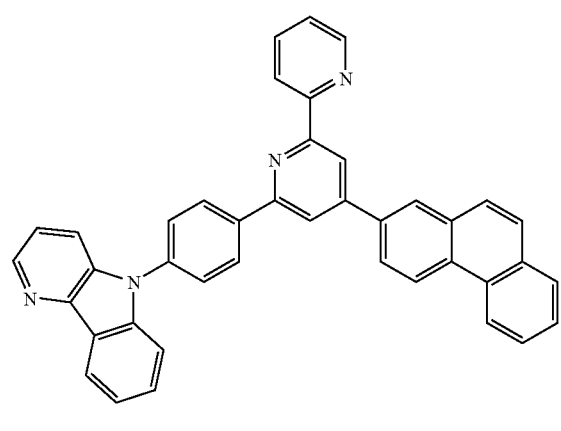
[Chem. 70]
(Compound 70)
[Chem. 71]
(Compound 71)
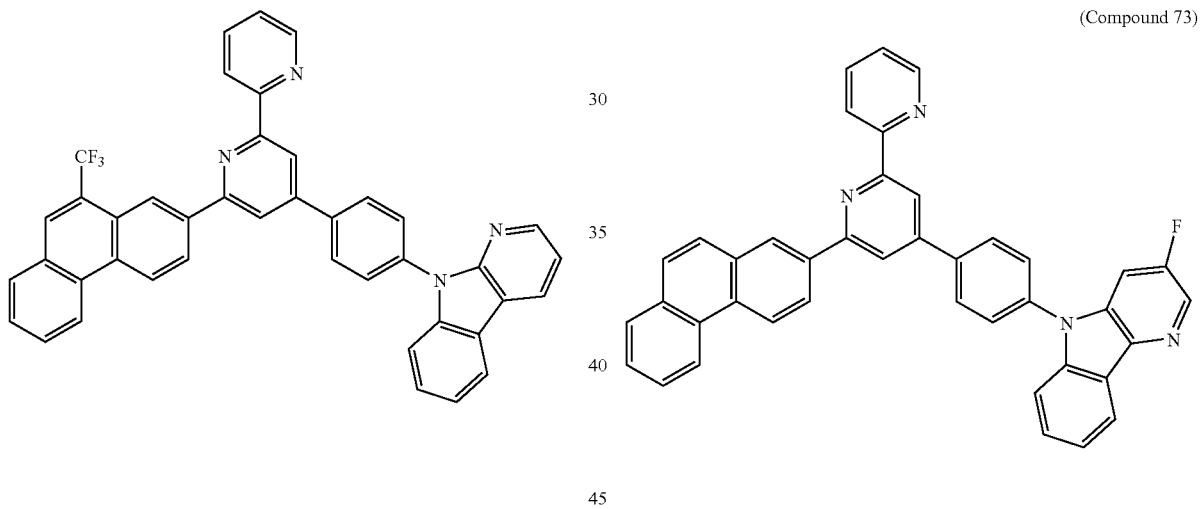
[Chem. 72]
(Compound 72)
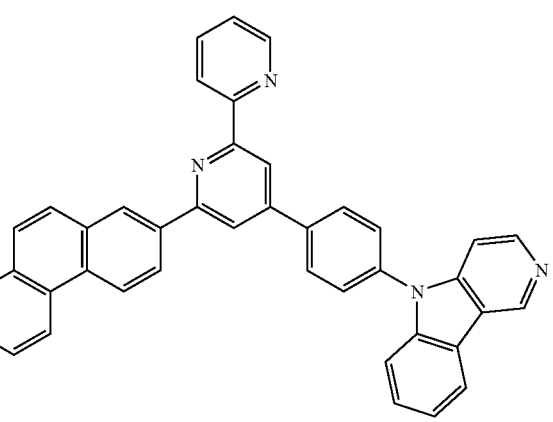
[Chem. 73]
(Compound 73)
[Chem. 74]
(Compound 74)
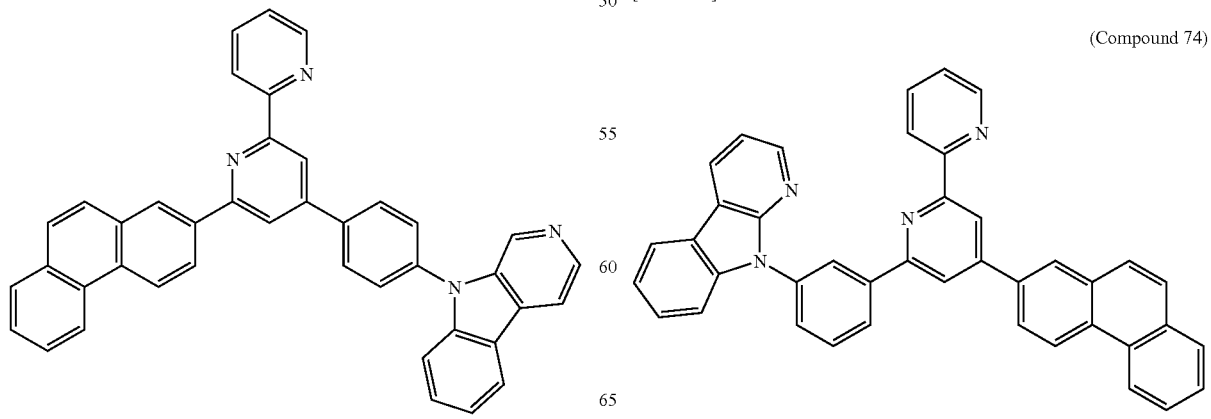

[Chem. 75]
(Compound 75)
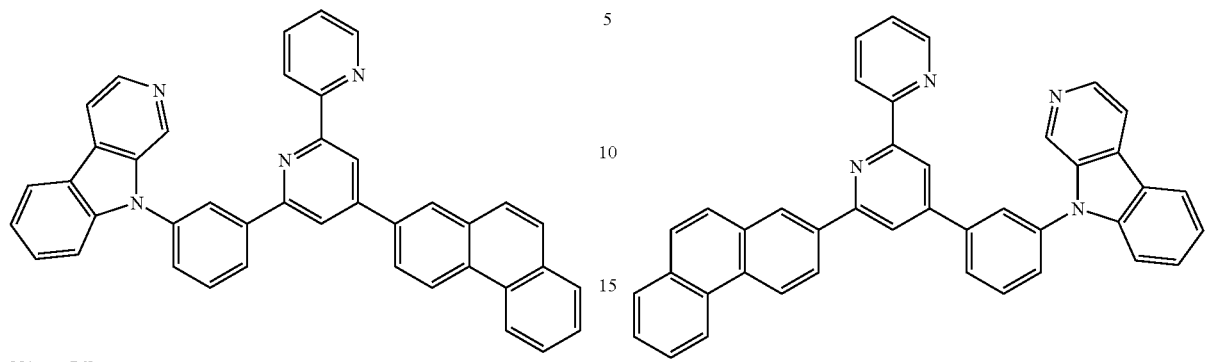
[Chem. 76]
(Compound 76)
[Chem. 77]
(Compound 77)
[Chem. 78]
(Compound 78)
[Chem. 79]
(Compound 79)
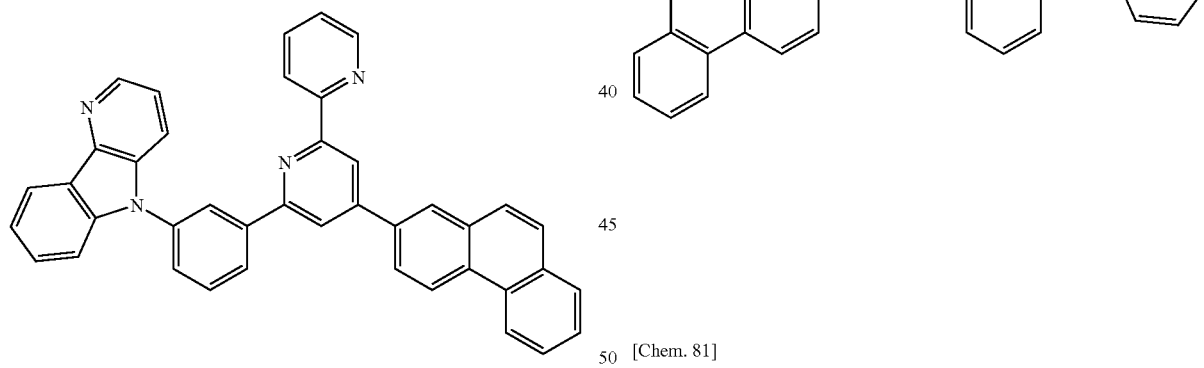
[Chem. 80]
(Compound 80)
[Chem. 81]
(Compound 81)
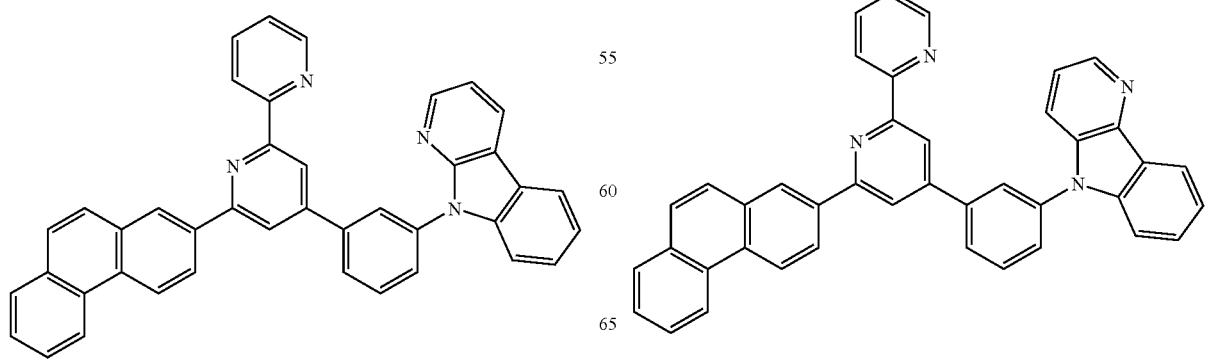

[Chem. 82]

(Compound 82)

[Chem. 83]

(Compound 83)

[Chem. 84]

(Compound 84)

[Chem. 85]

(Compound 85)

[Chem. 86]

(Compound 86)

[Chem. 87]

(Compound 87)

[Chem. 88]
(Compound 88)
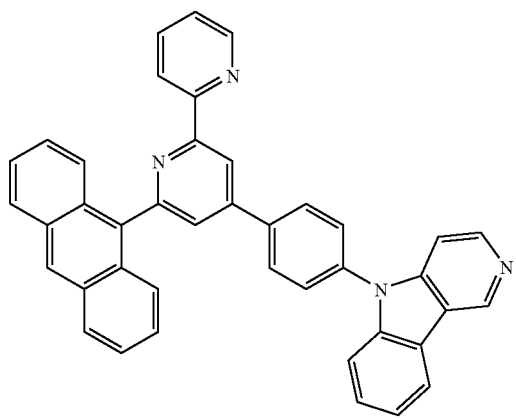
[Chem. 89]
(Compound 89)
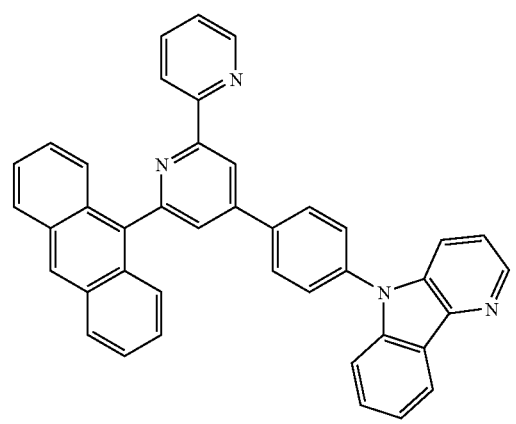
[Chem. 90]
(Compound 90)
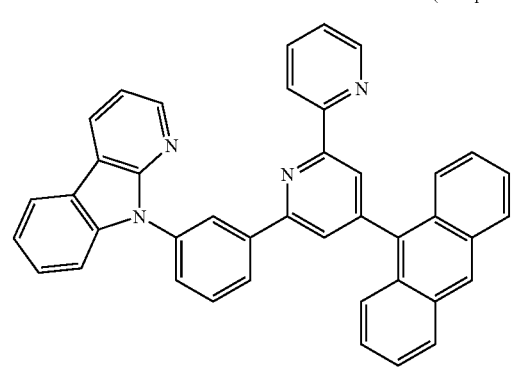
[Chem. 91]
(Compound 91)
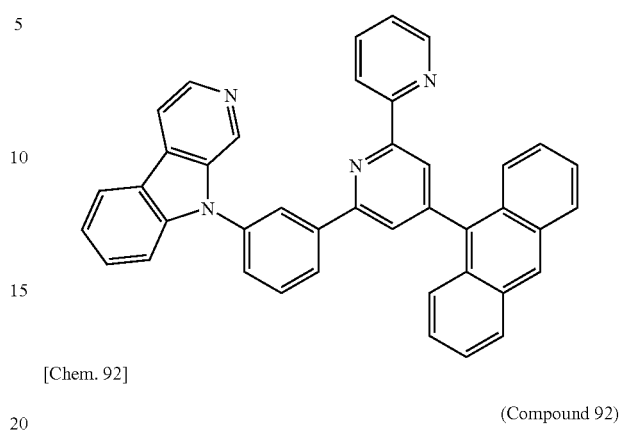
[Chem. 92]
(Compound 92)
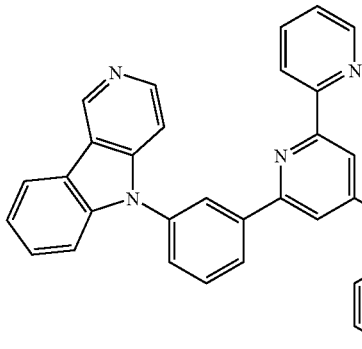
[Chem. 93]
(Compound 93)
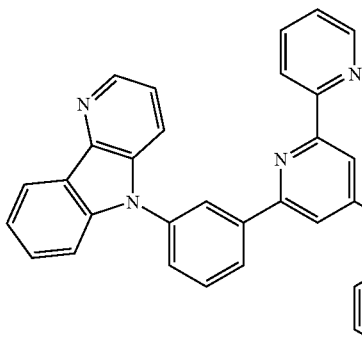
[Chem. 94]
(Compound 94)
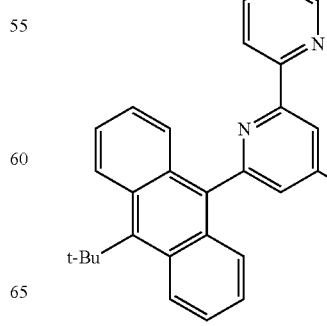

[Chem. 95]
(Compound 95)
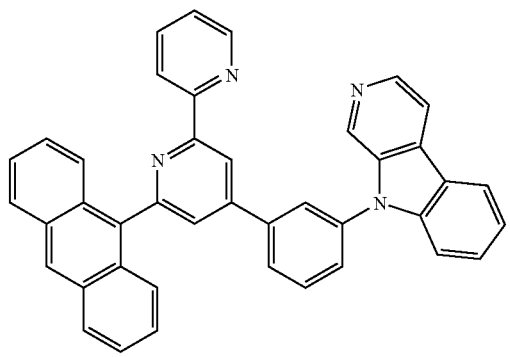
[Chem. 96]
(Compound 96)
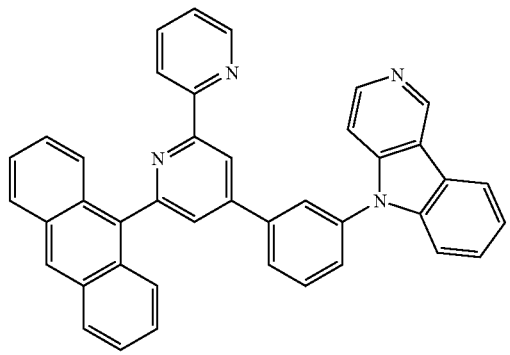
[Chem. 97]
(Compound 97)
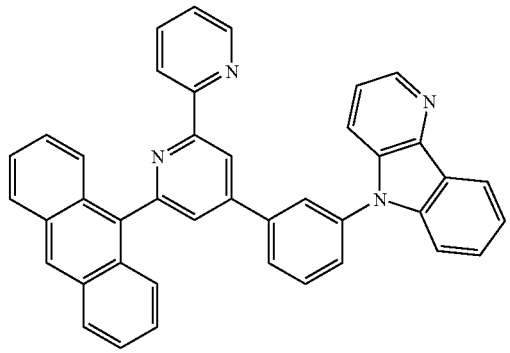
[Chem. 98]
(Compound 98)
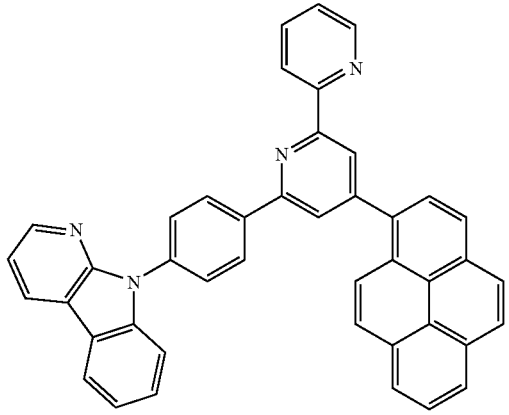
[Chem. 99]
(Compound 99)
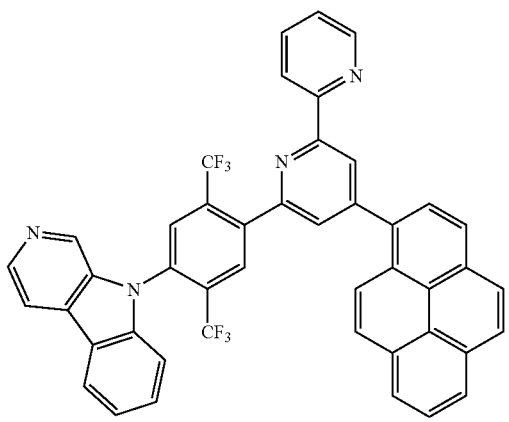
[Chem. 100]
(Compound 100)
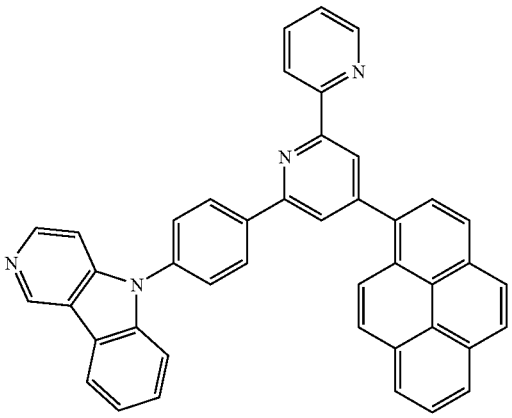

[Chem. 101]
(Compound 101)
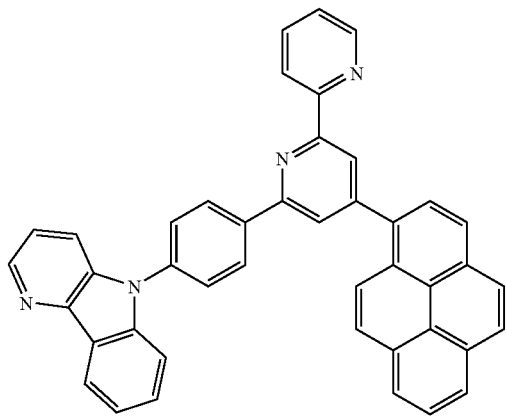
[Chem. 102]
(Compound 102)
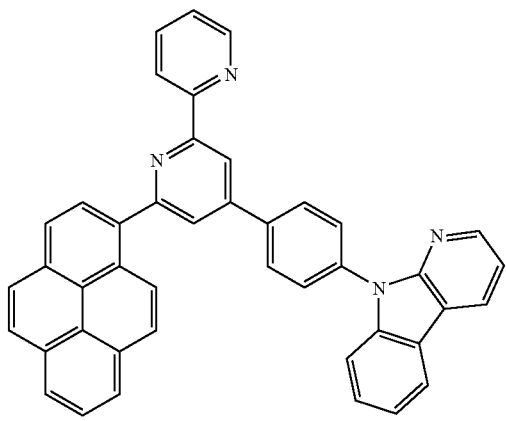
[Chem. 103]
(Compound 103)
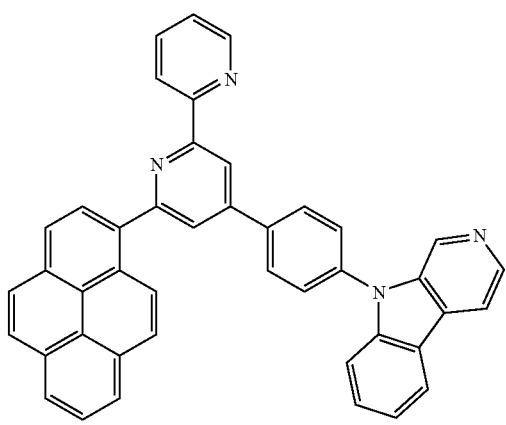
[Chem. 104]
(Compound 104)
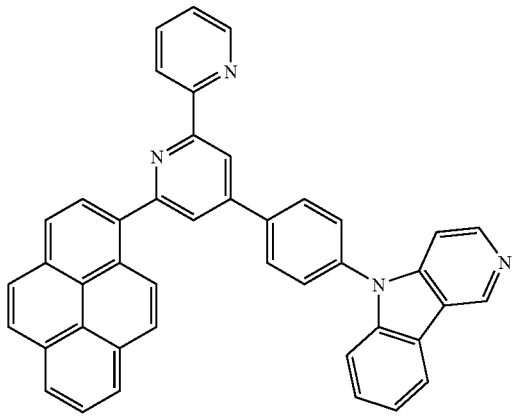
[Chem. 105]
(Compound 105)
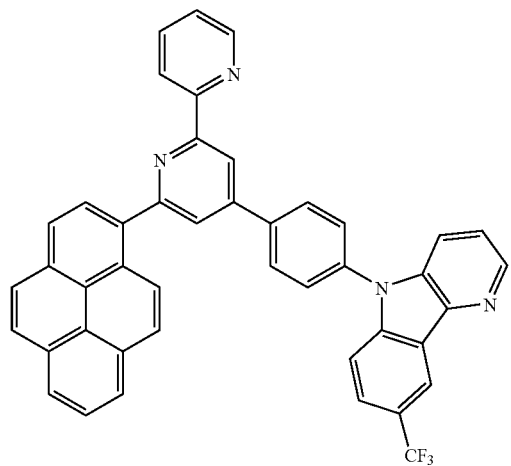
[Chem. 106]
(Compound 106)
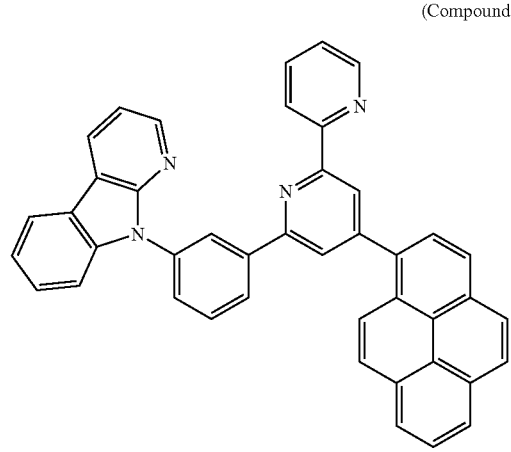

[Chem. 107]
(Compound 107)
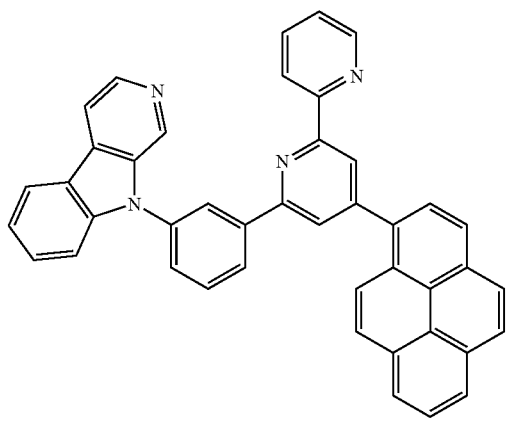
[Chem. 108]
(Compound 108)
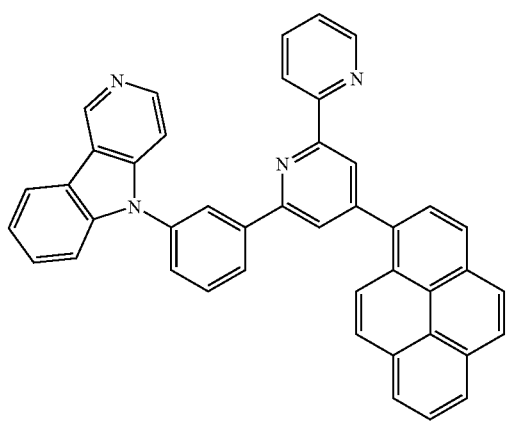
[Chem. 109]
(Compound 109)
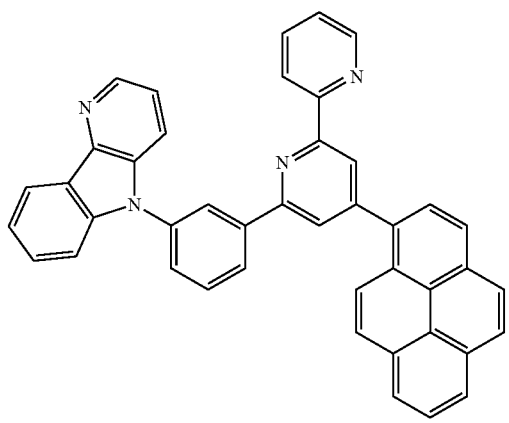
[Chem. 110]
(Compound 110)
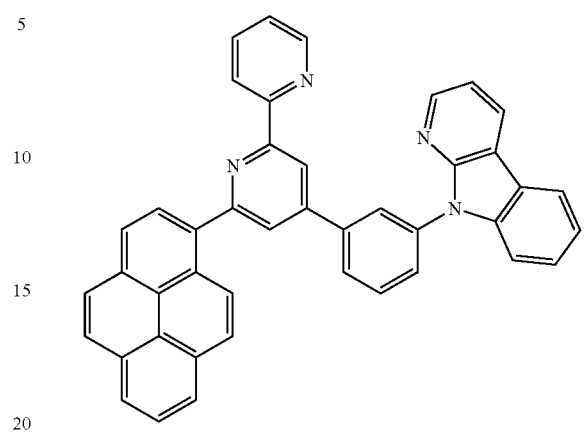
[Chem. 111]
(Compound 111)
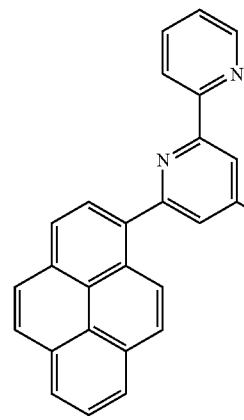
[Chem. 112]
(Compound 112)
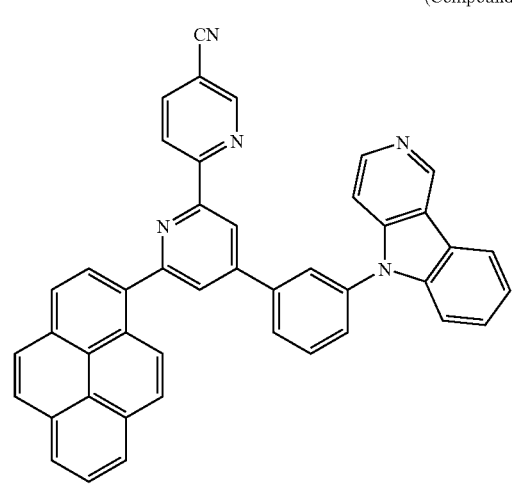

[Chem. 113]
(Compound 113)
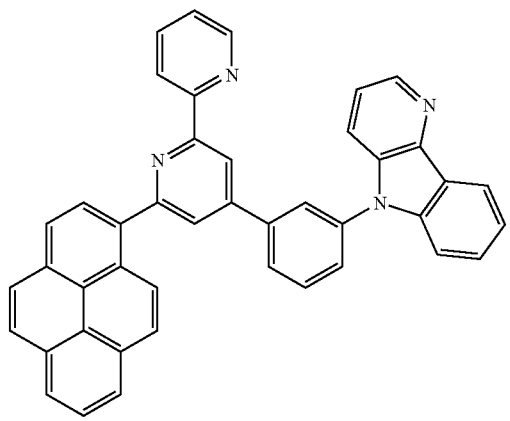
[Chem. 114]
(Compound 114)
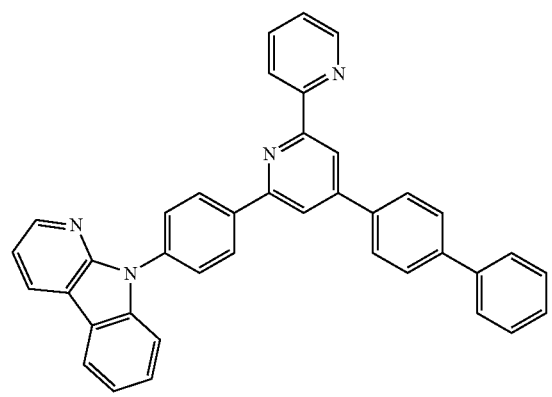
[Chem. 115]
(Compound 115)
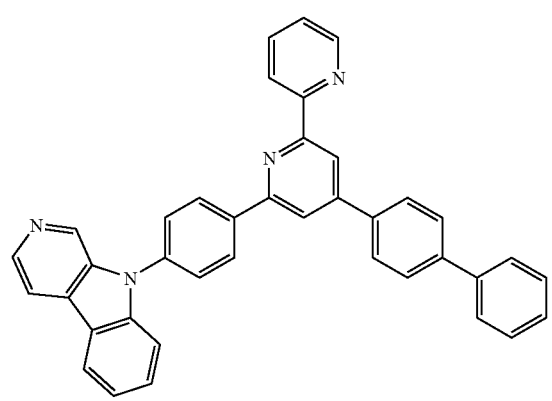
[Chem. 116]
(Compound 116)
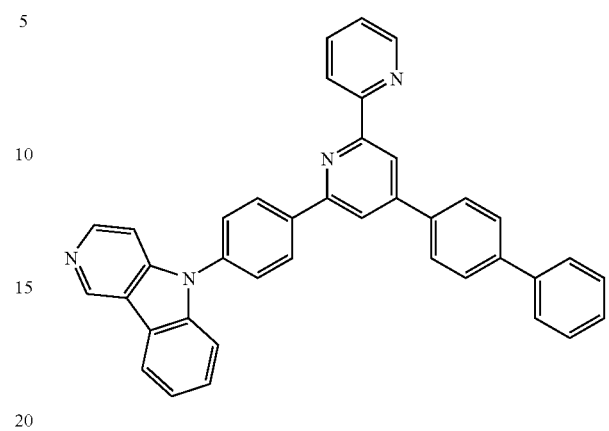
[Chem. 117]
(Compound 117)
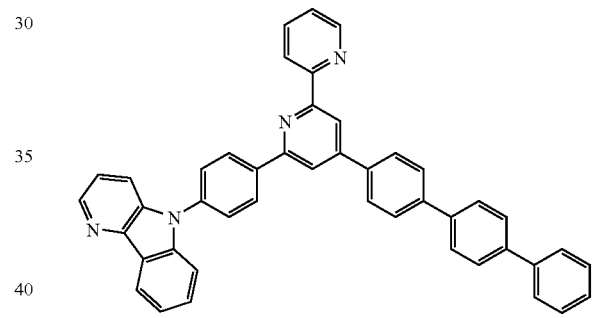
[Chem. 118]
(Compound 118)
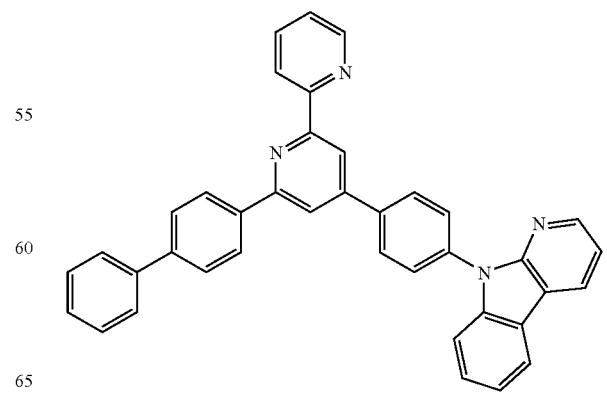

[Chem. 119]
(Compound 119)
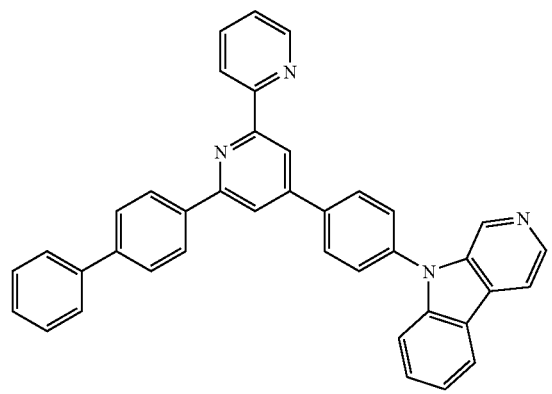
[Chem. 120]
(Compound 120)
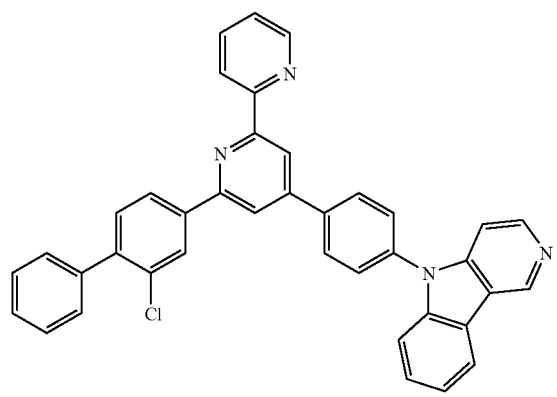
[Chem. 121]
(Compound 121)
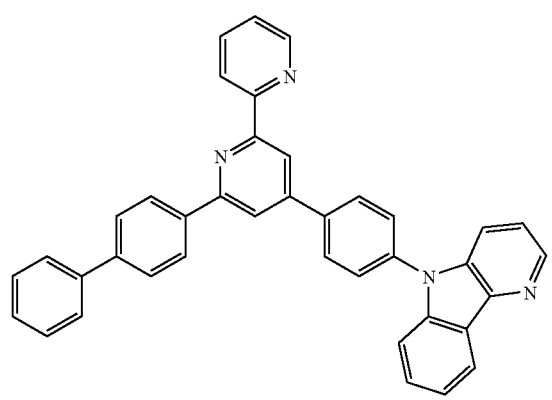
[Chem. 122]
(Compound 122)
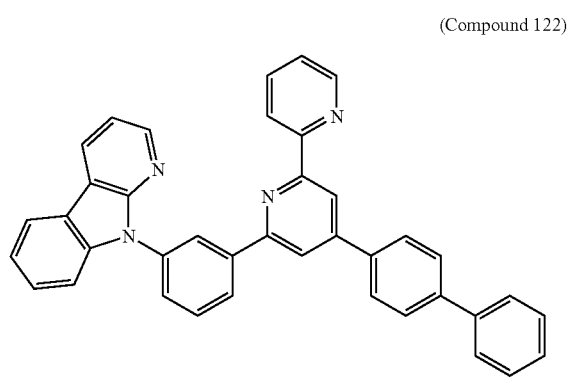
[Chem. 123]
(Compound 123)
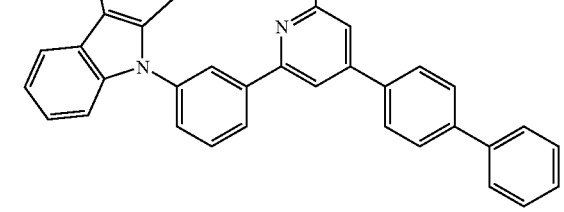
[Chem. 124]
(Compound 124)
[Chem. 125]
(Compound 125)
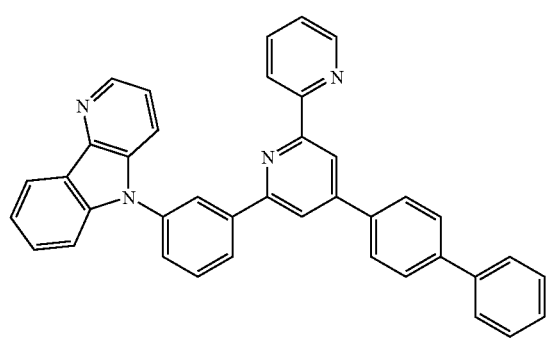

[Chem. 126]
(Compound 126)
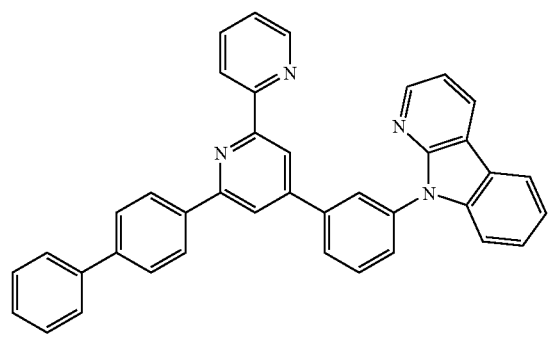
[Chem. 127]
(Compound 127)
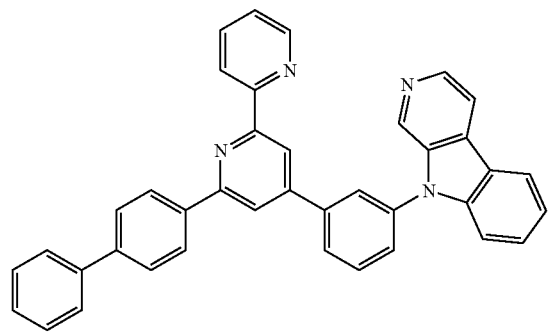
[Chem. 128]
(Compound 128)
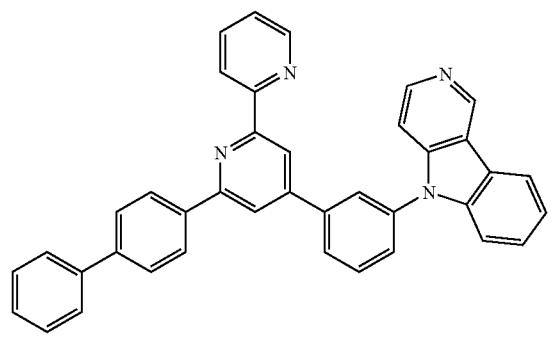
[Chem. 129]
(Compound 129)
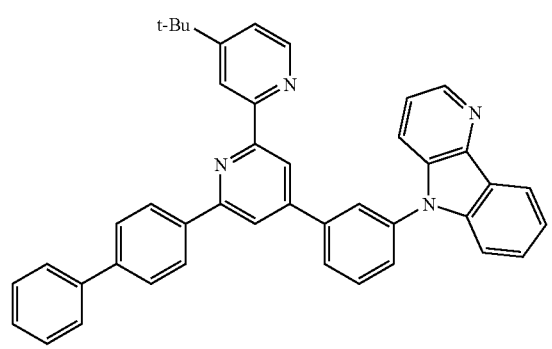
[Chem. 130]
(Compound 130)
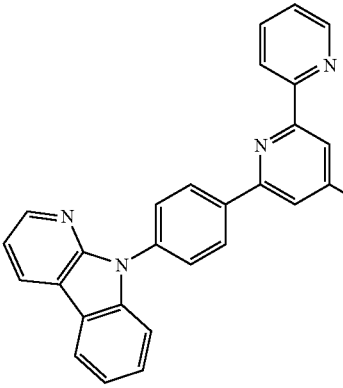
[Chem. 131]
(Compound 131)
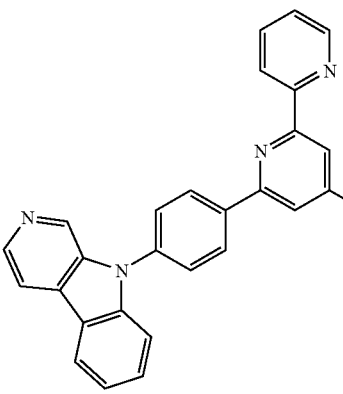
[Chem. 132]
(Compound 132)
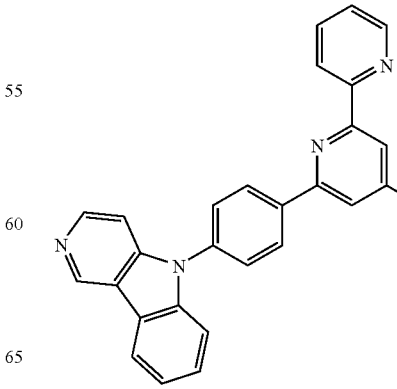

[Chem. 133]
(Compound 133)
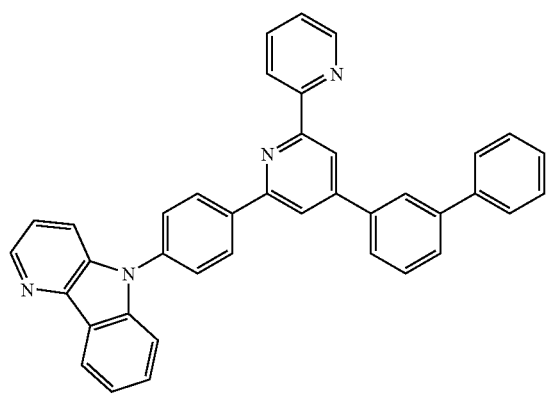
[Chem. 134]
(Compound 134)
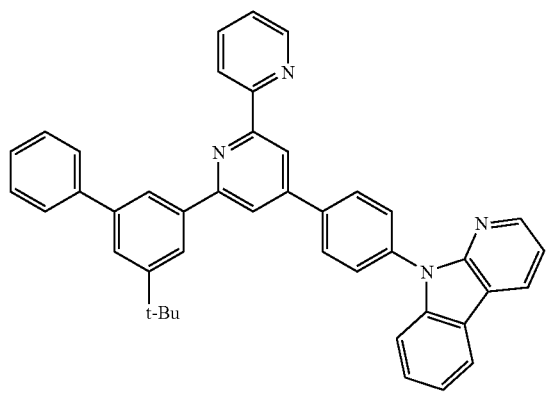
[Chem. 135]
(Compound 135)
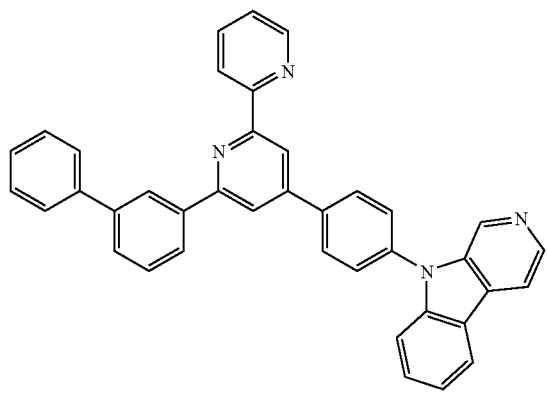
[Chem. 136]
(Compound 136)
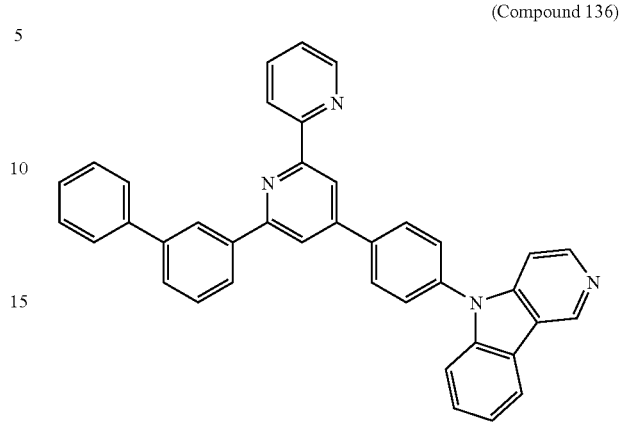
[Chem. 137]
(Compound 137)
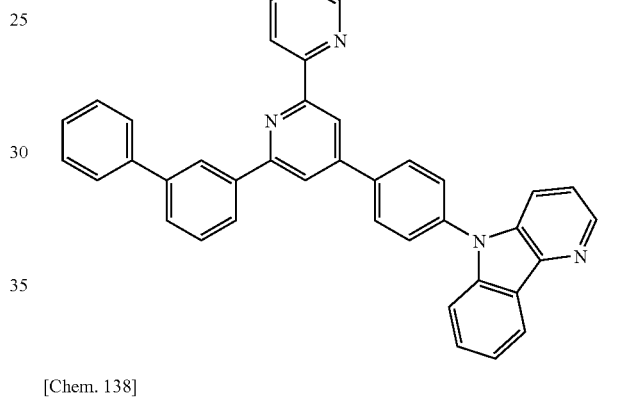
[Chem. 138]
(Compound 138)
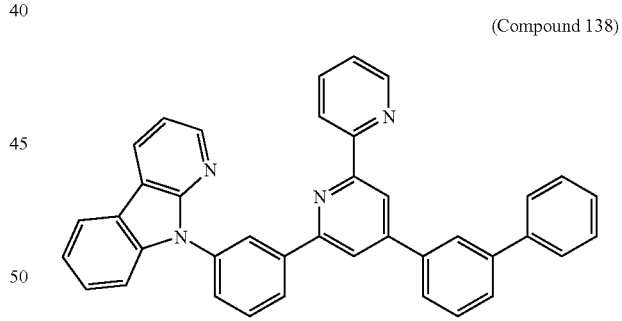
[Chem. 139]
(Compound 139)
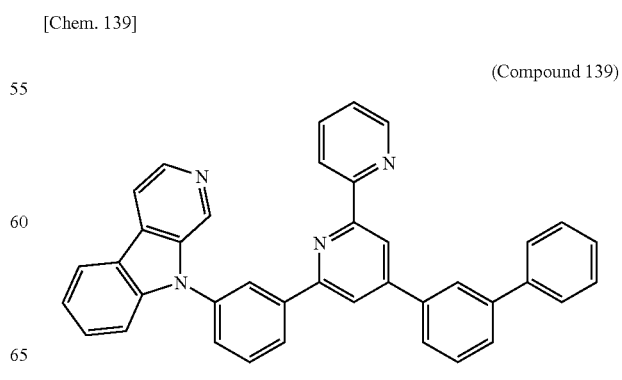

[Chem. 140]
(Compound 140)
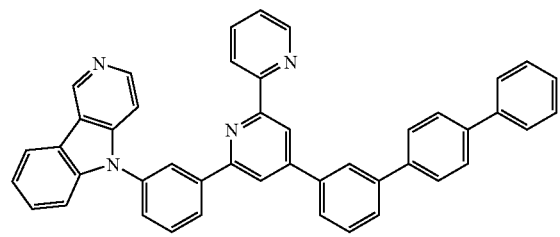
[Chem. 141]
(Compound 141)
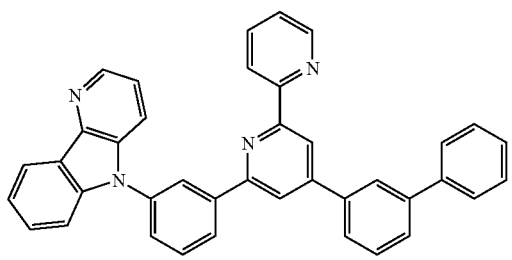
[Chem. 142]
(Compound 142)
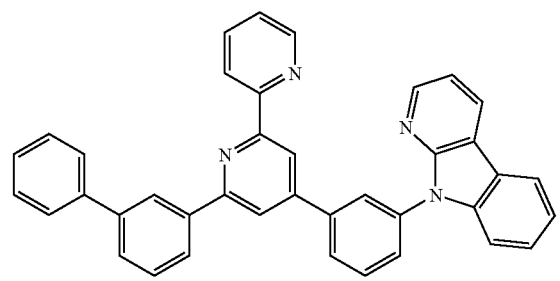
[Chem. 143]
(Compound 143)
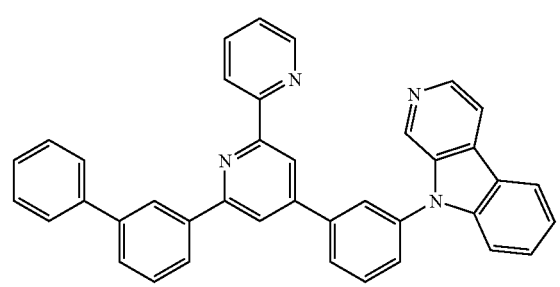
[Chem. 144]
(Compound 144)
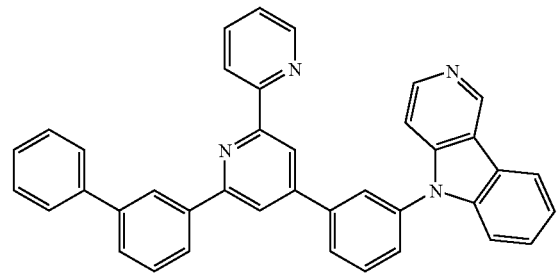
[Chem. 145]
(Compound 145)
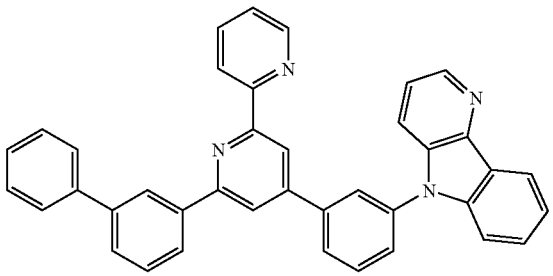
[Chem. 146]
(Compound 146)
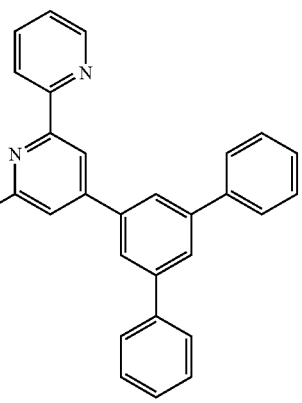
[Chem. 147]
(Compound 147)
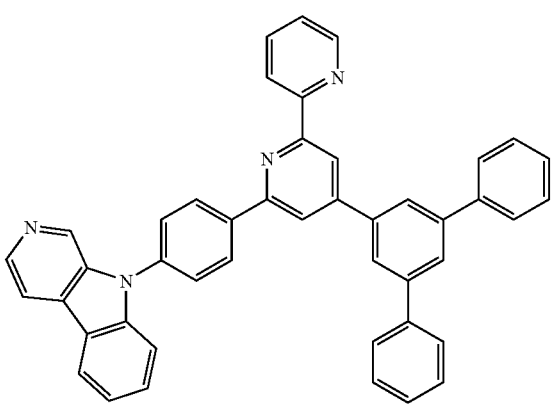

[Chem. 148]

(Compound 148)

[Chem. 149]

(Compound 149)

[Chem. 150]

(Compound 150)

[Chem. 151]

(Compound 151)

[Chem. 152]

(Compound 152)

[Chem. 153]

(Compound 153)

[Chem. 154]
(Compound 154)
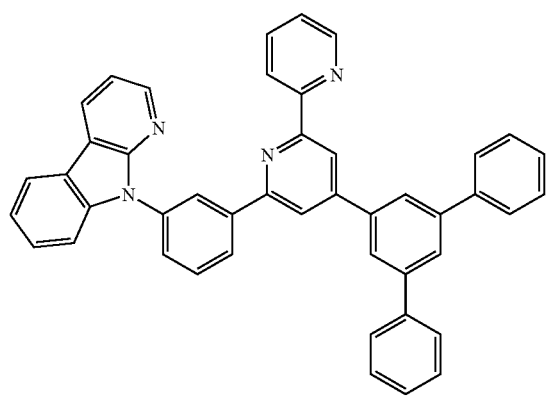
[Chem. 155]
(Compound 155)
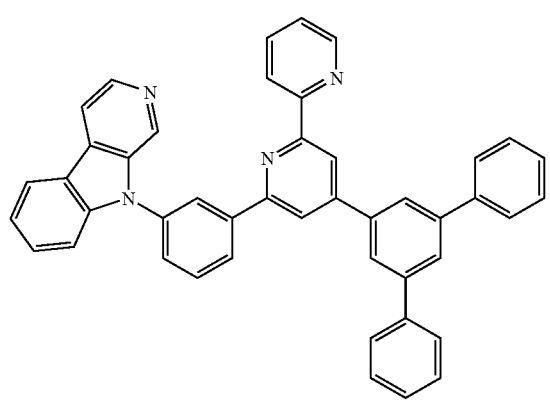
[Chem. 156]
(Compound 156)
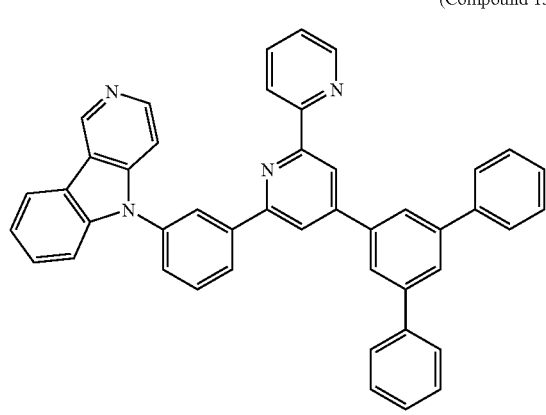
[Chem. 157]
(Compound 157)
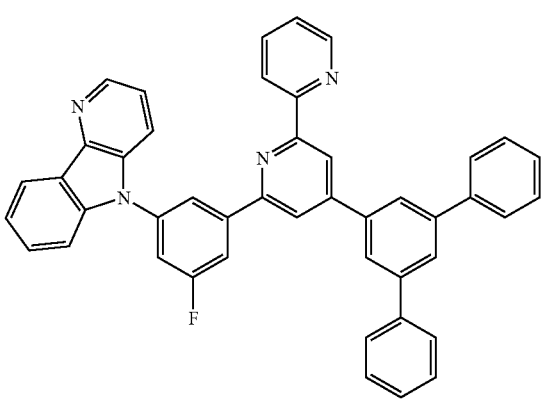
[Chem. 158]
(Compound 158)
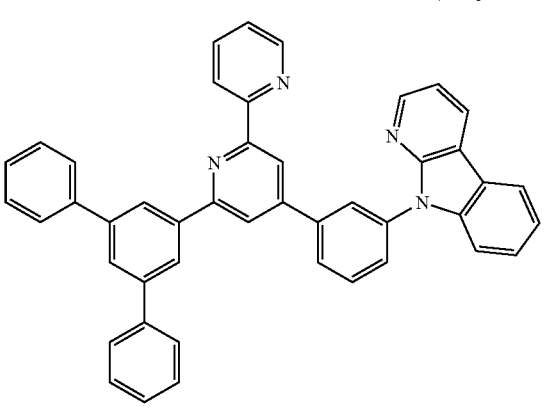
[Chem. 159]
(Compound 159)
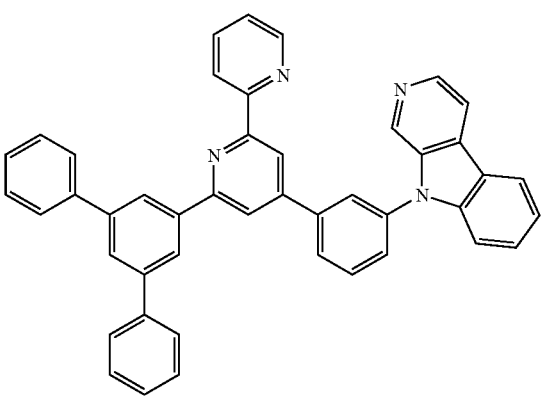

[Chem. 160]
(Compound 160)
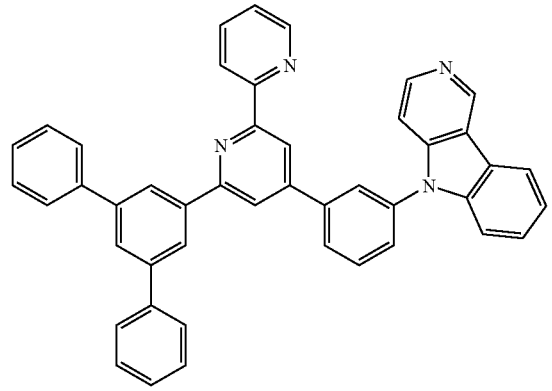
[Chem. 161]
(Compound 161)
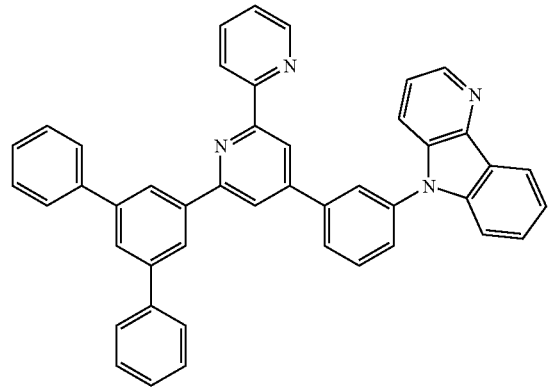
[Chem. 162]
(Compound 162)
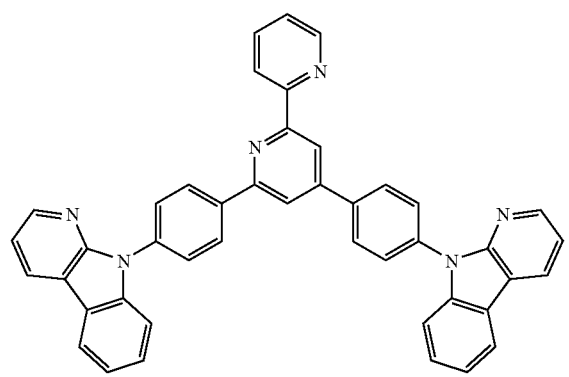
[Chem. 163]
(Compound 163)
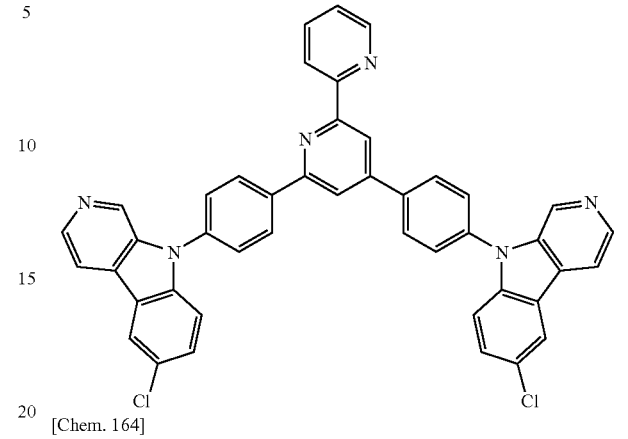
[Chem. 164]
(Compound 164)
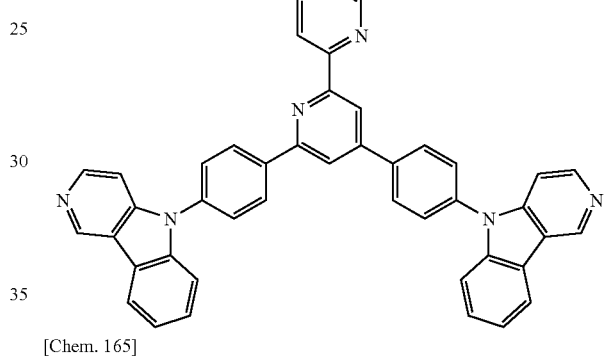
[Chem. 165]
(Compound 165)
[Chem. 166]
(Compound 166)

[Chem. 167]
(Compound 167)
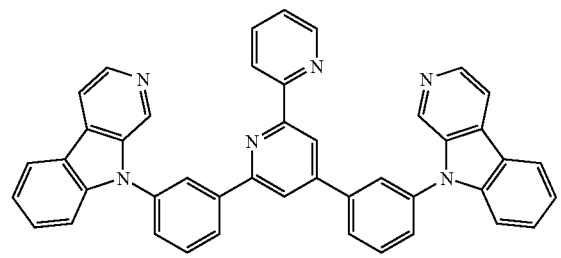
[Chem. 168]
(Compound 168)
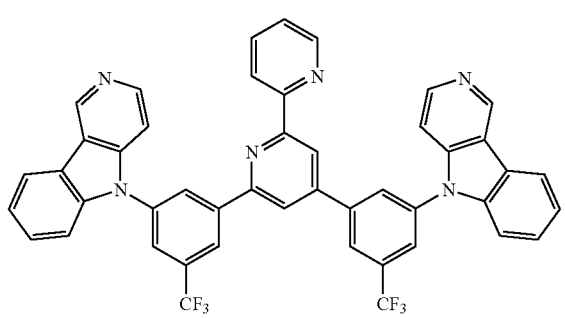
[Chem. 169]
(Compound 169)
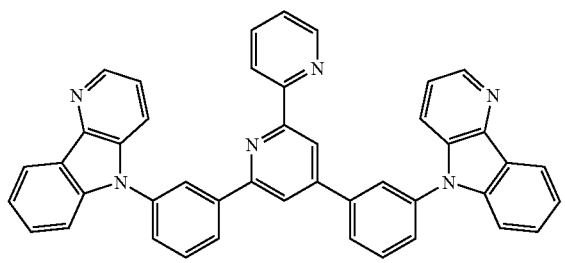
[Chem. 170]
(Compound 170)
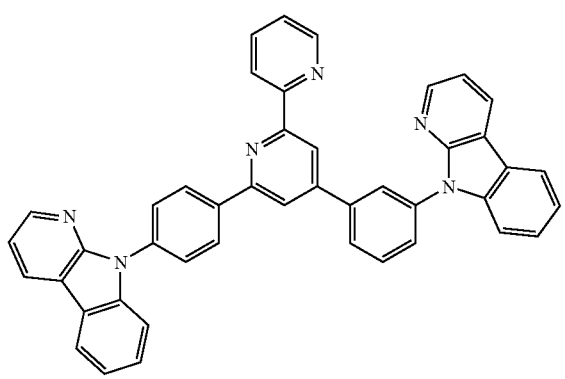
[Chem. 171]
(Compound 171)
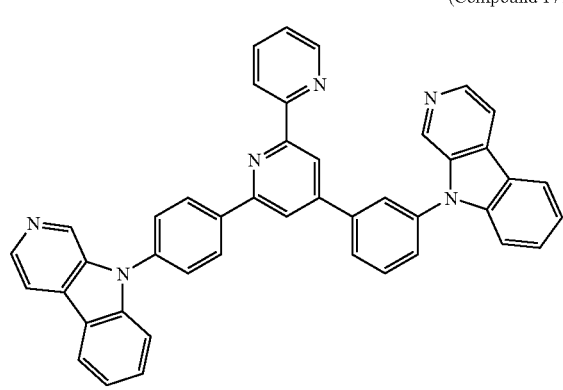
[Chem. 172]
(Compound 172)
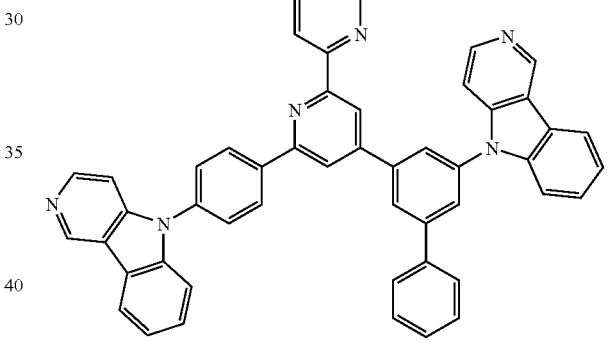
[Chem. 173]
(Compound 173)
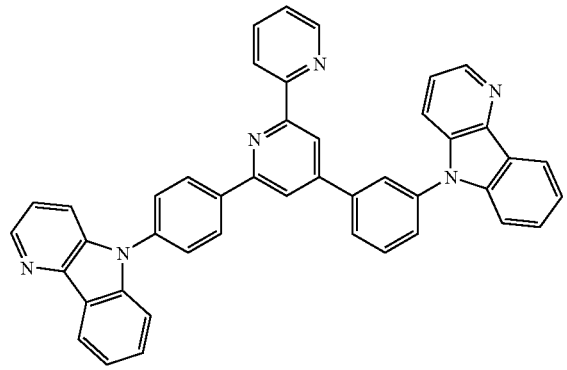

[Chem. 174]
(Compound 174)
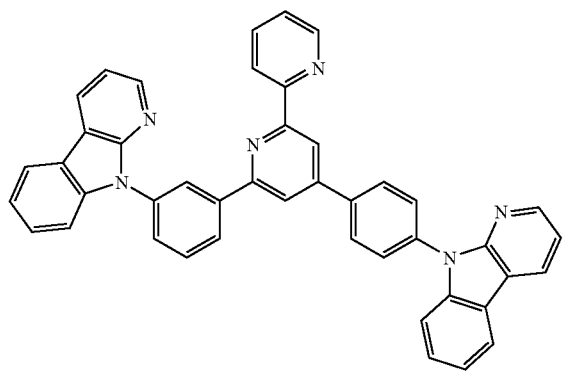
[Chem. 175]
(Compound 175)
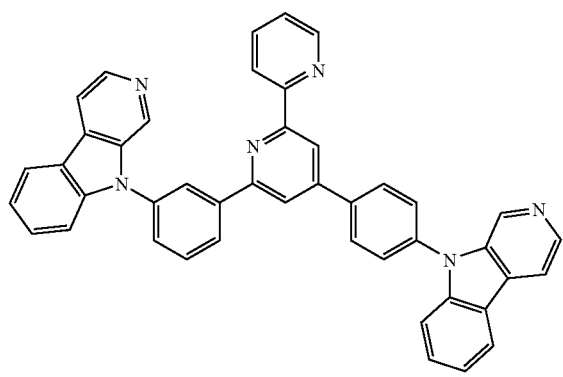
[Chem. 176]
(Compound 176)
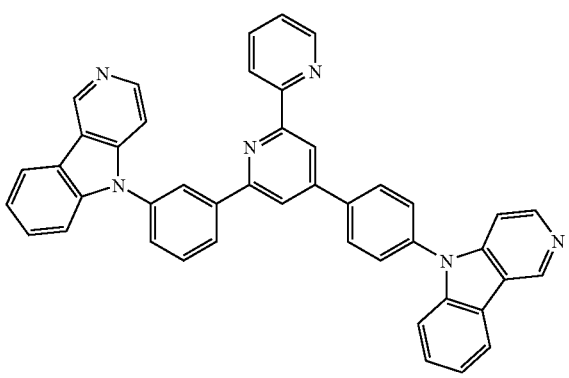
[Chem. 177]
(Compound 177)
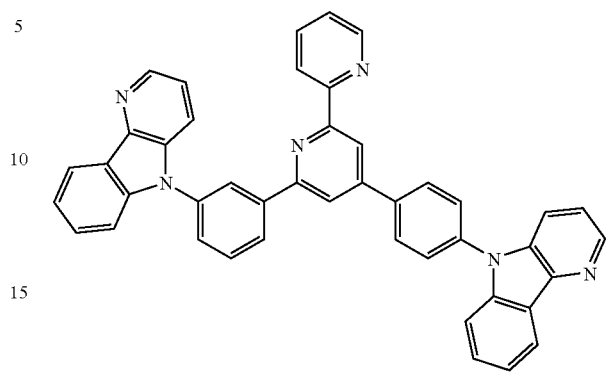
[Chem. 178]
(Compound 178)
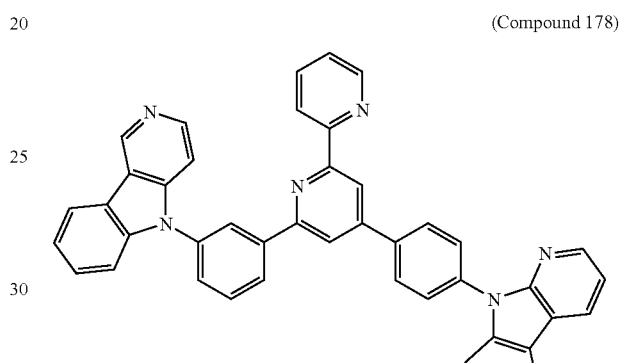
[Chem. 179]
(Compound 179)
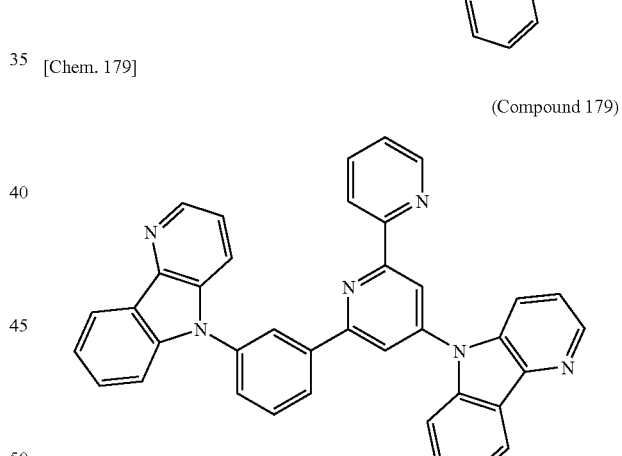
[Chem. 180]
(Compound 180)
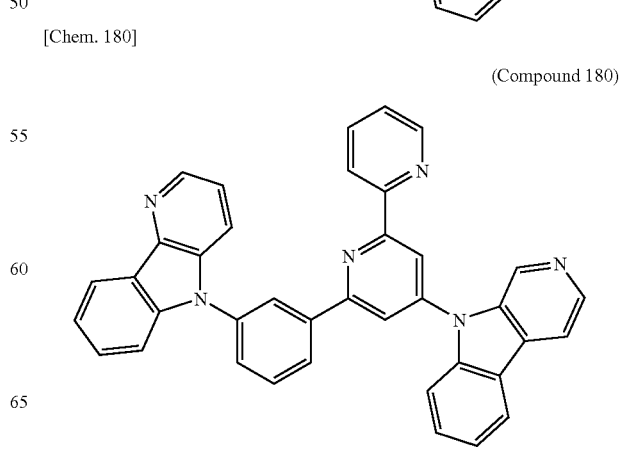

[Chem. 181]
(Compound 181)
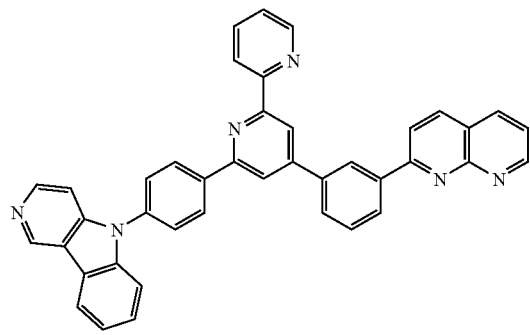
[Chem. 182]
(Compound 182)
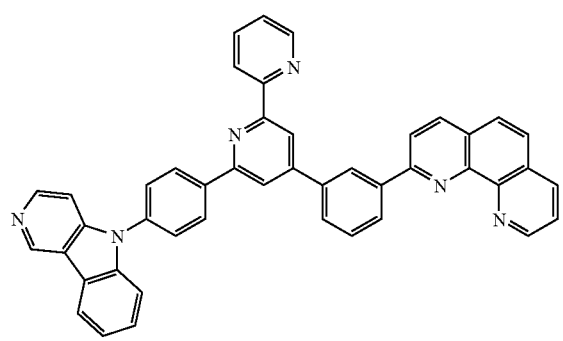
[Chem. 183]
(Compound 183)
[Chem. 184]
(Compound 184)
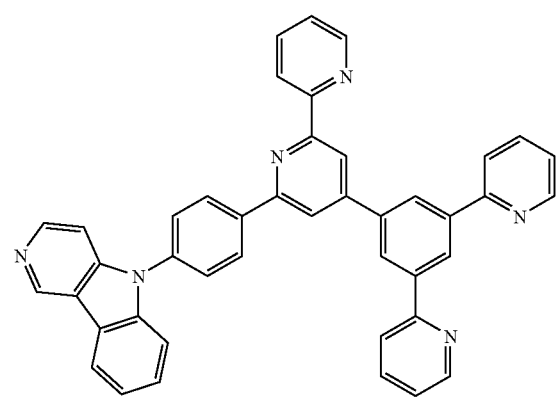
[Chem. 185]
(Compound 185)
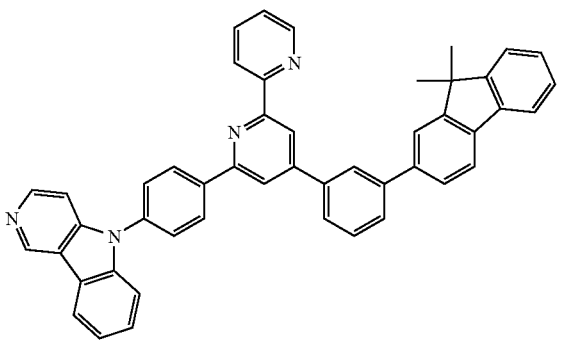
[Chem. 186]
(Compound 186)
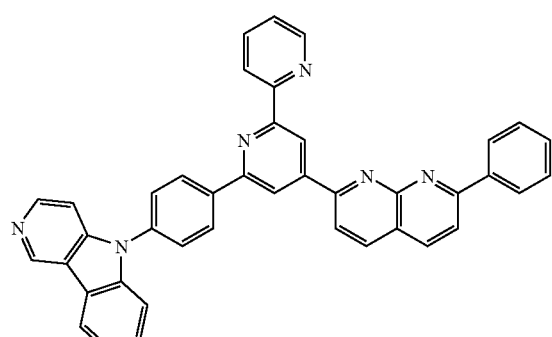
[Chem. 187]
(Compound 187)
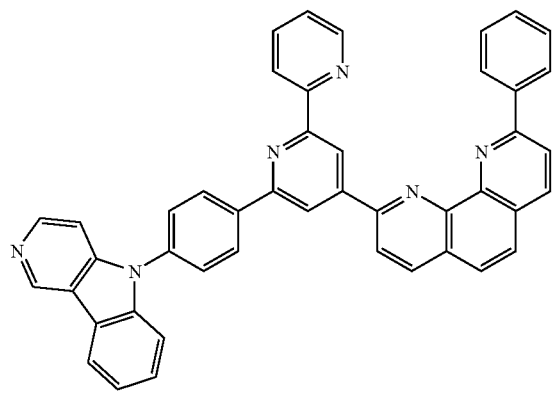

[Chem. 188]
(Compound 188)
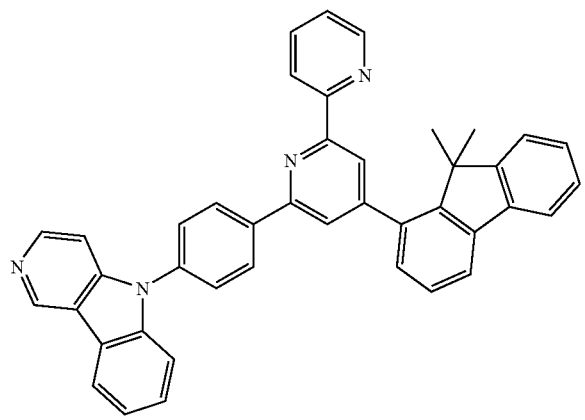
[Chem. 189]
(Compound 189)
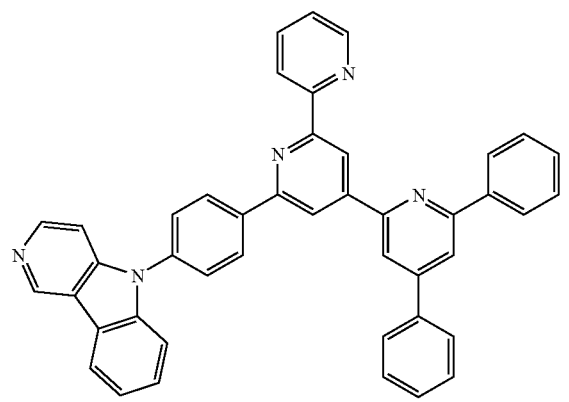
[Chem. 190]
(Compound 190)
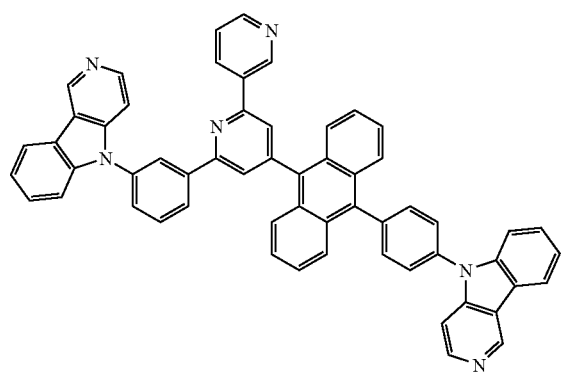
[Chem. 191]
(Compound 191)
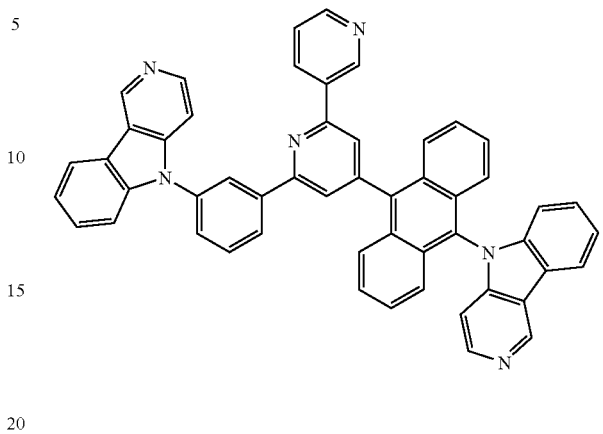
[Chem. 192]
(Compound 192)
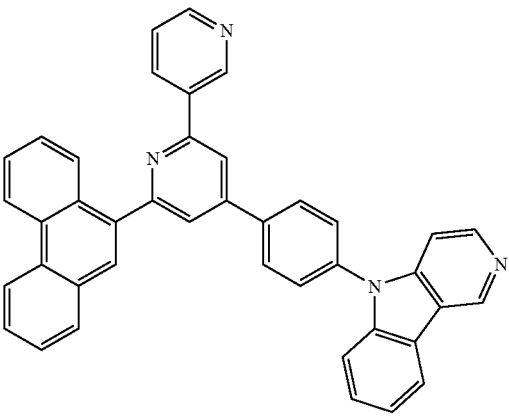
[Chem. 193]
(Compound 193)
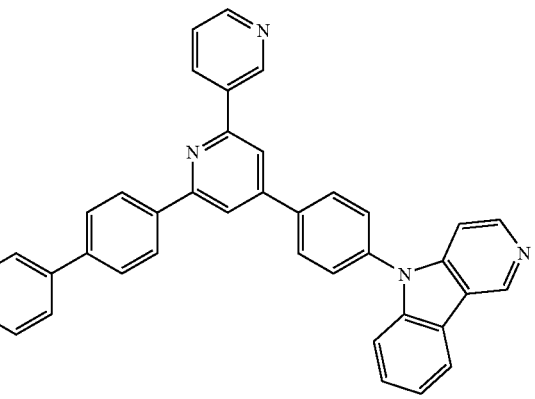

[Chem. 194]
(Compound 194)
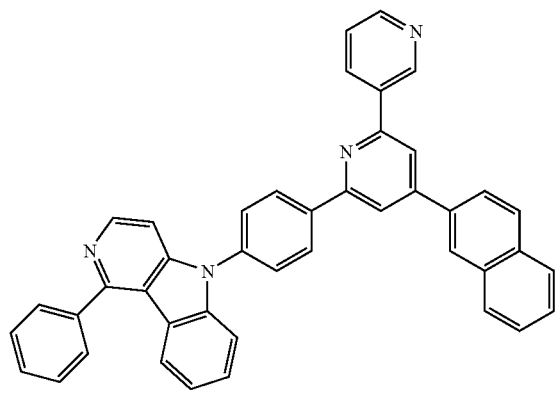
[Chem. 195]
(Compound 195)
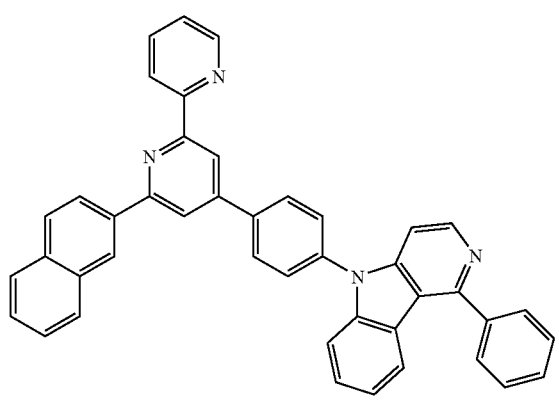
[Chem. 196]
(Compound 196)
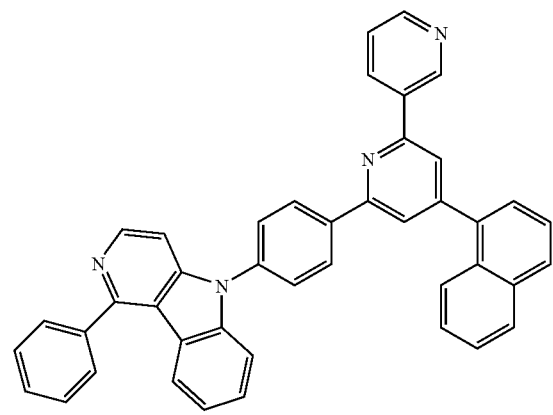
[Chem. 197]
(Compound 197)
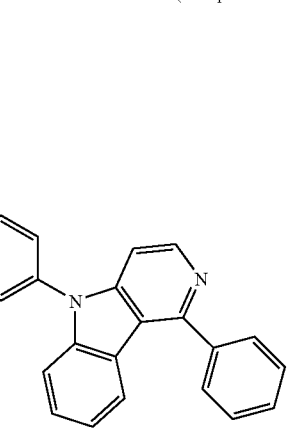
[Chem. 198]
(Compound 198)
[Chem. 199]
(Compound 199)
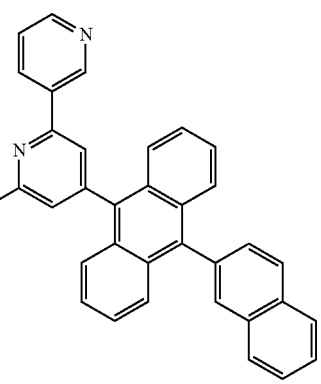

[Chem. 200]
(Compound 200)
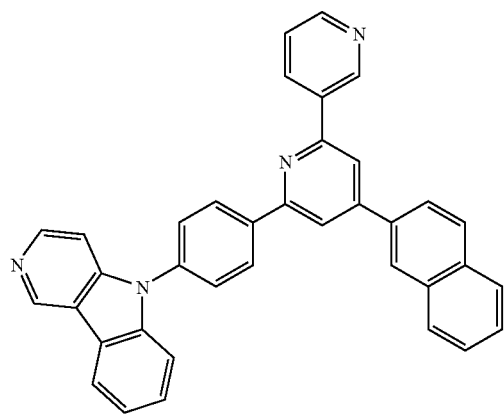
[Chem. 201]
(Compound 201)
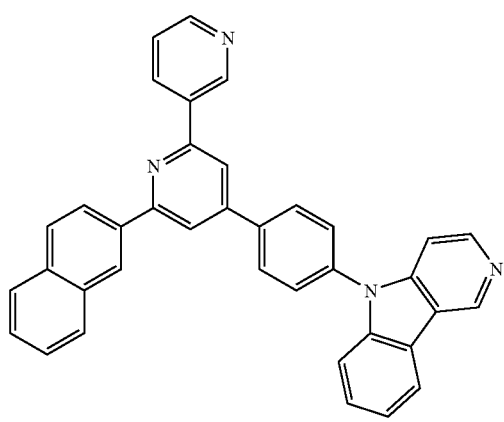
[Chem. 202]
(Compound 202)
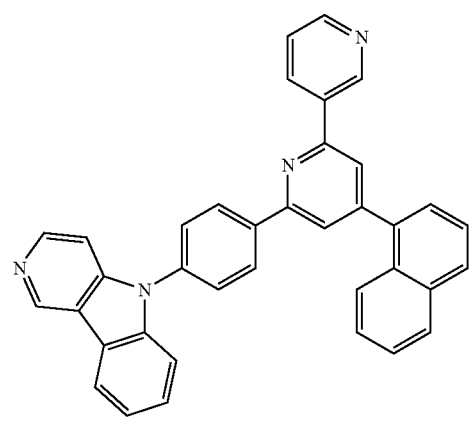
[Chem. 203]
(Compound 203)
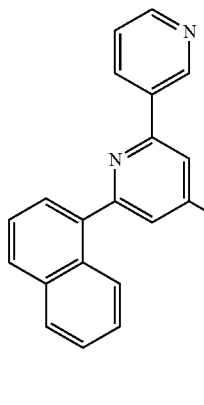
[Chem. 204]
(Compound 204)
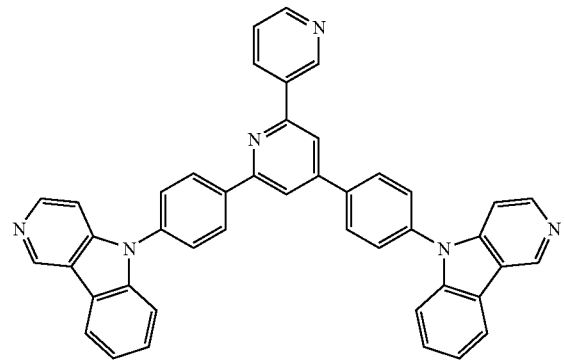
[Chem. 205]
(Compound 205)
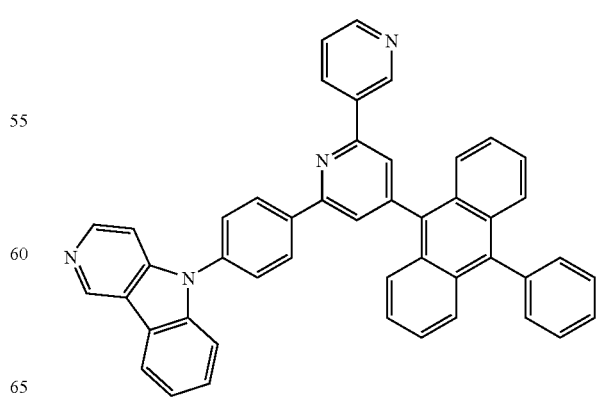

[Chem. 206]

(Compound 206)

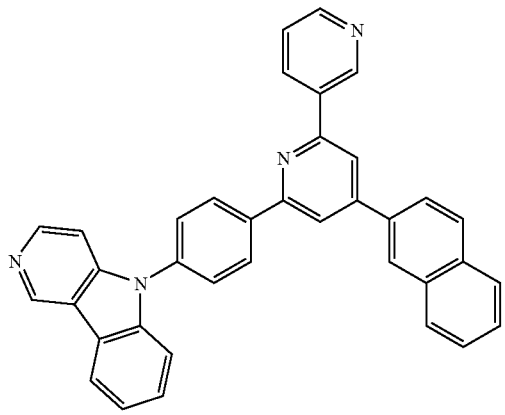

[Chem. 207]

(Compound 207)

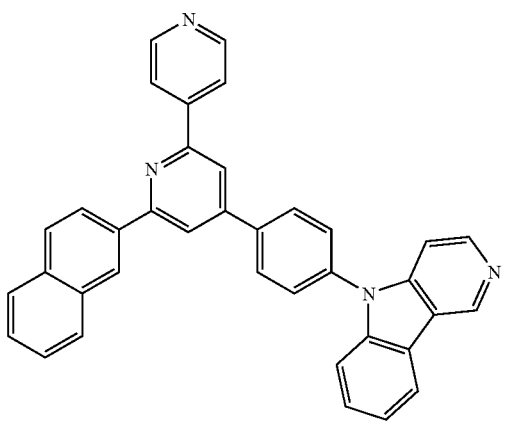

[Chem. 208]

(Compound 208)

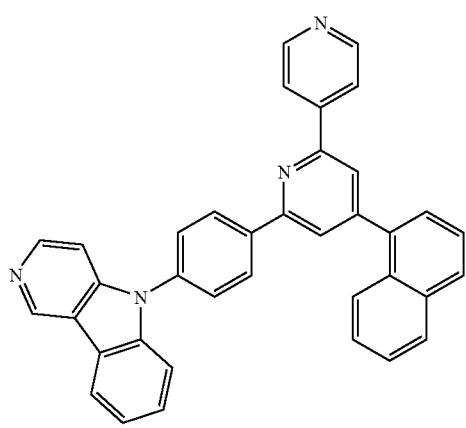

[Chem. 209]

(Compound 209)

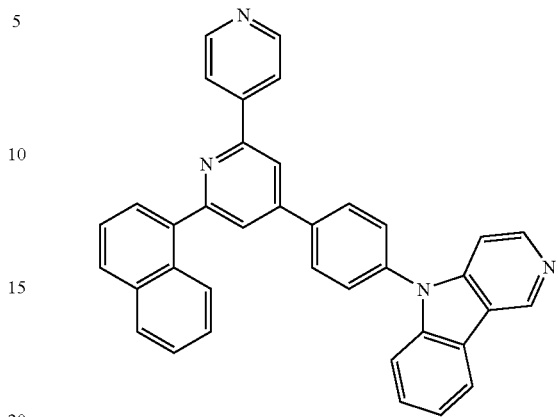

[Chem. 210]

(Compound 210)

Purification of these compounds was performed by purification by column chromatography, adsorption purification, a recrystallization or crystallization method with a solvent, or the like. Identification of the compounds can be performed by NMR analysis. As physical properties, DSC measurement (Tg) and measurement of melting point were performed. The melting point serves as an index of vapor deposition properties and the glass transition point (Tg) serves as an index of stability in a thin-film state.

The melting point and the glass transition point were measured using a powder material by means of a highly sensitive differential scanning calorimeter DSC 31005 manufactured by Bruker AXS.

Further, the work function was measured by preparing a thin film of 100 nm on an ITO substrate and using a photoelectron spectroscopy in air (Model AC-3, manufactured by Riken Keiki Co., Ltd.). The work function is regarded as an indicator of hole-blocking ability.

Examples of the structure of the organic EL device of the invention include a structure having an anode, a hole-injecting layer, a hole-transporting layer, an emitting layer, a hole-blocking layer, an electron-transporting layer and a cathode in this order on a substrate, and a structure further having an electron-injecting layer between the electron-transporting layer and the cathode. In these multilayer structures, it is possible to omit several layers of the organic layers and, for example, the structure may have a constitution sequentially having an anode, a hole-transporting layer, an emitting layer, an electron-transporting layer and a cathode on a substrate.

As the anode of the organic EL device, an electrode material having a large work function, such as ITO or gold, is used. As the hole-injecting layer, besides copper phthalocyanine (hereinafter referred to as CuPc), materials such as star-burst type triphenylamine derivatives and wet-process type materials may be employed.

For the hole-transporting layer, N,N'-diphenyl-N,N'-di(m-tolyl)-benzidine (hereinafter referred to as TPD) and N,N'-diphenyl-N,N'-di(α-naphthyl)-benzidine (hereinafter referred to as NPD), various triphenylamine tetramers, and the like may be used. Further, as the hole-injecting/transporting layers, wet-process type polymer materials such as PEDOT/PSS may be employed.

As the emitting layer, hole-blocking layer, and electron-transporting layer of the organic EL device of the invention, besides the compound having a substituted bipyridyl group and a pyridoindole ring structure connected with each other through a phenylene group, aluminum complexes, thiazole derivatives, oxazole derivatives, carbazole derivatives, polydialkylfluorene derivatives, and the like may be used.

By using a conventional luminescence material such as an aluminum complex or styryl derivative for the emitting layer and using the compound having a substituted bipyridyl group and a pyridoindole ring structure connected with each other through a phenylene group as the hole-blocking layer and the electron-transporting layer, a high-performance organic EL device can be prepared. Further, a high-performance organic EL device can be prepared also by adding a dopant, for example, a fluorescent material such as quinacridone, coumarin or rubrene or a phosphorescent material such as an iridium complex of phenylpyridine, as a host material of the emitting layer.

Furthermore, the compound having a substituted bipyridyl group and a pyridoindole ring structure connected with each other through a phenylene group can be used as the electron-transporting layer through multilayering or co-deposition with conventional electron-transporting material(s).

The organic EL device of the invention may have an electron-injecting layer. As the electron-injecting layer, lithium fluoride or the like may be used. For the cathode, an electrode material having a low work function such as aluminum, or an alloy having a low work function such as aluminum magnesium is used as an electrode material.

Embodiments of the invention will be illustrated in greater detail with reference to Examples, but the invention should not be construed as being limited to the following Examples so long as not exceeding the gist thereof.

Example 1

Synthesis of 6-[4-(5H-pyrido[4,3-b]indol-5-yl)phenyl]-4-(naphthalen-2-yl)-[2,2']bipyridine (Compound 36)

10.0 g of 4'-bromoacetophenone, 12.8 g of iodine, and 80 ml of pyridine were added and the whole was heated and stirred at 100° C. for 3 hours. After cooling to room temperature, 100 ml of water was added and purification by recrystallization was performed. Drying was performed under reduced pressure at 70° C. for 12 hours to obtain 15.5 g (yield 76%) of 4-bromophenacylpyridinium iodide as a brown powder.

Subsequently, 6.0 g of 2-naphthoaldehyde, 4.7 g of 2-acetylpyridine, and 40 ml of methanol were added and the whole was cooled to −5° C. under stirring. 62 ml of a 3 wt % NaOH/methanol solution was added dropwise thereto and the whole was stirred at −5° C. for 2 hours. Then, the reaction was further carried out at the same temperature for 2 days. 37.0 g of ammonium acetate, 15.5 g of the above 4-bromophenacylpyridinium iodide, and 100 ml of methanol were added to the reaction solution and the whole was stirred at 55° C. for 2 days. After cooling to room temperature, the resulting crude product was collected by filtration, washed with methanol, and then dried under reduced pressure at 70° C. for 12 hours to obtain 3.8 g (yield 23%) of 6-(4-bromophenyl)-4-(naphthalen-2-yl)-[2,2']bipyridine as a gray powder.

2.5 g of the resulting 6-(4-bromophenyl)-4-(naphthalen-2-yl)-[2,2']bipyridine, 1.0 g of 5H-pyrido[4,3-b]indole, 0.2 g of copper powder, 2.4 g of potassium carbonate, 0.2 ml of dimethyl sulfoxide, and 10 ml of n-dodecane were added and the whole was stirred for 7 hours under heating and refluxing. After cooling to room temperature, 60 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 1.85 g (yield 62%) of 6-[4-(5H-pyrido[4,3-b]indol-5-yl)phenyl]-4-(naphthalen-2-yl)-[2,2']bipyridine (Compound 36) as a white powder.

The structure of the resulting white powder was identified using NMR. The results of 1H-NMR measurement are shown in FIG. 1.

The following 24 hydrogen signals were detected on 1H-NMR (CDCl$_3$). δ (ppm)=9.42 (1H), 8.85 (1H), 8.76 (2H), 8.49-8.57 (3H), 8.36 (1H), 8.20-8.25 (2H), 7.90-8.03 (5H), 7.73 (2H), 7.51-7.58 (4H), 7.38-7.42 (3H).

Example 2

Synthesis of 4-[4-(5H-pyrido[4,3-b]indol-5-yl)phenyl]-6-(naphthalen-2-yl)-[2,2']bipyridine (Compound 40)

4-(4-Bromophenyl)-6-(naphthalen-2-yl)-[2,2']bipyridine was synthesized in the same manner as in the above Example 1. 2.5 g of the resulting 4-(4-bromophenyl)-6-(naphthalen-2-yl)-[2,2']bipyridine, 1.0 g of 5H-pyrido[4,3-b]indole, 0.2 g of copper powder, 2.4 g of potassium carbonate, 0.2 ml of dimethyl sulfoxide, and 10 ml of n-dodecane were added and the whole was stirred for 9 hours under heating and refluxing. After cooling to room temperature, 60 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 2.17 g (yield 72%) of 4-[4-(5H-pyrido[4,3-b]indol-5-yl)phenyl]-6-(naphthalen-2-yl)-[2,2']bipyridine (Compound 40) as a yellow-white powder.

Figure 2:
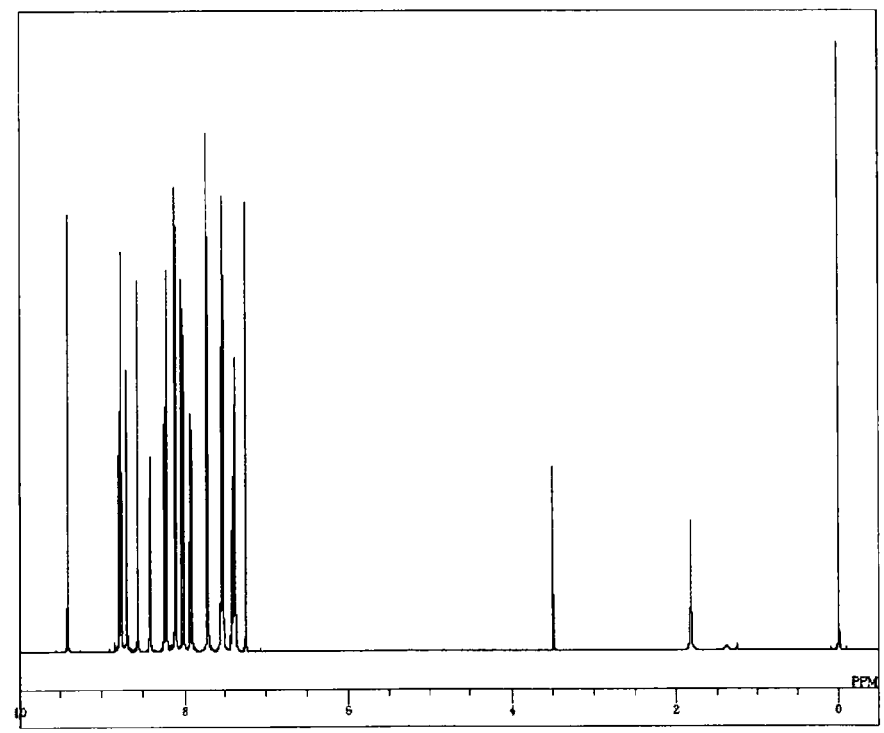
FIG. 2 is a 1H-NMR chart of the compound (Compound 40) of Invention Example 2.

The structure of the resulting yellow-white powder was identified using NMR. The results of 1H-NMR measurement are shown in FIG. 2.

The following 24 hydrogen signals were detected on 1H-NMR (CDCl$_3$). δ (ppm)=9.42 (1H), 8.76-8.80 (3H), 8.70 (1H), 8.57 (1H), 8.42 (1H), 8.22-8.25 (2H), 8.12 (2H), 8.03 (2H), 7.92-7.94 (2H), 7.73 (2H), 7.53-7.57 (4H), 7.38-7.43 (3H).

Example 3

Synthesis of 4,6-bis[4-(5H-pyrido[4,3-b]indol-5-yl)phenyl]-[2,2']bipyridine (Compound 164)

4,6-Bis(4-bromophenyl)-[2,2']bipyridine was synthesized in the same manner as in the above Example 1. 1.8 g of the resulting 4,6-bis(4-bromophenyl)-[2,2']bipyridine, 1.4 g of 5H-pyrido[4,3-b]indole, 0.2 g of copper powder, 1.6 g of potassium carbonate, 0.1 ml of dimethyl sulfoxide, and 5 ml of n-dodecane were added and the whole was stirred for 11 hours under heating and refluxing. After cooling to room temperature, 50 ml of methanol was added thereto and insoluble solid was removed by filtration. 300 ml of chloroform was added to the insoluble solid and extraction was performed. The extraction liquid was concentrated under reduced pressure to obtain a crude product. The crude product was subjected to purification using o-dichlorobenzene as a recrystallization solvent and drying was performed under reduced pressure at 70° C. for 12 hours to obtain 1.45 g (yield 58%) of 4,6-bis[4-(5H-pyrido[4,3-b]indol-5-yl)phenyl]-[2,2']bipyridine (Compound 164) as a yellow-white powder.

Figure 3:
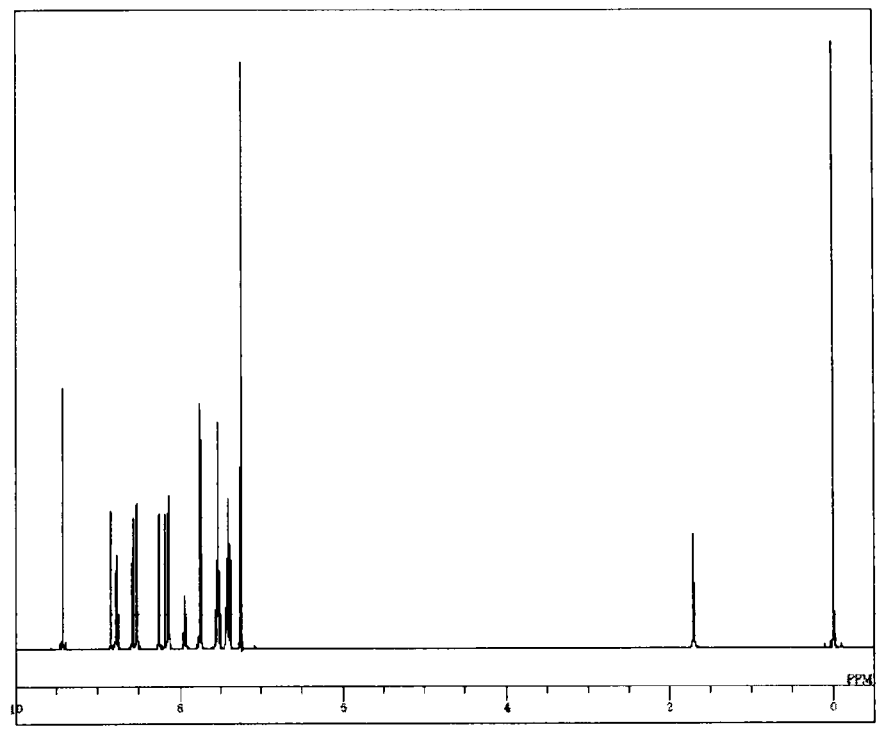
FIG. 3 is a 1H-NMR chart of the compound (Compound 164) of Invention Example 3.

The structure of the resulting yellow-white powder was identified using NMR. The results of 1H-NMR measurement are shown in FIG. 3.

The following 28 hydrogen signals were detected on 1H-NMR (CDCl$_3$). δ (ppm)=9.43 (2H), 8.76-8.84 (3H), 8.52-8.59 (4H), 8.14-8.26 (5H), 7.94 (1H), 7.76 (4H), 7.52-7.57 (4H), 7.39-7.44 (5H).

Example 4

Synthesis of 6-[4-(5H-pyrido[4,3-b]indol-5-yl)phenyl]-4-(naphthalen-1-yl)-[2,2']bipyridine (Compound 20)

6-(4-Bromophenyl)-4-(naphthalen-1-yl)-[2,2']bipyridine was synthesized in the same manner as in the above Example 1. 2.2 g of the resulting 6-(4-bromophenyl)-4-(naphthalen-1-yl)-[2,2']bipyridine, 0.9 g of 5H-pyrido[4,3-b]indole, 0.2 g of copper powder, 2.1 g of potassium carbonate, 0.2 ml of dimethyl sulfoxide, and 10 ml of n-dodecane were added and the whole was stirred for 6 hours under heating and refluxing. After cooling to room temperature, 60 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 2.02 g (yield 77%) of 6-[4-(5H-pyrido[4,3-b]indol-5-yl)phenyl]-4-(naphthalen-1-yl)-[2,2']bipyridine (Compound 20) as a brown-white powder.

Figure 4:
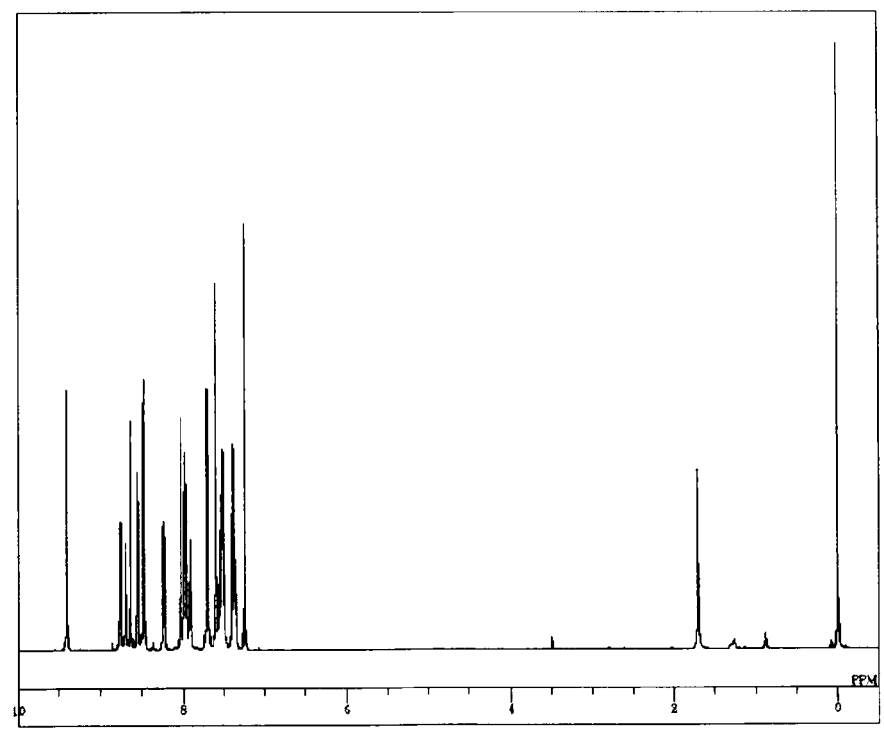
FIG. 4 is a 1H-NMR chart of the compound (Compound 20) of Invention Example 4.

The structure of the resulting brown-white powder was identified using NMR. The results of 1H-NMR measurement are shown in FIG. 4.

The following 24 hydrogen signals were detected on 1H-NMR (CDCl$_3$). δ (ppm)=9.41 (1H), 8.77 (1H), 8.70 (1H), 8.64 (1H), 8.56 (1H), 8.48 (2H), 8.24 (1H), 8.03 (1H), 7.90-8.00 (4H), 7.71 (2H), 7.50-7.61 (6H), 7.36-7.42 (3H).

Example 5

Synthesis of 4-[4-(5H-pyrido[4,3-b]indol-5-yl)phenyl]-6-(naphthalen-1-yl)-[2,2]bipyridine (Compound 24)

4-(4-Bromophenyl)-6-(naphthalen-1-yl)-[2,2']bipyridine was synthesized in the same manner as in the above Example 1. 2.2 g of the resulting 4-(4-bromophenyl)-6-(naphthalen-1-yl)-[2,2']bipyridine, 0.9 g of 5H-pyrido[4,3-b]indole, 0.2 g of copper powder, 2.1 g of potassium carbonate, 0.2 ml of dimethyl sulfoxide, and 10 ml of n-dodecane were added and the whole was stirred for 5 hours under heating and refluxing. After cooling to room temperature, 60 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 2.04 g (yield 77%) of 4-[4-(5H-pyrido[4,3-b]indol-5-yl)phenyl]-6-(naphthalen-1-yl)-[2,2']bipyridine (Compound 24) as a yellow-white powder.

Figure 5:
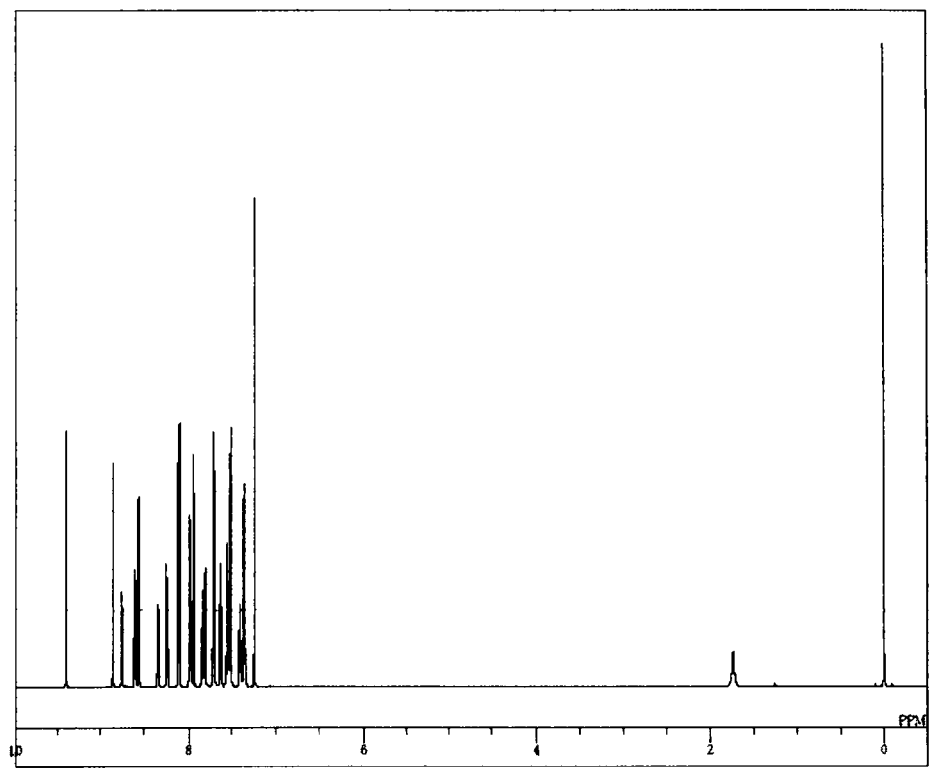
FIG. 5 is a 1H-NMR chart of the compound (Compound 24) of Invention Example 5.

The structure of the resulting yellow-white powder was identified using NMR. The results of 1H-NMR measurement are shown in FIG. 5.

The following 24 hydrogen signals were detected on 1H-NMR (CDCl$_3$). δ (ppm)=9.41 (1H), 8.86 (1H), 8.76 (1H), 8.60 (1H), 8.56 (1H), 8.35 (1H), 8.23 (1H), 8.10 (2H), 7.99 (2H), 7.94 (1H), 7.80-7.85 (2H), 7.71 (2H), 7.64 (1H), 7.52-7.57 (4H), 7.36-7.43 (3H).

Example 6

Synthesis of 6-[4-(5H-pyrido[3,2-b]indol-5-yl)phenyl]-4-(naphthalen-2-yl)-[2,2']bipyridine (Compound 37)

6-(4-Bromophenyl)-4-(naphthalen-2-yl)-[2,2']bipyridine was synthesized in the same manner as in the above Example 1. 2.5 g of the resulting 6-(4-bromophenyl)-4-(naphthalen-2-yl)-[2,2']bipyridine, 1.0 g of 5H-pyrido[3,2-b]indole, 0.2 g of copper powder, 2.4 g of potassium carbonate, 0.2 ml of dimethyl sulfoxide, and 10 ml of n-dodecane were added and the whole was stirred for 19 hours under heating and refluxing. After cooling to room temperature, 60 ml of chloroform was added thereto, insoluble solid was removed by filtration, and the filtrate was concentrated under reduced pressure to obtain a crude product. The crude product was subjected to purification using o-dichlorobenzene as a recrystallization solvent and drying was performed under reduced pressure at 70° C. for 12 hours to obtain 1.03 g (yield 34%) of 6-[4-(5H-pyrido[3,2-b]indol-5-yl)phenyl]-4-(naphthalen-2-yl)-[2,2']bipyridine (Compound 37) as a yellow-white powder.

Figure 6:
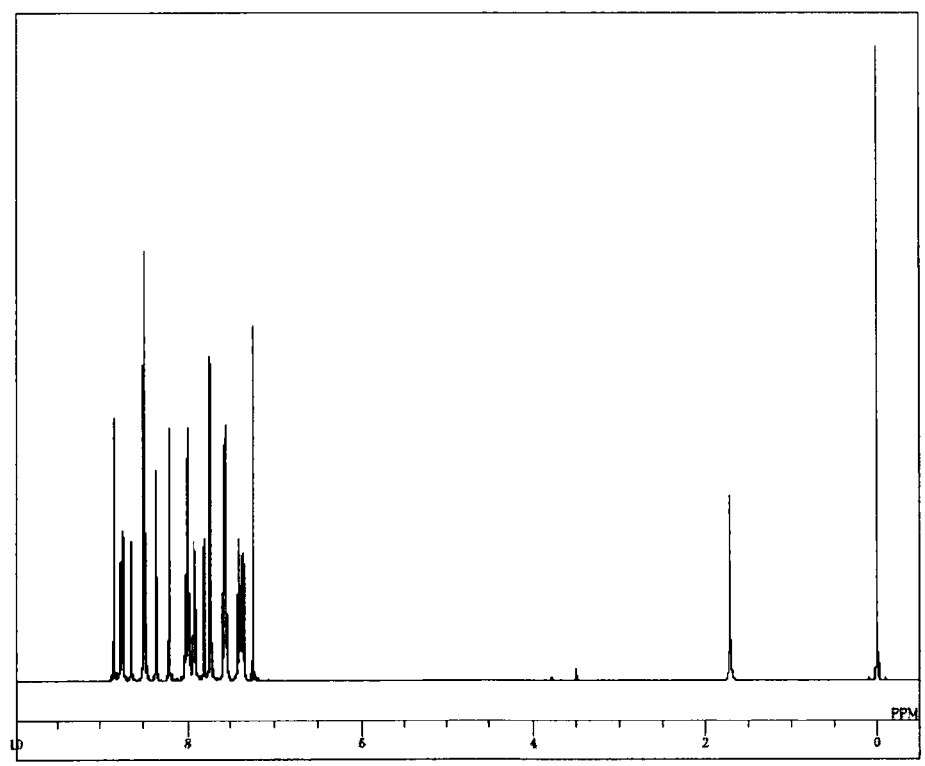
FIG. 6 is a 1H-NMR chart of the compound (Compound 37) of Invention Example 6.

The structure of the resulting yellow-white powder was identified using NMR. The results of 1H-NMR measurement are shown in FIG. 6.

The following 24 hydrogen signals were detected on 1H-NMR (CDCl$_3$). δ (ppm)=8.85 (1H), 8.78 (1H), 8.75 (1H), 8.65 (1H), 8.48-8.50 (3H), 8.36 (1H), 8.21 (1H), 7.98-8.03 (3H), 7.90-7.94 (2H), 7.81 (1H), 7.74 (2H), 7.55-7.60 (4H), 7.36-7.43 (3H).

Example 7

Synthesis of 4-[4-(5H-pyrido[3,2-b]indol-5-yl)phenyl]-6-(naphthalen-2-yl)-[2,2']bipyridine (Compound 41)

4-(4-Bromophenyl)-6-(naphthalen-2-yl)-[2,2']bipyridine was synthesized in the same manner as in the above Example 1. 2.5 g of the resulting 4-(4-bromophenyl)-6-(naphthalen-2-yl)-[2,2']bipyridine, 1.1 g of 5H-pyrido[3,2-b]indole, 0.2 g of copper powder, 2.4 g of potassium carbonate, 0.2 ml of dimethyl sulfoxide, and 10 ml of n-dodecane were added and the whole was stirred for 18 hours under heating and refluxing. After cooling to room temperature, 60 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 1.86 g (yield 62%) of 4-[4-(5H-pyrido[3,2-b]indol-5-yl)phenyl]-6-(naphthalen-2-yl)-[2,2']bipyridine (Compound 41) as a yellow-white powder.

Figure 7:
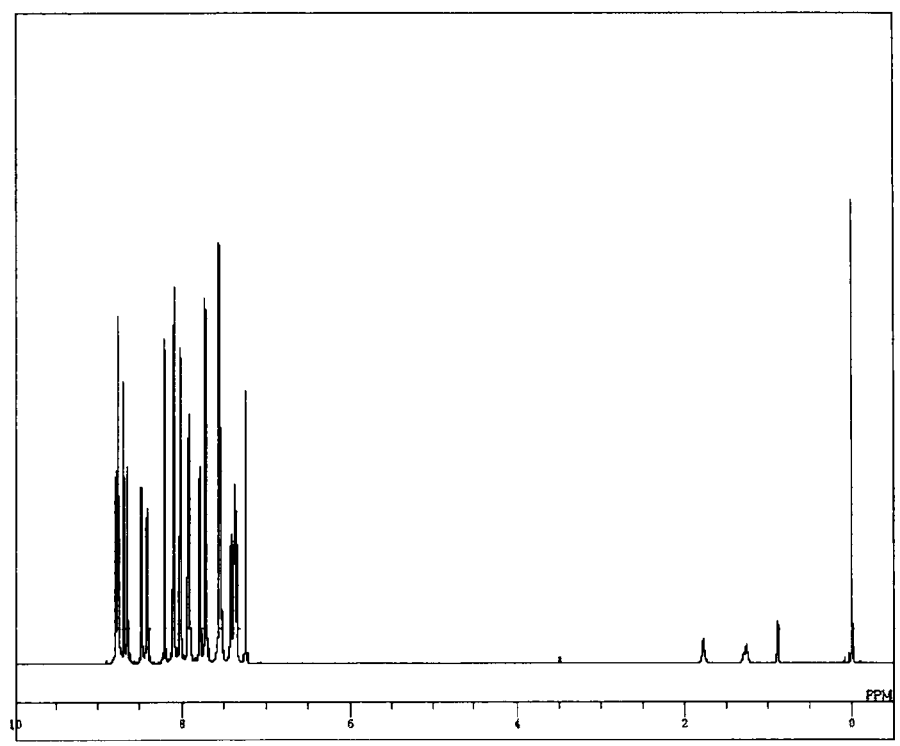
FIG. 7 is a 1H-NMR chart of the compound (Compound 41) of Invention Example 7.

The structure of the resulting yellow-white powder was identified using NMR. The results of 1H-NMR measurement are shown in FIG. 7.

The following 24 hydrogen signals were detected on 1H-NMR (CDCl$_3$). δ (ppm)=8.76-8.80 (3H), 8.70 (1H), 8.65 (1H), 8.48 (1H), 8.42 (1H), 8.21 (1H), 8.10 (1H), 8.02 (2H), 7.92 (2H), 7.79 (1H), 7.73 (2H), 7.55-7.57 (4H), 7.36-7.44 (3H).

Example 8

Synthesis of 6-[4-(5H-pyrido[4,3-b]indol-5-yl)phenyl]-4-(phenanthren-9-yl)-[2,2']bipyridine (Compound 52)

6-(4-Bromophenyl)-4-(phenanthren-9-yl)-[2,2']bipyridine was synthesized in the same manner as in the above Example 1. 2.6 g of the resulting 6-(4-bromophenyl)-4-(phenanthren-9-yl)-[2,2]bipyridine, 1.0 g of 5H-pyrido[4,3-b]indole, 0.2 g of copper powder, 2.2 g of potassium carbonate, 0.2 ml of dimethyl sulfoxide, and 10 ml of n-dodecane were added and the whole was stirred for 5 hours under heating and refluxing. After cooling to room temperature, 80 ml of chloroform was added thereto, insoluble solid was removed by filtration, and the filtrate was concentrated under reduced pressure to obtain a crude product. The crude product was purified by column chromatography (carrier: NH silica gel, eluent: toluene) to obtain 2.35 g (yield 78%) of 6-[4-(5H-pyrido[4,3-b]indol-5-yl)phenyl]-4-(phenanthren-9-yl)-[2,2'] bipyridine (Compound 52) as a pale red-white powder.

Figure 8:
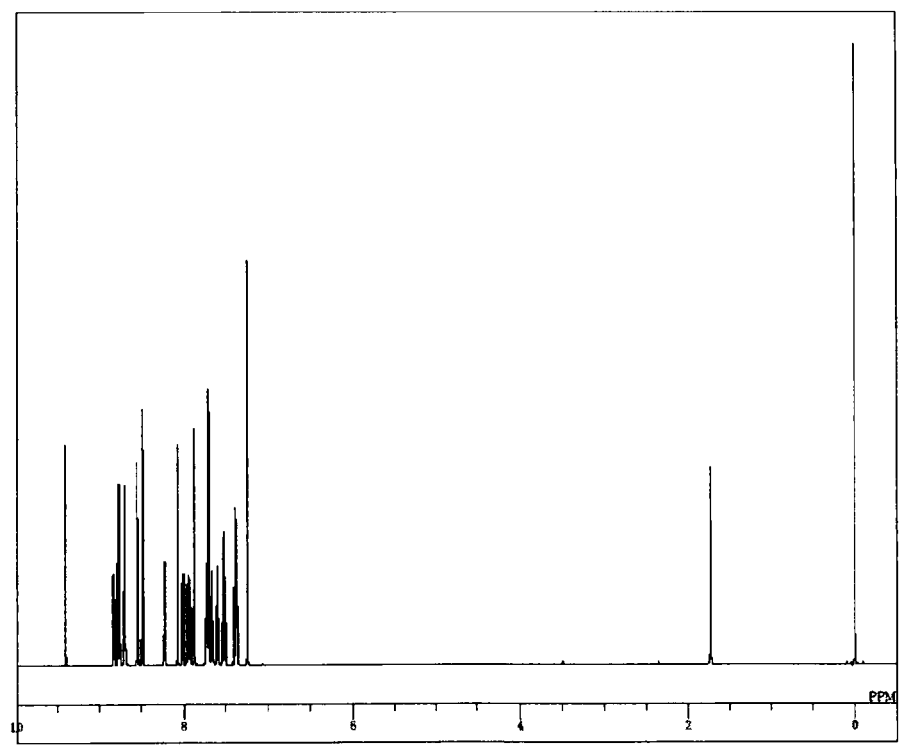
FIG. 8 is a 1H-NMR chart of the compound (Compound 52) of Invention Example 8.

The structure of the resulting pale red-white powder was identified using NMR. The results of 1H-NMR measurement are shown in FIG. 8.

The following 26 hydrogen signals were detected on 1H-NMR (CDCl$_3$). δ (ppm)=9.41 (1H), 8.83 (1H), 8.78 (2H), 8.70-8.72 (2H), 8.55 (1H), 8.49 (2H), 8.23 (1H), 8.08 (1H), 8.01 (1H), 7.91-7.96 (2H), 7.88 (1H), 7.71-7.75 (4H), 7.67 (1H), 7.61 (1H), 7.50-7.55 (2H), 7.37-7.41 (3H).

Example 9

Synthesis of 4-[4-(5H-pyrido[4,3-b]indol-5-yl)phenyl]-6-(phenanthren-2-yl)-[2,2']bipyridine (Compound 72)

4-(4-Bromophenyl)-6-(phenanthren-2-yl)-[2,2']bipyridine was synthesized in the same manner as in the above Example 1. 2.6 g of the resulting 4-(4-bromophenyl)-6-(phenanthren-2-yl)-[2,2]bipyridine, 1.0 g of 5H-pyrido[4,3-b]indole, 0.2 g of copper powder, 2.2 g of potassium carbonate, 0.2 ml of dimethyl sulfoxide, and 10 ml of n-dodecane were added and the whole was stirred for 6 hours under heating and refluxing. After cooling to room temperature, 80 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 1.40 g (yield 47%) of 4-[4-(5H-pyrido[4,3-b]indol-5-yl)phenyl]-6-(phenanthren-2-yl)-[2,2']bipyridine (Compound 72) as a pale red-white powder.

Figure 9:
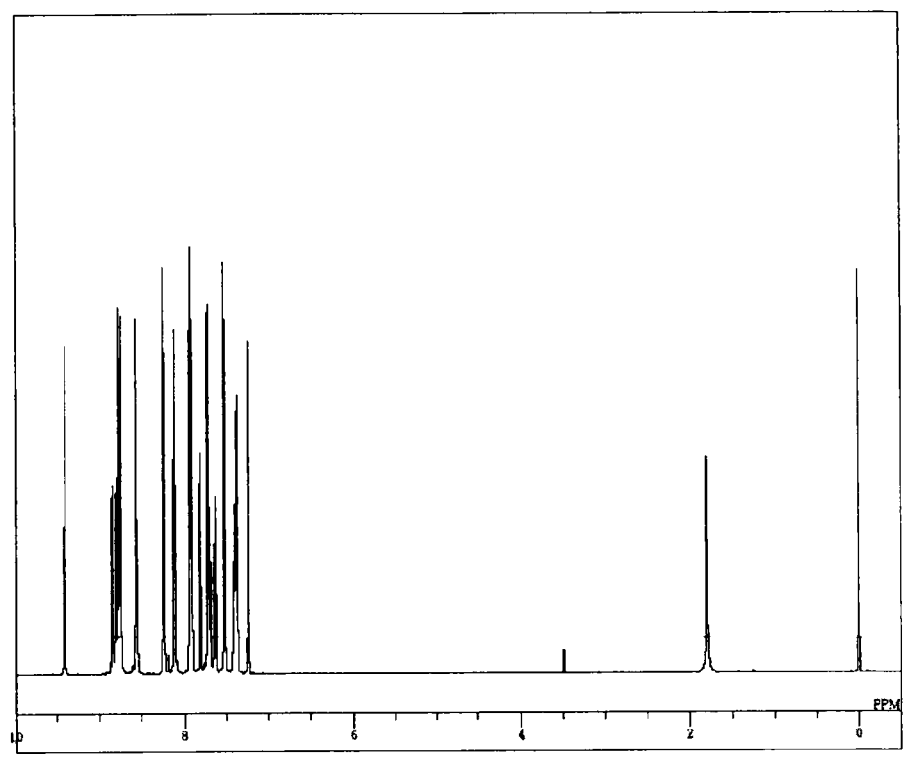
FIG. 9 is a 1H-NMR chart of the compound (Compound 72) of Invention Example 9.

The structure of the resulting pale red-white powder was identified using NMR. The results of 1H-NMR measurement are shown in FIG. 9.

The following 26 hydrogen signals were detected on 1H-NMR (CDCl$_3$). δ (ppm)=9.42 (1H), 8.75-8.86 (6H), 8.57 (2H), 8.24 (2H), 8.12 (2H), 7.91-7.95 (3H), 7.82 (1H), 7.63-7.73 (4H), 7.54 (2H), 7.38-7.43 (3H).

Example 10

Synthesis of 4-(biphenyl-4-yl)-6-[4-(5H-pyrido[4,3-b]indol-5-yl)phenyl]-[2,2]bipyridine (Compound 116)

4-(Biphenyl-4-yl)-6-(4-bromophenyl)-[2,2']bipyridine was synthesized in the same manner as in the above Example 1. 2.5 g of the resulting 4-(biphenyl-4-yl)-6-(4-bromophenyl)-[2,2']bipyridine, 1.0 g of 5H-pyrido[4,3-b]indole, 0.2 g of copper powder, 2.3 g of potassium carbonate, 0.2 ml of dimethyl sulfoxide, and 10 ml of n-dodecane were added and the whole was stirred for 5 hours under heating and refluxing. After cooling to room temperature, 80 ml of chloroform was added thereto, insoluble solid was removed by filtration, and the filtrate was concentrated under reduced pressure to obtain a crude product. The crude product was purified by column chromatography (carrier: NH silica gel, eluent: toluene/ethyl acetate) to obtain 2.81 g (yield 93%) of 4-(biphenyl-4-yl)-6-[4-(5H-pyrido[4,3-b]indol-5-yl)phenyl]-[2,2']bipyridine (Compound 116) as a yellow-white powder.

Figure 10:
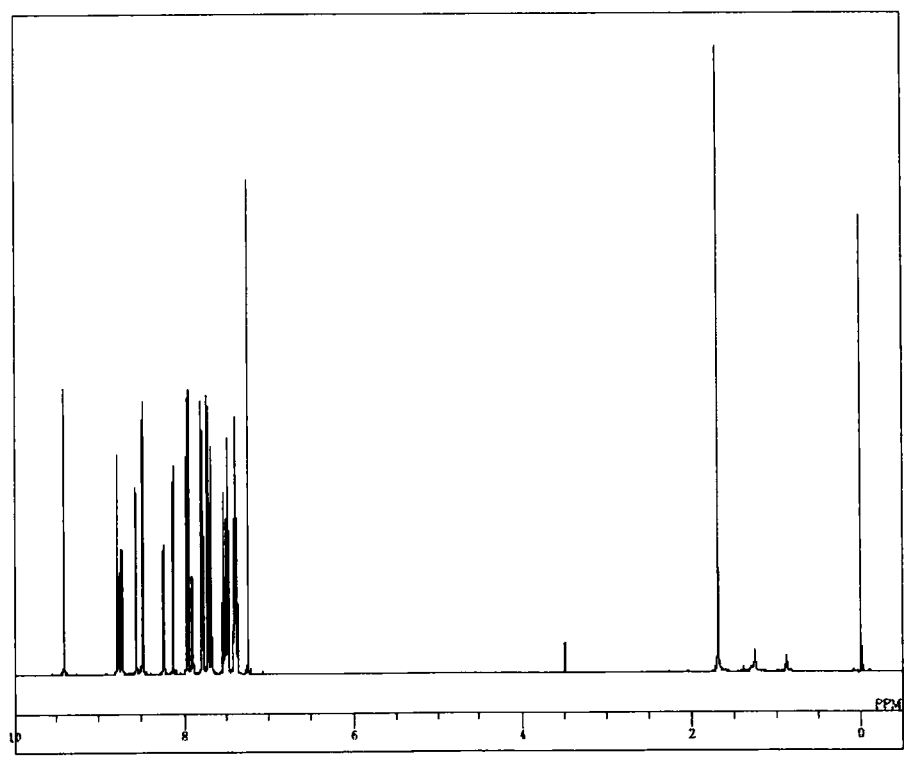
FIG. 10 is a 1H-NMR chart of the compound (Compound 116) of Invention Example 10.

The structure of the resulting yellow-white powder was identified using NMR. The results of 1H-NMR measurement are shown in FIG. 10.

The following 26 hydrogen signals were detected on 1H-NMR (CDCl$_3$). δ (ppm)=9.41 (1H), 8.78 (1H), 8.76 (1H), 8.73 (1H), 8.56 (1H), 8.49 (2H), 8.24 (1H), 8.13 (1H), 7.96 (2H), 7.91 (1H), 7.79 (2H), 7.73 (2H), 7.69 (2H), 7.48-7.56 (4H), 7.37-7.42 (4H).

Example 11

Synthesis of 4,6-bis[4-(5H-pyrido[3,2-b]indol-5-yl)phenyl]-[2,2']bipyridine (Compound 165)

4,6-Bis(4-bromophenyl)-[2,2']bipyridine was synthesized in the same manner as in the above Example 1. 2.2 g of the resulting 4,6-bis(4-bromophenyl)-[2,2']bipyridine, 1.7 g of 5H-pyrido[3,2-b]indole, 0.2 g of copper powder, 2.0 g of potassium carbonate, 0.2 ml of dimethyl sulfoxide, and 10 ml of n-dodecane were added and the whole was stirred for 18 hours under heating and refluxing. After cooling to room temperature, 50 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 1.50 g (yield 50%) of 4,6-bis[4-(5H-pyrido[3,2-b]indol-5-yl)phenyl]-[2,2']bipyridine (Compound 165) as a yellow-white powder.

Figure 11:
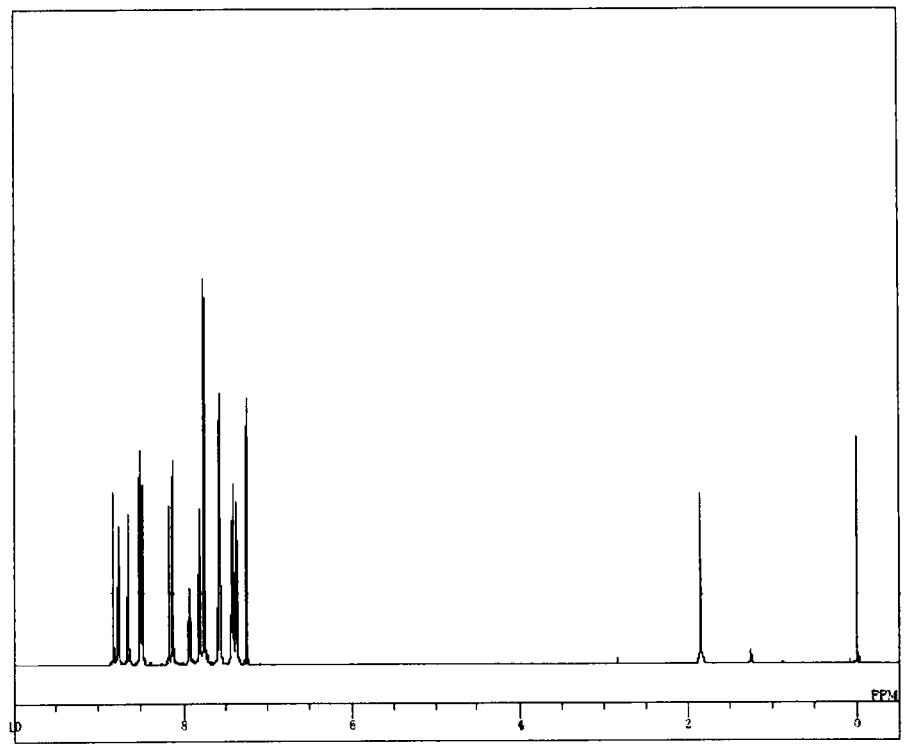
FIG. 11 is a 1H-NMR chart of the compound (Compound 165) of Invention Example 11.

The structure of the resulting yellow-white powder was identified using NMR. The results of 1H-NMR measurement are shown in FIG. 11.

The following 28 hydrogen signals were detected on 1H-NMR (CDCl$_3$). δ (ppm)=8.83 (1H), 8.76-8.78 (2H), 8.66 (2H), 8.48-8.52 (4H), 8.17 (1H), 8.13 (2H), 7.94 (1H), 7.81 (2H), 7.76 (4H), 7.56-7.61 (4H), 7.36-7.44 (5H).

Example 12

Synthesis of 4-[4-(5H-pyrido[4,3-b]indol-5-yl)phenyl]-6-(phenanthren-9-yl)-[2,2]bipyridine (Compound 192)

4-(4-Bromophenyl)-6-(phenanthren-9-yl)-[2,2']bipyridine was synthesized in the same manner as in the above Example 1. 2.2 g of the resulting 4-(4-bromophenyl)-6-(phenanthren-9-yl)-[2,2']bipyridine, 0.8 g of 5H-pyrido[4,3-b]indole, 0.2 g of copper powder, 1.8 g of potassium carbonate, 0.2 ml of dimethyl sulfoxide, and 10 ml of n-dodecane were added and the whole was stirred for 8 hours under heating and refluxing. After cooling to room temperature, 80 ml of chloroform was added thereto, insoluble solid was removed by filtration, and the filtrate was concentrated under reduced pressure to obtain a crude product. The crude product was purified by column chromatography (carrier: NH silica gel, eluent: hexane/chloroform) to obtain 1.36 g (yield 54%) of 4-[4-(5H-pyrido[4,3-b]indol-5-yl)phenyl]-6-(phenanthren-9-yl)-[2,2']bipyridine (Compound 192) as a yellow-white powder.

Figure 12:
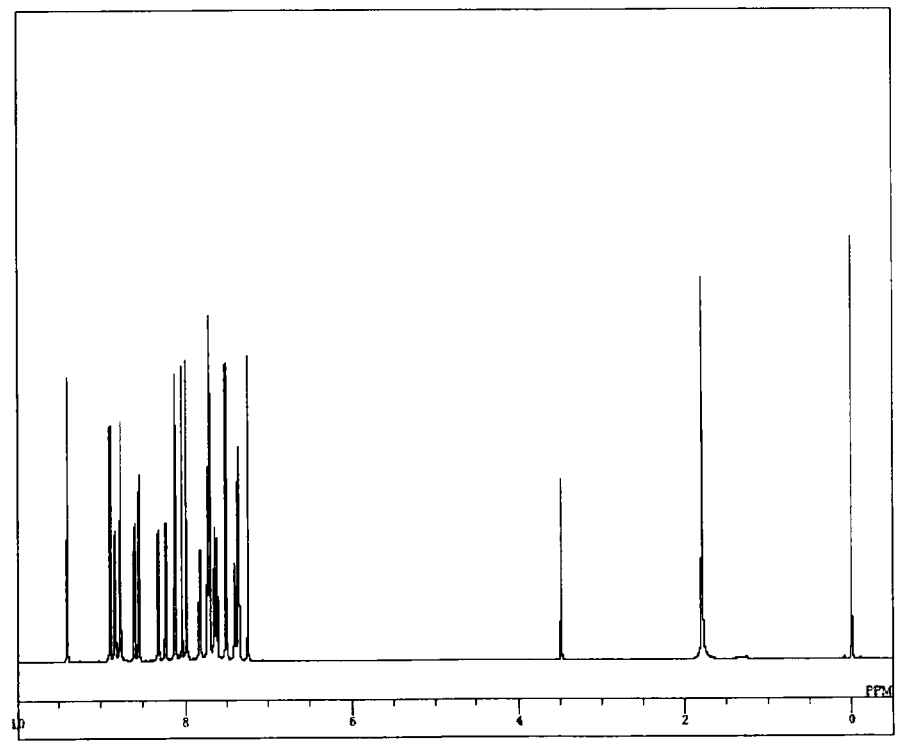
FIG. 12 is a 1H-NMR chart of the compound (Compound 192) of Invention Example 12.

The structure of the resulting yellow-white powder was identified using NMR. The results of 1H-NMR measurement are shown in FIG. 12.

The following 26 hydrogen signals were detected on 1H-NMR (CDCl$_3$). δ (ppm)=9.40 (1H), 8.89 (1H), 8.84 (1H), 8.78 (2H), 8.61 (1H), 8.55 (1H), 8.32 (1H), 8.23 (1H), 8.12 (2H), 8.04 (1H), 7.99 (2H), 7.83 (1H), 7.71-7.74 (4H), 7.62-7.67 (2H), 7.52 (2H), 7.37-7.42 (3H).

Example 13

Synthesis of 6-(biphenyl-4-yl)-4-[4-(5H-pyrido[4,3-b]indol-5-yl)phenyl]-[2,2']bipyridine (Compound 193)

6-(Biphenyl-4-yl)-4-(4-bromophenyl)-[2,2']bipyridine was synthesized in the same manner as in the above Example 1. 2.5 g of the resulting 6-(biphenyl-4-yl)-4-(4-bromophenyl)-[2,2']bipyridine, 1.0 g of 5H-pyrido[4,3-b]indole, 0.2 g of copper powder, 2.3 g of potassium carbonate, 0.2 ml of dimethyl sulfoxide, and 10 ml of n-dodecane were added and the whole was stirred for 7 hours under heating and refluxing. After cooling to room temperature, 80 ml of chloroform was added thereto, insoluble solid was removed by filtration, and the filtrate was concentrated under reduced pressure to obtain a crude product. The crude product was purified by column chromatography (carrier: NH silica gel, eluent: toluene/ethyl acetate) to obtain 1.96 g (yield 65%) of 6-(biphenyl-4-yl)-4-[4-(5H-pyrido[4,3-b]indol-5-yl)phenyl]-[2,2']bipyridine (Compound 193) as a white powder.

Figure 13:
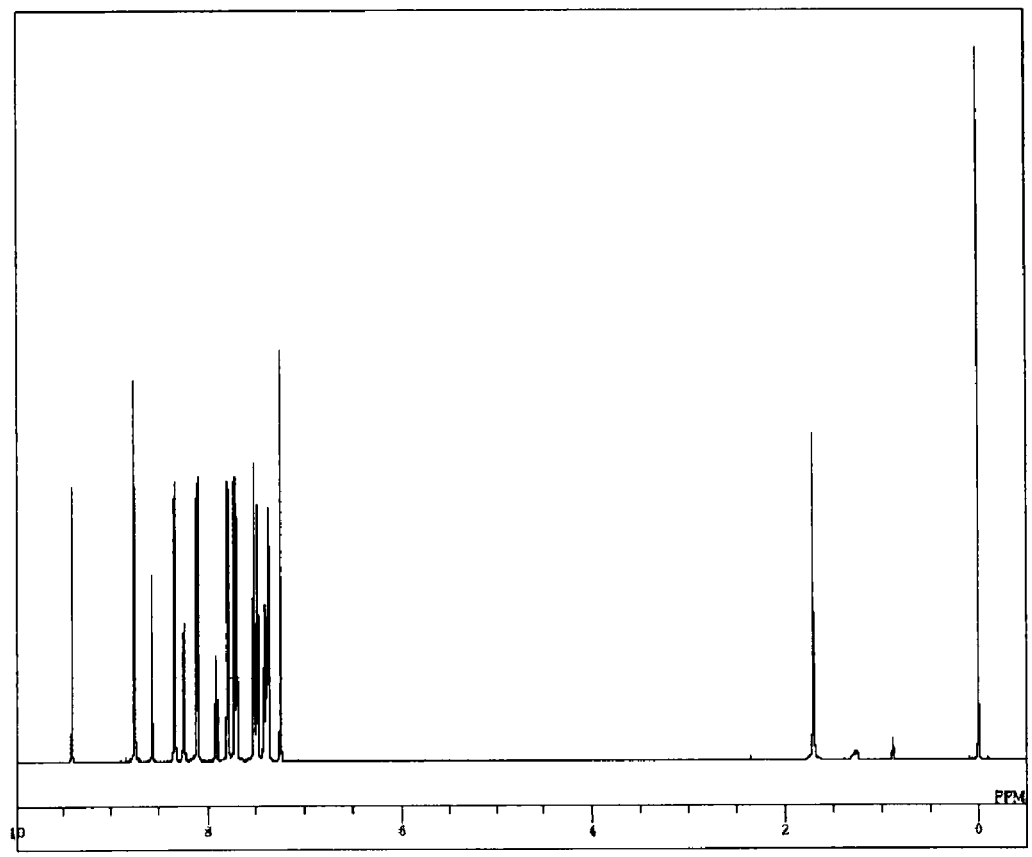
FIG. 13 is a 1H-NMR chart of the compound (Compound 193) of Invention Example 13.

The structure of the resulting white powder was identified using NMR. The results of 1H-NMR measurement are shown in FIG. 13.

The following 26 hydrogen signals were detected on 1H-NMR (CDCl$_3$). δ (ppm)=9.42 (1H), 8.76 (3H), 8.57 (1H), 8.34 (2H), 8.25 (1H), 8.11 (3H), 7.91 (1H), 7.80 (2H), 7.70-7.73 (4H), 7.49-7.53 (4H), 7.38-7.43 (4H).

Example 14

For the compounds of the invention, melting point and glass transition point were determined by means of a highly sensitive differential scanning calorimeter (DSC 3100S manufactured by Bruker AXS). The results are shown in Table 1.

TABLE 1

| | Melting Point | Glass Transition Point |
|---|---|---|
| Compound of Example 1 | 244° C. | 114° C. |
| Compound of Example 2 | 253° C. | 117° C. |

TABLE 1-continued

| | Melting Point | Glass Transition Point |
|---|---|---|
| Compound of Example 3 | 339° C. | 161° C. |
| Compound of Example 4 | 152° C. | 115° C. |
| Compound of Example 5 | 151° C. | 116° C. |
| Compound of Example 6 | 218° C. | 108° C. |
| Compound of Example 7 | 248° C. | 110° C. |
| Compound of Example 8 | 181° C. | 139° C. |
| Compound of Example 9 | 271° C. | 139° C. |
| Compound of Example 10 | 150° C. | 112° C. |
| Compound of Example 11 | 343° C. | 155° C. |
| Compound of Example 12 | 186° C. | 132° C. |
| Compound of Example 13 | 231° C. | 114° C. |

The compounds of the invention show a glass transition point of 100° C. or higher, and thus are stable in a thin-film state.

Example 15

Using each of the compounds of the invention, a deposited film having a film thickness of 100 nm was prepared on an ITO substrate and work function was measured on a photoelectron spectroscopy in air (Model AC-3, manufactured by Riken Keiki Co., Ltd.). The results are shown in Table 2.

TABLE 2

| | Work Function |
|---|---|
| Compound of Example 1 | 6.11 eV |
| Compound of Example 2 | 6.18 eV |
| Compound of Example 3 | 6.15 eV |
| Compound of Example 4 | 6.25 eV |
| Compound of Example 5 | 6.33 eV |
| Compound of Example 6 | 5.99 eV |
| Compound of Example 7 | 6.12 eV |
| Compound of Example 8 | 6.27 eV |
| Compound of Example 9 | 6.34 eV |
| Compound of Example 10 | 6.27 eV |
| Compound of Example 11 | 6.15 eV |
| Compound of Example 12 | 6.37 eV |
| Compound of Example 13 | 6.16 eV |

Thus, the compounds of the invention have values deeper than a work function of 5.4 eV possessed by common hole-transporting materials such as NPD and TPD and have a large hole-blocking ability.

Example 16

Figure 14:
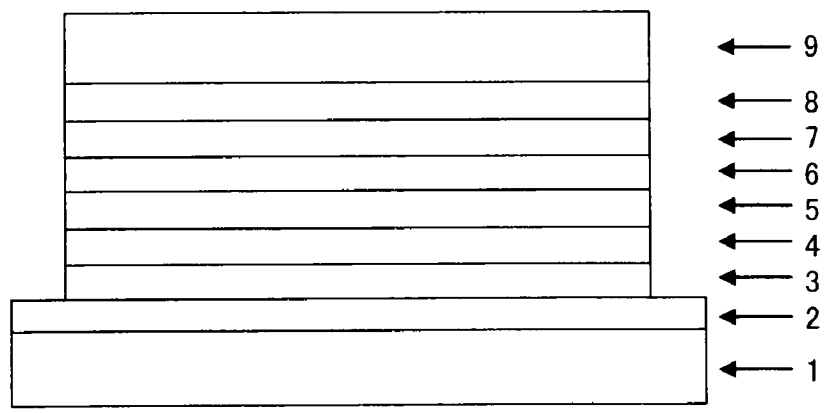
FIG. 14 is a drawing showing the constitution of the EL devices of Examples 16 to 24.
Figure 15:
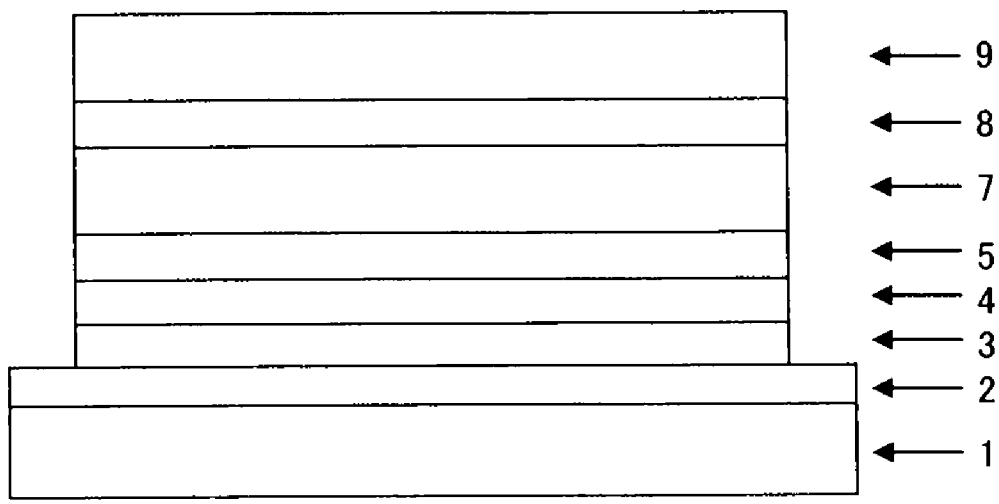
FIG. 15 is a drawing showing the constitution of the EL device of Comparative Example 1.

An organic EL device was prepared by depositing a hole-injecting layer 3, a hole-transporting layer 4, an emitting layer 5, a hole-blocking layer 6, an electron-transporting layer 7, an electron-injecting layer 8, and a cathode (aluminum electrode) 9 in this order on a glass substrate 1 on which an ITO electrode had been formed as a transparent anode 2 in advance, as shown in FIG. 14.

After the glass substrate 1 on which ITO having a film thickness of 150 nm had been formed was washed with an organic solvent, the surface was washed by UV ozone treatment. It was mounted in a vacuum deposition machine, which was then evacuated to 0.001 Pa or lower.

Subsequently, copper phthalocyanine was formed thereon at a deposition rate of 3.6 nm/min to a thickness of about 20 nm as the hole-injecting layer 3. NPD was formed on the hole-injecting layer 3 at a deposition rate of 3.6 nm/min to a thickness of about 40 nm as the hole-transporting layer 4. As the emitting layer 5, Alq3 was formed on the hole-transporting layer 4 at a deposition rate of 3.6 nm/min to a thickness of about 30 nm. On the emitting layer 5, the compound of invention Example 1 (Compound 36) was formed at a deposition rate of 3.6 nm/min to a thickness of about 30 nm as the hole-blocking layer-cum-electron-transporting layer 6 and 7. On the hole-blocking layer-cum-electron-transporting layer 6 and 7, lithium fluoride was formed at a deposition rate of 0.36 nm/min to a thickness of about 0.5 nm as the electron-injecting layer 8. Finally, aluminum was deposited to a thickness of about 200 nm to form the cathode 9. The prepared device was stored in a vacuum desiccator and characteristic properties were measured in the atmosphere at ordinary temperature.

The results of measuring luminescence properties when direct voltage was applied to the organic EL device prepared using the compound of invention Example 1 (Compound 36) of the invention are summarized in Table 3.

Example 17

An organic EL device was prepared under the same conditions as in Example 16 except that the material of the hole-blocking layer-cum-electron-transporting layer 6 and 7 was replaced by the compound of invention Example 2 (Compound 40), and characteristic properties thereof were investigated.

The results of measuring luminescence properties when direct voltage was applied to the organic EL device prepared using the compound of invention Example 2 (Compound 40) of the invention are summarized in Table 3.

Example 18

An organic EL device was prepared under the same conditions as in Example 16 except that the material of the hole-blocking layer-cum-electron-transporting layer 6 and 7 was replaced by the compound of invention Example 10 (Compound 116), and characteristic properties thereof were investigated.

The results of measuring luminescence properties when direct voltage was applied to the organic EL device prepared using the compound of invention Example 10 (Compound 116) of the invention are summarized in Table 3.

Comparative Example 1

For comparison, an organic EL device was prepared under the same conditions as in Example 16 except that the material of the hole-blocking layer-cum-electron-transporting layer 6 and 7 was replaced by Alq3 as the electron-transporting layer 7, and characteristic properties thereof were investigated. The results of measurement are shown in Tables 3 and 4.

Thus, it was revealed that the organic EL devices of the invention are excellent in luminous efficiency and can achieve remarkable decrease in driving voltage, as compared with the devices using Alq3 which is a commonly employed general electron-transporting material.

Example 19

An organic EL device was prepared under the same conditions as in Example 16 except that the material of the hole-blocking layer-cum-electron-transporting layer 6 and 7 was replaced by the compound of invention Example 3 (Compound 164), and characteristic properties thereof were investigated.

The results of measuring luminescence properties when direct voltage was applied to the organic EL device prepared using the compound of invention Example 3 (Compound 164) of the invention are summarized in Table 4.

Example 20

An organic EL device was prepared under the same conditions as in Example 16 except that the material of the hole-blocking layer-cum-electron-transporting layer 6 and 7 was replaced by the compound of invention Example 5 (Compound 24), and characteristic properties thereof were investigated.

The results of measuring luminescence properties when direct voltage was applied to the organic EL device prepared using the compound of invention Example 5 (Compound 24) of the invention are summarized in Table 4.

Example 21

An organic EL device was prepared under the same conditions as in Example 16 except that the material of the hole-blocking layer-cum-electron-transporting layer 6 and 7 was replaced by the compound of invention Example 6 (Compound 37), and characteristic properties thereof were investigated.

The results of measuring luminescence properties when direct voltage was applied to the organic EL device prepared using the compound of invention Example 6 (Compound 37) of the invention are summarized in Table 4.

Example 22

An organic EL device was prepared under the same conditions as in Example 16 except that the material of the hole-blocking layer-cum-electron-transporting layer 6 and 7 was replaced by the compound of invention Example 7 (Compound 41), and characteristic properties thereof were investigated.

TABLE 3

| | Compound | Voltage [V] (@10 mA/cm$^2$) | Luminance [cd/m$^2$] (@10 mA/cm$^2$) | Luminous Efficiency [cd/A] (@10 mA/cm$^2$) | Power efficiency [lm/W] (@10 mA/cm$^2$) |
|---|---|---|---|---|---|
| Example 16 | Compound 36 | 5.90 | 480 | 4.80 | 2.54 |
| Example 17 | Compound 40 | 6.05 | 460 | 4.60 | 2.38 |
| Example 18 | Compound 116 | 6.35 | 464 | 4.64 | 2.29 |
| Comparative Example 1 | Alq3 | 6.60 | 450 | 4.50 | 2.13 |

The results of measuring luminescence properties when direct voltage was applied to the organic EL device prepared using the compound of invention Example 7 (Compound 41) of the invention are summarized in Table 4.

Example 23

An organic EL device was prepared under the same conditions as in Example 16 except that the material of the hole-blocking layer-cum-electron-transporting layer 6 and 7 was replaced by the compound of invention Example 12 (Compound 192), and characteristic properties thereof were investigated.

The results of measuring luminescence properties when direct voltage was applied to the organic EL device prepared using the compound of invention Example 12 (Compound 192) of the invention are summarized in Table 4.

Example 24

An organic EL device was prepared under the same conditions as in Example 16 except that the material of the hole-blocking layer-cum-electron-transporting layer 6 and 7 was replaced by the compound of invention Example 13 (Compound 193), and characteristic properties thereof were investigated.

The results of measuring luminescence properties when direct voltage was applied to the organic EL device prepared using the compound of invention Example 13 (Compound 193) of the invention are summarized in Table 4.

TABLE 4

| | Compound | Luminance [cd/m$^2$] (@10 mA/ cm$^2$) | Luminous Efficiency [cd/A] (@10 mA/ cm$^2$) | Power efficiency [lm/W] (@10 mA/ cm$^2$) |
|---|---|---|---|---|
| Example 19 | Compound 164 | 515 | 5.15 | 2.32 |
| Example 20 | Compound 24 | 495 | 4.95 | 2.30 |
| Example 21 | Compound 37 | 485 | 4.85 | 1.81 |
| Example 22 | Compound 41 | 465 | 4.65 | 1.59 |
| Example 23 | Compound 192 | 490 | 4.90 | 2.06 |
| Example 24 | Compound 193 | 455 | 4.55 | 2.04 |
| Comparative Example 1 | Alq3 | 450 | 4.50 | 2.13 |

Thus, it was revealed that the organic EL devices of the invention have high luminance per unit current density and are excellent in luminous efficiency, as compared with the devices using Alq3 which is a commonly employed general electron-transporting material.

While the invention has been described in detail and with reference to specific embodiments thereof, it will be apparent to one skilled in the art that various changes and modifications can be made therein without departing from the spirit and scope thereof.

The present application is based on Japanese Patent Application No. 2007-066214 filed on Mar. 15, 2007, and the contents are incorporated herein by reference.

INDUSTRIAL APPLICABILITY

Since the compound having a substituted bipyridyl group and a pyridoindole ring structure connected with each other through a phenylene group according to the invention exhibits a good injection property of electrons and is stable in a thin-film state, the compound is excellent as a compound for organic EL devices. By preparing organic EL devices using the compound, driving voltage can be decreased and durability can be improved. For example, it becomes possible to spread the applications onto electric home appliances and illumination.

The invention claimed is:

1. A compound, having:
   a substituted bipyridyl group;
   a phenylene group; and
   a pyridoindole ring structure,
   wherein the bipyridyl group and the pyridoindole ring structure are connected with each other through phenylene group, and
   wherein the compound is represented by the following formula (1):

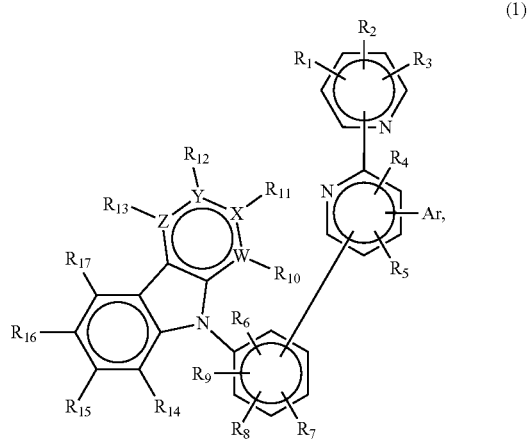

wherein
Ar represents a substituted or unsubstituted aromatic hydrocarbon group, a substituted or unsubstituted aromatic heterocyclic group, or a substituted or unsubstituted condensed polycyclic aromatic group, provided that Ar is not pyridyl,
R1 to R17 are the same or different and represent a hydrogen atom, a fluorine atom, a chlorine atom, a cyano group, a trifluoromethyl group, a linear or branched alkyl group comprising 1 to 6 carbon atoms, or a substituted or unsubstituted aromatic hydrocarbon group, and
W, X, Y, and Z represent a carbon atom or a nitrogen atom, provided that only one of W, X, Y, and Z is a nitrogen atom and the nitrogen atom does not have a substituent of R10, R11, R12, or R13.

2. An organic electroluminescence device, comprising:
   a pair of electrodes; and
   at least one organic layer interposed between the electrodes,
   wherein the at least one organic layer comprises the compound of claim 1.

3. The device of claim 2, wherein the at least one organic layer is an electron-transporting layer.

4. The device of claim 2, wherein the at least one organic layer is a hole-blocking layer.

5. The device of claim 2, wherein the at least one organic layer is an emitting layer.

6. The device of claim 2, wherein the at least one organic layer is an electron-injecting layer.

7. The compound of claim 1, having a formula
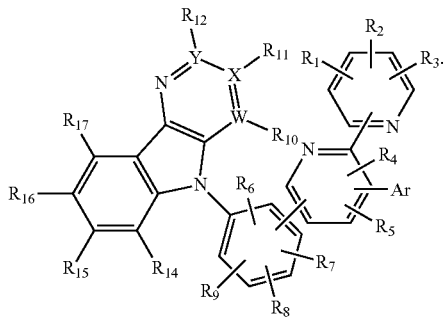
8. The compound of claim 1, having a formula
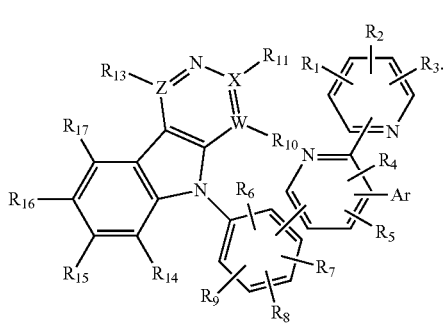
9. The compound of claim 1, having a formula
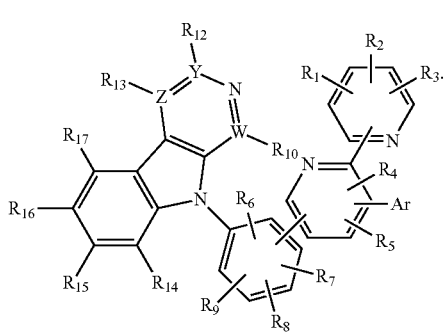
10. The compound of claim 1, having a formula
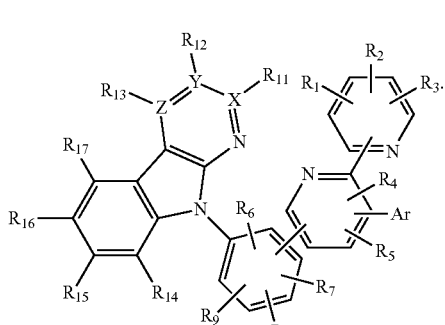
11. The compound of claim 1, having a formula
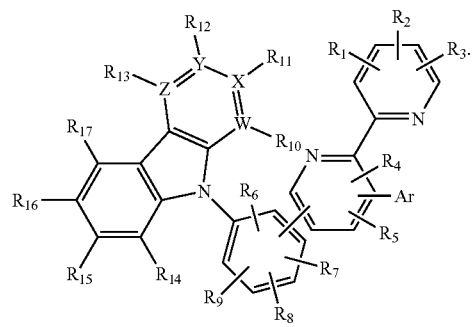
12. The compound of claim 1, having a formula
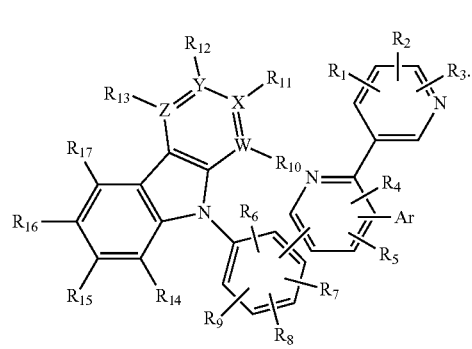
13. The compound of claim 1, having a formula
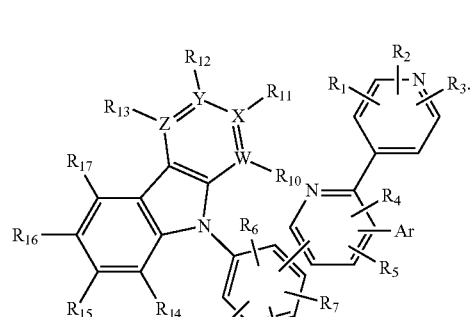
14. The compound of claim 1, having a formula
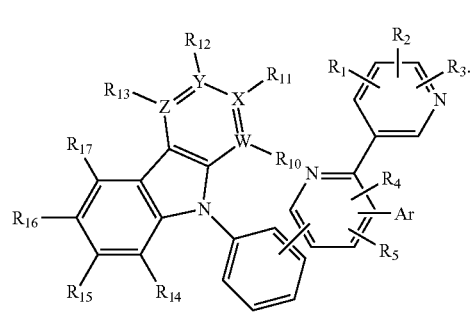

15. The compound of claim 1, having a formula

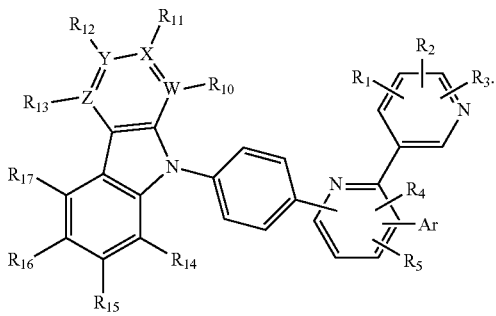

16. The compound of claim 1, having a formula

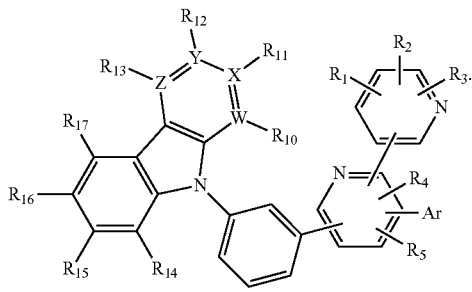

17. The compound of claim 1, wherein R1 to R17 are independently a hydrogen atom, a fluorine atom, a chlorine atom, a cyano group, a trifluoromethyl group, a linear or branched alkyl group comprising 1 to 6 carbon atoms, a substituted or unsubstituted phenyl group, a substituted or unsubstituted biphenyl group, a substituted or unsubstituted terphenyl group, a substituted or unsubstituted tetrakisphenyl group, a substituted or unsubstituted styryl group, a substituted or unsubstituted naphthyl group, a substituted or unsubstituted fluorenyl group, a substituted or unsubstituted phenanthryl group, a substituted or unsubstituted indenyl group, or a substituted or unsubstituted pyrenyl group.

18. The compound of claim 1, wherein Ar is a phenyl group, a biphenyl group, a terphenyl group, a tetrakisphenyl group, a styryl group, a naphthyl group, an anthryl group, an acenaphthenyl group, a fluorenyl group, a phenanthryl group, an indenyl group, a pyrenyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, or an acridinyl group.

19. The compound of claim 1, wherein Ar is substituted or unsubstituted and is a phenyl or naphthyl group.

20. The compound of claim 1, wherein the substituted or unsubstituted aromatic hydrocarbon group is present for at least one of R6 to R9 and is a phenyl, biphenyl, terphenyl, tetrakisphenyl, styryl, naphthyl, fluorenyl, phenanthryl, indenyl, or pyrenyl.

* * * * *